(12) United States Patent
Allen et al.

(10) Patent No.: US 7,880,055 B2
(45) Date of Patent: Feb. 1, 2011

(54) LECITIN-LIKE PROTEIN KINASE STRESS-RELATED POLYPEPTIDES AND METHODS OF USE IN PLANTS

(75) Inventors: Damian Allen, Cary, NC (US); Lori V. Mills, Willow Springs, NC (US); Pilar Puente, Speyer (DE); Nocha van Thielen, Durham, NC (US); Oswaldo da Costa e Silva, Neustadt (DE)

(73) Assignee: BASF Plant Science GmbH (DE)

( * ) Notice: Subject to any disclaimer, the term of this patent is extended or adjusted under 35 U.S.C. 154(b) by 689 days.

(21) Appl. No.: 11/917,536

(22) PCT Filed: Jun. 16, 2006

(86) PCT No.: PCT/EP2006/063270

§ 371 (c)(1),
(2), (4) Date: Dec. 14, 2007

(87) PCT Pub. No.: WO2006/134162

PCT Pub. Date: Dec. 21, 2006

(65) Prior Publication Data

US 2009/0158454 A1    Jun. 18, 2009

Related U.S. Application Data

(60) Provisional application No. 60/692,005, filed on Jun. 17, 2005.

(51) Int. Cl.
| | |
|---|---|
| C12N 15/82 | (2006.01) |
| C12N 15/29 | (2006.01) |
| A01H 5/00 | (2006.01) |
| A01H 5/10 | (2006.01) |
| C07K 14/415 | (2006.01) |

(52) U.S. Cl. .................. 800/289; 435/468; 435/419; 800/298; 530/370; 536/23.6

(58) Field of Classification Search .................. None
See application file for complete search history.

(56) References Cited

U.S. PATENT DOCUMENTS

2008/0271210 A1 * 10/2008 Kolesnik et al. ............ 800/298

FOREIGN PATENT DOCUMENTS

| WO | WO 01/45492 | 6/2001 |
| WO | WO 02/10210 | 2/2002 |

OTHER PUBLICATIONS

Barre Annick, Lectin Receptor Kinases in Plants, Critical Reviews in Plant Sciences, 2002, 21(4)379-399.
Zuo Kaijing, Molecular Cloning and Characterization of GhlecRK, a Novel Inase Gene with Lectin-like Domain from *Gossypium hirsutum*, DNA Sequence, 2004, 15(1) 58-65.
He, X.J., A salt-responsive recptor-like kinase gene regulated by the ethylene signaling pathway encodes a plasma membrane serine/theonine kinase. Theor Appl Genet 2004 109, 3.
Maria-Teresa Navarro-Gochicoa, Characterization of four lectin-like . . . Plant Physiology 2003 133, 1893-1910.

* cited by examiner

*Primary Examiner*—Cynthia Collins
(74) *Attorney, Agent, or Firm*—Patricia A. McDaniels

(57) ABSTRACT

A transgenic plant transformed by a Lectin-like Protein Kinase Stress-Related Polypeptide (LPKSRP) coding nucleic acid, wherein expression of the nucleic acid sequence in the plant results in increased plant growth and/or increased tolerance to an environmental stress as compared to a wild type variety of the plant. Also provided are agricultural products, including seeds, produced by the transgenic plants. Also provided are isolated LPKSRPs, and isolated nucleic acids coding LPKSRPs, and vectors and host cells containing the latter.

14 Claims, 10 Drawing Sheets

FIGURE 1

Nucleotide sequence of the PpLLPK-1 from *Physcomitrella patens* (SEQ ID NO:1)

TTTCTAAGCTATTCAACCTGGATTGATTTCAGTATGCAGATTAACAACGGTTTCTTGC
ACTTGGTGTCTACCCTCCTAGGTTTACTTCATTTAGCAACTTTTGCCACAGCTGAATT
GAAAACTATTGAATTTAGTTTTCCTAATTTTAAGAGTCCGGAGAATGATGGTACAAT
CAACATTCCGAATGCAACAGATGTGCCTAGTGGTAGGAACGTCCTCTTCCTTCCCAA
GGAAAAGAACGCCATGAGTGTTGGGTGGGTTATTTATGAAGAGAAAGTTCAATTCT
GGGACAACTCCGATGACGCTGCTTCTTTTAGTACAGAGTTTACCTTCAGTACTTCAG
GTTACAATGCGTCAACCGGAGGTAGCGGACTTGCATTCTTGATAACTCCAGATTTTT
CCATCGGTGACATTCGTGGATACCTTGGGATATTTCATCGACAACCAACGCCTCCA
CAAACAATCAAAAGATTGCAGTGGAGATTGATGTTTTCAAGAACCCATGGGATCCA
AGCGCCAGCCACATTGGCTTAGACGTAAACTCCATCGAATCCGTGAAGGTAAAAGA
CTATTGTCCGGTGATGGATAACCGTTGCACTTACTTTACCAACAAAGGGGACATCAA
TGTTTGGATTGACTACATGGCTGAAAGTGAGACTCTTGAAGTGCGCTTAGCAATGGG
TTCAAGCAGTGTGAAGCCAACCCAGCCGGATCTACAATTCATTGGATTGAACTTGCC
AAGGACTATCCGAAACTTTATGTATGTGGGGTTTTCAGCAGCCACTGGAAGTGACTT
TTATCCTGCACACACATTTCGATTACGTCGATGGAGCTTTAAAACTACGGCTCCGTC
CAACGGAAAAAAGAACATTTTACTTATCGCCGTGCTCAGTGCTGCTGCAGGTCTCAT
TTTCATAATTATTGTAGTTCTCTTGTGTATTTGCAGAGCAAGATTGAGATGTTGCTGT
TGTGCTCCTGCTCCTGCTCCATGCCTTGACGATCCTTTCCCGCAAATTGCACAACTTG
CAAGTGGACCTCGAATATTCACGTACAGAGAACTAAGTGATGCAACAAAGGGGTTC
AGTGAGAATGAGTTGCTAGGGCAGGGGGGATTTGGCAAGGTCTTTCGTGGAGTGCT
GAGGAGTGGAACCATGATAGCCGTGAAAAAAATTTCAGAAGGCTCAGATCAAGGCG
AACAGCAGTTTGTAGCGGAAGTGTCGATTATTAGCAATATCCGGCATCGCAGCGTGG
TCCAGTTACAAGGCTGGTGCCACGAACAAGGTCAGCTCATACTTGTTTACGATTACA
TGCCGAACGGTGGCCTGGATCAGCACCTCTACGCAAGTAATTGTCCCCTCAATTGGA
CCATGCGTTACAATGTCATCGTAGATCTTGCATCTGCTCTCGCCTATCTGCACGAAA
AGCTGGAGCAATGCGTGATCCACCGTGACATTAAAGCAAGCAATGTGATGCTTGAC
AGGGACTTCAAAGGGCGATTGGGTGACTTTGGACTTGCAAAATCATCAGCTCGCGAT
ATGGTGGCTGCAACTACCAAGCTGGCTGGAACCATGGTATACATGGCACCTGAACTT
CCTATCACGTTTAAACCCACCACGGAGAGTGACGTATACAGTTTTGGAATACTGGCA
CTGGAGGTTATATGCCGAAGGCGGCCTTTCGACGGGACTGTTATACTGTTAGACTGG
GTGTGGGAGAAGCATGAGCAAGGAGAGCTTCTACAGGTTGTAGACCCTGGTTTGAA
CCAAGCTTTCGATCGTACTCAAGCTCAGGTTGCATTGTCCGTTGCGCTGATGTGTGCC
AATCCCAATCCTAATGAACGTCTTCGGATGCAGATGGCCCGTCAAATGTTGATAGGA
GAAGTGTCGGTGCCTCCTCTCCCTGCTAACAGACCATTCATGCTGTATTCAAATGTG
AATTCCGAACAAGGATCGTGTAACAACTCAGGATTTCATTCTGACGCTTGGAATACA
GCCGCAATAGAAAATGGAAGAGTGACAATTATACAGAGACCCGAGATGAATCCGAG
A

FIGURE 2

Deduced amino acid sequence of the LLPK-1 from *Physcomitrella patens* (SEQ ID NO:2)

MQINNGFLHLVSTLLGLLHLATFATAELKTIEFSFPNFKSPENDGTINIPNATDVPSGRNV
LFLPKEKNAMSVGWVIYEEKVQFWDNSDDAASFSTEFTFSTSGYNASTGGSGLAFLITP
DFSIGDIRGYLGIFSSTTNASTNNQKIAVEIDVFKNPWDPSASHIGLDVNSIESVKVKDYC
PVMDNRCTYFTNKGDINVWIDYMAESETLEVRLAMGSSSVKPTQPDLQFIGLNLPRTIR
NFMYVGFSAATGSDFYPAHTFRLRRWSFKTTAPSNGKKNILLIAVLSAAAGLIFIIIVVLL
CICRARLRCCCCAPAPAPCLDDPFPQIAQLASGPRIFTYRELSDATKGFSENELLGQGGFG
KVFRGVLRSGTMIAVKKISEGSDQGEQQFVAEVSIISNIRHRSVVQLQGWCHEQGQLILV
YDYMPNGGLDQHLYASNCPLNWTMRYNVIVDLASALAYLHEKLEQCVIHRDIKASNV
MLDRDFKGRLGDFGLAKSSARDMVAATTKLAGTMVYMAPELPITFKPTTESDVYSFGIL
ALEVICRRRPFDGTVILLDWVWEKHEQGELLQVVDPGLNQAFDRTQAQVALSVALMCA
NPNPNERLRMQMARQMLIGEVSVPPLPANRPFMLYSNVNSEQGSCNNSGFHSDAWNTA
AIENGRVTIIQRPEMNPR

FIGURE 3

```
                    1                                                                         75
SEQIDNO:2    (1)    ---------------------------------------------------------------------------
SEQIDNO:12   (1)    ---------------------------------------------------------------------------
SEQIDNO:13   (1)    ---------------------------------------------------------------------------
SEQIDNO:14   (1)    MRISSEEIVRCLTEQTKEQLGSLHVSLAVSLSDKDRKGIEDYAEDSCSLASYMIRVKPGLLPVQPSPKHLCTFWHL
SEQIDNO:15   (1)    ---------------------------------------------------------------------------
SEQIDNO:16   (1)    ---------------------------------------------------------------------------
SEQIDNO:17   (1)

76                                                                        150
SEQIDNO:2    (1)    --------MQINNGFLHLVSTLLGLLHLATFATAELKTIEFSFPNFKSPENDGTINIPNATDVPSGRNVLFLPKEK
SEQIDNO:12   (1)    --------MRSRTKYTCLLALYFSLSLKIAHVNPLSFKLNFTESNHNG-----SATIQLQEDAFYNKAVKLTKDEL
SEQIDNO:13   (1)    ---------MGNHRLLLLLLLLLAVVGSDHGGVLAADE-FTYNGFG------GANLTLDGMAAVAPNGLLVLSNG
SEQIDNO:14   (76)   NSLVLHKLHMENQPVLFSAVFILYVSFLGPFCASSGEESFVYSGFASTG----AANLTLDGSAMVTTTGLLQLTDS
SEQIDNO:15   (1)    --------MSLSRKLLVIFFTWITALSMSKPIFVSSDNMNFTFKSFTIR------NLTFLGDSHLRNGVVGLTREL
SEQIDNO:16   (1)    ---------------MANSILLFSFVLVLPFVCSVQFNISRFGSDVS--------EIAYQGDARANGAVELTNIDY
SEQIDNO:17   (76)       M M N  LLLLALLIS VLLS  V ALS  I FTFS  F         ANITL GDA V  AVLLL   E 151                                                                       225
SEQIDNO:2    (69)   N----AMSVGNVIYEEKVQFWD--NSDDAASFSTEFTFSTSGYNASTGGSGLAFLITPDFS-------IGDIRGYLGI
SEQIDNO:12   (64)   NGKITQSVGRAIYTDPVPLWD-STTGQLASFTTRFTFKIYAP-TNDSSYGEGLAFFLSSYPSVVPNNSMDGYLGL
SEQIDNO:13   (60)   ---TNQMAGHAFHPTPIRLRGGAAGGAVQSFSAAFVFAIVSNFTVLSDNGMAFVVAPSTR---LSTFNAGQYLGI
SEQIDNO:14   (148)  ---MPNIQGHAFYPTPLRFKK-QSNGIVQSFSVAFMFGIISPYSDASTDGMAFVVAPNKG---FPDAKAAQFLGL
SEQIDNO:15   (63)   G-VPDTSSGTVIYNNPIRFYD-PDSNTTASFSTHFSFTVQNLNPDPTSAGDGLAFFLSHDN--DTLGSPGGYLGL
SEQIDNO:16   (54)   ----TCRAGWATYGKQVPLWN-PGTSKPSDFSTRFSFRIDTRNVGYGNYGHGFAFFLAPARIQLPPNSAGGFLGL
SEQIDNO:17   (151)       QSAG AIY  PVRLWD    SG VASFST FSF I S  NT  SS CMAFAFFPS       LP GSAGGYLGL 226                                                                       300
SEQIDNO:2    (134)  FSSTTNASTN-NQKIAVEIDVFKN-PWDPSAS--HIGLDVNSIESVKVKDYCP--------VMDNRCTYFTNKGDI
SEQIDNO:12   (137)  FSNSNDQSDPLNQIVAVEFDSHKN-TWDPDG--NHVGINIHSIVSVAN--------------VTWRSSINDGRIA
SEQIDNO:13   (129)  LNVTDNGNA-DNNIFAVELDTMLNPEFQDMNS-NHIGVDINSMKSVQN--HSAGYYDEATGAFNNLSLISR--QPM
SEQIDNO:14   (216)  LNISSDNST-SNHMFAVEIDTAQNTELDDIDG-YHVGIDINSLHSKKSQHIGFYNDQHGGLLKNLTLTGSNCKPV
SEQIDNO:15   (134)  VNSSQPMKN---RFVAIEFDTKLDPHFNDPNG-NHIGLDVDSLNSIST-------SDP--LLSSQIDLKSGKSI
SEQIDNO:16   (124)  FNGTNNQSS-AFPLVYVEFDTFTNPEWDPLDVKSHVGINNNSLVSSNY--------------TSWNATSHNQDIG
SEQIDNO:17   (226)  FN SNNQST  NQIVAVEFDT NPEWDPI     NHIGIDINSL SV                   L N  LT  N K I 301                                                                       375
SEQIDNO:2    (198)  NVWIDYMAESETLEVRLAMGSSSVKPT--QPDLQFIGLNLPRTIRNFMYVGFSAATGSDFYPAHTFRLRRWSFKT
SEQIDNO:12   (195)  NAWVTYQANSRNLSVFLSYQDNPQFSG-----NSSLSYSVDLSKYLPDKVSIGFSASTGKFVELHQILYWEFDS---T
SEQIDNO:13   (199)  QVWVDYDGATTVLNVTMAPLDVPKPS----KPLISAPVNLSSVVTDTAYVGFSAATGVIYTRHYVLGWSFSQNGA
SEQIDNO:14   (289)  QVWVDYDGETTQINVTLAPIKVTKPT----RPLLSVPFNLSTVLTDQAYIGFSAATGPLTSHYYVLGWSFAMNAP
SEQIDNO:15   (195)  TSWIDYKNDLRLLNVFLSYTDPVTTTKKPEKPLLSVNIDLSPFLNGEMYVGFSGSTEGSTEIHLIENWSFKTSGF
SEQIDNO:16   (184)  RVLIFYDSARRNLSVSWTYDLTSDPLE---NSSLSYIIDLSKVLPSEVTIGFSATSGGVTEGNRLLSWEFSSSLE
SEQIDNO:17   (301)  NVWIDYDAESRNLNVTLAY D S PS     KPLLSV INLSKVL D MYIGFSAATG ITE HYIL WSFSS G 376                                                                       450
SEQIDNO:2    (271)  TAPSNGKKNILLIAVLSAAAGL-----------------IFIIIVVLLCICRARLRCCCCAPAPAPCLDDPFPQIA
SEQIDNO:12   (265)  DVHLMKTEKTKGILVISLSTSGSVVV----------CSIGLVCFFLCFRRIRRTTRSREKEKEKLDCDESIDSEF
SEQIDNO:13   (270)  APSLHTSSLPALPRFGPKPRSK----------------VLEIVLPIATAAFVLALVIAAFLFVRRRVRYAEVREDW
SEQIDNO:14   (360)  APPLEISRLPRLPCPGDNRLQK----------------ILQILLPIVAVALIF---IVVMILVRRQQRYAELREDW
SEQIDNO:15   (270)  LPVRSKSNHLHNVSDSSVVNDDPVVIPSKKRRHRHNLAIGLGISCPVLICLALFVFGYFTLKKWKSVKAEKELKT
SEQIDNO:16   (256)  LIDIKKSQNDKKGMIIGISVSG---------------FVLLTFFITSLIVFLKRKQQKKKAEETENLTSINEDL
SEQIDNO:17   (376)     P I KS    KLI VISIS  S             I  ILI IL  I I             RR    AEI EDW 451                                                                       525
SEQIDNO:2    (330)  QLASGPRIFTYRELSDATKGFSENELLGQGGFGKVFRGVLRSG-TMIAVKKISEGSDQGEQQFVAEVSIISNIRH
SEQIDNO:12   (330)  EKGKGPRRFQYNELVVATDNFAAERKLGEGGFGAVYQGFLKDQNIEIAIKRVAKGSTQGRKEYISEVKIISRLRH
SEQIDNO:13   (330)  EVEFGPHRFSYKELYQATKGFKNKQLLGTGGFGRVYKGVLAKSNLEIAVKRVSHDSKQGMKEFIAEVVSIGHLRH
SEQIDNO:14   (417)  EVEFGPHRFSYKDLFNATEGFKSKHILGVGGFGKVYKGVLRTSKLEVAVKKVSHGSNQCMKEFISEVVSIGHLRH
SEQIDNO:15   (345)  ELITGLREFSYKELYTATKGFHSSRVIGRGAFGNVYRAMFVSSGTISAVKRSRHNSTEGKTEFLAELSIIACLRH
SEQIDNO:16   (315)  ERGAGPRKFTYKDLASAANNFADDRKLGEGGFGAVYRGYLNSLDMMVAIKKFACCSKQGKREFVTEVKIISSLRH
SEQIDNO:17   (451)  ELG GPRRFSYKELY ATKGFAS  RLLG GGFGKVYRGVLRSS  LEIAVKKVSHGS QGKKEFIAEV IIS LRH
```

FIGURE 3
(continued)

```
                526                                                                           600
SEQIDNO:2   (404) RSVVQLQGWCHEQGQLILVYDYMPNGGLDQHLY----ASNCPLNWTMRYNVIVDLASALAYLHEKLEQCVIHRDI
SEQIDNO:12  (405) RNLVQLVGWCHEHGEFLLVYEFMPNRSLDKHLY----DGGNLLAWPLRFKITIGVASALLYLHEEWEQCVVHRDV
SEQIDNO:13  (405) RNLVQLLGYCRRKGELLLVYDYMSNGSLDKYLY---DKTKPVLDNGQRFQIIKGVASGLLYLHEDWEQVVIHRDI
SEQIDNO:14  (492) RNLVQLLGYCRRKGELLLVYDYMPNGSLDKYLYG--EDNKPVLNWAQRMQIIKDVASGLFYLHEKWDKVVIHRDI
SEQIDNO:15  (420) KNLVQLQGWCNEKGELLLVYEFMPNGSLDKILYQESQTGAVALDWSHRLNIAIGLASALSYLHHECEQQVVHRDI
SEQIDNO:16  (390) RNLVQLIGWCHEKDEFLMIYEFMPNGSLDAHLF----GKKPHLAWHVRCKITLGLASALLYLHEEWEQCVVHRDI
SEQIDNO:17  (526) RNLVQLLGWCHEKGELLLVYDFMPNGSLDKHLY    KPVL W LRFNIIIGLASALLYLHEEWEQCVIHRDI 601                                                                               675
SEQIDNO:2   (475) KASNVMLDRDFKGRLGDFGLAKSSARDMVAATTKLAGTMVYMAPELPITFKPTTESDVYSFGILALEVICRRRPF
SEQIDNO:12  (476) KPSNVMLDSGFNAKLGDFGLARLVDHDRGSQTTVIAGTMGYMAPECVTTGKASKETDVYSFGILALEIACGRRPV
SEQIDNO:13  (477) KASNVLLDGEMNGRLGDFGLARLYDHGVDPQTTHVVGTMGYLAPELVRTGKATPVTDVFAFGVFVLEVTCGRRPL
SEQIDNO:14  (565) KASNVLLDSEMNARLGDFGLARLYEHGTNPQTTHLVGTMGFIAPELARTGKASPLTDVFAFGTFLLEVTCGRWPI
SEQIDNO:15  (495) KTSNIMLDINFNARLGDFGLARLTEHDKSPVSTLTAGTMGYLAPEYLQYGTATEKTDAFSYGVVILEVACGRRPI
SEQIDNO:16  (461) KASNVMLDSNFNAKLGDFGLARLMDHELGPQTTGLAGTFGYMAPEYISTGRASKESDVYSFGVVTLEIVTGRKSV
SEQIDNO:17  (601) KASNVMLDSEFNARLGDFGLARL DHDL PQTT LAGTMGYMAPELV TGKAS ETDVFSFGVLILEV CGRRPI 676                                                                           750
SEQIDNO:2   (550) DGTVI-------LLDWVWEKHEQGELLQVVDPGLNQ-AFDRTQAQVALSVALMCANPNPNERLRMQMARQMLIGE
SEQIDNO:12  (551) VPKED--NDRISLVQWVWDLYGRNEILNAIDGRLDG--EFEEREVISLMVVGLWCAHPDYNIRPSIRQVISVLKFE
SEQIDNO:13  (552) GCIAP---DDQNVLLDWVQEHERRHAALDTVDARLCG--KYDADEARLALKLGLMCAHPLPDARPTMRQVTQYLDGD
SEQIDNO:14  (640) SNSAH---HGRKMLVDWVLQHWHQGSLPETVDPKLHG-IYNVDEACLVLTLGLMCSHPIPGARPIMRQVMQYLDGD
SEQIDNO:15  (570) DKEPES-QKTVNLVDWVWRLHSEGRVLEAVDERLKG-EFDEEMMKKLLLVGLKCAHPDSNERPSMRRVLQILNNE
SEQIDNO:16  (536) DRRQGRVEPVTNLVEKMWDLYGKGEVITAIDEKLRIGGFDEKQAECLMIVGLWCAHPDVNTRPSIKQAIQVLNLE
SEQIDNO:17  (676) D          LVDWVWDLH RGELLEAVD RL G  FDEDEA LLLIVGLMCAHPDPN RPSMRQVIQVL GE 751                                                                           825
SEQIDNO:2   (617) VSVPPLPANRPFMLYSNVNSEQGSCNNSGFHSDAWNTAAIENGRVTIIQRPEMNPR----------------
SEQIDNO:12  (623) APLPDLPPKMPVAMYFAPPISLCRFSQSSNGTLKELERPNSYGNTSSSSATNDSCAPPSVRLPEVGY--------
SEQIDNO:13  (624) APMPEVAPTMVSYTHLALMONDGFDSFAMSFPST--------VTSTASPMSADVSAVSGLSGGRIALVTGGNKGV
SEQIDNO:14  (712) APLPEFTPATLNSSLLAIMHNEGVDPYVAQYPWS--------GNSLGTMTPDILSGR----------------
SEQIDNO:15  (643) IEPSPVPRMKPTLSFSCGLSLDDIVSEDEEG----------DSIVYVVS-----------------------
SEQIDNO:16  (611) APVPHLPTKMPVATYHVSSSNTTSVS--SGG ---------ATVTFSSAQHGR--------------------
SEQIDNO:17  (751) APLPELPP MP ASY AIMSNDG  S SS G          G ST S  S      A 826                                                                           900
SEQIDNO:2   (673) ----------------------------------------------------------------------
SEQIDNO:12  (690) ----------------------------------------------------------------------
SEQIDNO:13  (691) GLETCRQLASRCLRVVLTARNEARGLEAVDGIRRSGAADSDVVFHQLDVTDAASVARLADFVRDQFGRLDILINN
SEQIDNO:14  (761) ----------------------------------------------------------------------
SEQIDNO:15  (682) ----------------------------------------------------------------------
SEQIDNO:16  (652) ----------------------------------------------------------------------
SEQIDNO:17  (826)

901                                                                           975
SEQIDNO:2   (673) ----------------------------------------------------------------------
SEQIDNO:12  (690) ----------------------------------------------------------------------
SEQIDNO:13  (766) AGISGVDRDPVLVAKVKDQIFGMDVDQRVEWMRENSKETYDEAKSCITTNYYGAKLVTEALLPLLLLSSSCRIVN
SEQIDNO:14  (761) ----------------------------------------------------------------------
SEQIDNO:15  (682) ----------------------------------------------------------------------
SEQIDNO:16  (652) ----------------------------------------------------------------------
SEQIDNO:17  (901)

976                                                                           1050
SEQIDNO:2   (673) ----------------------------------------------------------------------
SEQIDNO:12  (690) ----------------------------------------------------------------------
SEQIDNO:13  (841) VSSGFGLLRNFNSEDLRKEFDDIDSLTEKRLEELLDLFLDDFKVNLIEAHGWPTGGSSAYKVAKAALNAYTRILA
SEQIDNO:14  (761) ----------------------------------------------------------------------
SEQIDNO:15  (682) ----------------------------------------------------------------------
SEQIDNO:16  (652) ----------------------------------------------------------------------
SEQIDNO:17  (976)
```

FIGURE 3
(continued)

```
              1051                                                                      1125
SEQIDNO:2    (673)  ---------------------------------------------------------------------------
SEQIDNO:12   (690)  ---------------------------------------------------------------------------
SEQIDNO:13   (916)  KKYPTLRINCLTPCYVKTDISMHMGVLTPEEGASNSVKNRNRGTTSSAIALPGTLRSRVAVVTGGNKGIGLEVCR
SEQIDNO:14   (761)  ---------------------------------------------------------------------------
SEQIDNO:15   (682)  ---------------------------------------------------------------------------
SEQIDNO:16   (652)  ---------------------------------------------------------------------------
SEQIDNO:17  (1051)

1126                                                                      1200
SEQIDNO:2    (673)  ---------------------------------------------------------------------------
SEQIDNO:12   (690)  ---------------------------------------------------------------------------
SEQIDNO:13   (991)  QLAADGITVVLTARDETRGVEAAEKLRGMGLSCVIFHHLEVTDSSSVSRLADFLTTRFGKLEILVNNAAVSGMEH
SEQIDNO:14   (761)  ---------------------------------------------------------------------------
SEQIDNO:15   (682)  ---------------------------------------------------------------------------
SEQIDNO:16   (652)  ---------------------------------------------------------------------------
SEQIDNO:17  (1126)

1201                                                                      1275
SEQIDNO:2    (673)  ---------------------------------------------------------------------------
SEQIDNO:12   (690)  ---------------------------------------------------------------------------
SEQIDNO:13  (1066)  AQRVDTNEEQWLVNNEDLRKELDDVDNLTEERLDEVLDSFLKDFEAGALEAHGWPTAPFVAYKMAKVAMNAYTRI
SEQIDNO:14   (761)  ---------------------------------------------------------------------------
SEQIDNO:15   (682)  ---------------------------------------------------------------------------
SEQIDNO:16   (652)  ---------------------------------------------------------------------------
SEQIDNO:17  (1201)

1276                                                            1339
SEQIDNO:2    (673)  ----------------------------------------------------------------
SEQIDNO:12   (690)  ----------------------------------------------------------------
SEQIDNO:13  (1141)  LARRHPELRVNCVHPGYVKTDMTINSGFLTPEEGGRNVVTVALLPDGGPTGAYFDEGREASFLE
SEQIDNO:14   (761)  ----------------------------------------------------------------
SEQIDNO:15   (682)  ----------------------------------------------------------------
SEQIDNO:16   (652)  ----------------------------------------------------------------
SEQIDNO:17  (1276)
```

FIGURE 4

```
              1                                                                          75
SEQIDNO:2   (1)   ---MQINNGFLHLVSTLLGLLHLATFATAELKTIEFSFPNFKSPENDGTINIPNATDVPSGRNVLFLPKEKNAMS
SEQIDNO:18  (1)   ---MSLSRKLLVIFFTWITALSMSKPIFVSSDNMNFTFKSFTIR----NLTFLGDSHLRNGVVGLTRELGVPDTS
SEQIDNO:19  (1)   MGIARSINSFMFFFFLMILSNASKSSVLAEATTAKFTFIGFKENQ--TDIQTEGASTIQHDNDLLRLTNRKQN-V
SEQIDNO:20  (1)   ----------MLVLFLLLTIPTRAQRTTTETPKTEFIFRGFSGNQ--SNIVTTGAATIKLDG-LLRLTDRNSN-V
SEQIDNO:21  (1)   --------MFVKLKLIFFFFLLCQIMISSSQNLNFTYNGFHPPL--TDISLQGLATVTPNG-LLKLTNTSVQ-K
SEQIDNO:22  (1)   -MLFPWRSLVLIAFTSLVVQLIPAQAVEDRRHDTTFLFDGFNG----TNLILEANASVIGSESVLSLTNHSHEFM
SEQIDNO:23  (1)             LLVIFFLLI   L LAQ V AES   I FTF GF       TNI L GAATV       LLRLTN      N V 76                                                                         150
SEQIDNO:2   (73)  VGWVIYEEKVQFWDN-----SDDAASFSTEFTFSTSGYN--ASTGGSGLAFLITPDFSIGDIR--GYLGIFSSTT
SEQIDNO:18  (69)  SGTVIYNNPIRFYDP·······DSNTTASFSTHFSFTVQNLNPDPTSAGDGLAFFLSHDNDTLGSP-GGYLGLVNSSQ
SEQIDNO:19  (73)  TGTAFYRKPIRLREL-TNSSDIKVCSFSTSFVFVILPS--SPGNGGFGFTFTLSPTPNRPGAESAQYLGLLNRTN
SEQIDNO:20  (62)  TGTSFYHKPVRLLETNTSSTNSTIRSFSTSFVFVIIPT--SSSNCGGFGFTFTLSPTPDRTGAESAQYLGLLNKAN
SEQIDNO:21  (63)  TGHAFCTERIRFKDS----QNGNVSSFSTTFVFAIHSQ--IFTLSGHGIAFVVAPTLGLPFALPSQYIGLFNISN
SEQIDNO:22  (71)  LGRALYAAPVQMKNN-----HTVSSFSTTFVFSIVPP--PSNEGGHGLAFIMTPYTSPMGAQPVQYLGLLNLTS
SEQIDNO:23  (76)  TGTAFY  PIRFKD        TVASFSTSFVFSIIP   PS CG  GLAFILSPT     CA   AQYLCLLN  TN 151                                                                        225
SEQIDNO:2   (139) NASTNNQKIAVEIDVFK----NPWDPSASHIGLDVNSIESVKVKDYCPVMDNR······CTYFTNKG-DINVWIDYMA
SEQIDNO:18  (139) --PMKNRFVAIEFDTKL-DPHFNDPNGNHIGLDVDSLNSISTSDPLLSSQID--------LKSGKSITSWIDYKN
SEQIDNO:19  (145) NGNPSNHVFAVEFDTVQGFKDGADRRGNHIGLNFNNLSSNVQEPLIYYDTED--RKEDFQLESGEPIRVLIDYDG
SEQIDNO:20  (135) DGNSTNHVFAVEFDTVQGFKDGADRTGNHIGLNFNSLTSDVQEPVVYYDNEDPNRKEDFPLQSGDPIRAILDYDG
SEQIDNO:21  (132) NGNDTNHIFAVEFDTIQ-SSEFGDPNDNHVGIDLNGLRSANYSTAGYRDDHD--KFQNLSLISRKRIQVWIDYDN
SEQIDNO:22  (138) NGQPYNHLFAVEFDTIM-NVEFKDPDRNHVGVDINSLISVQTETAGYWNGEE---FHELNLRSGRNIQAWIDYDH
SEQIDNO:23  (151) NCN  TNHVFAVEFDTIQ   DFADP CNHIGLDVNSL SV   E  IYYD ED  R  DF L  SGK IQVWIDYDG 226                                                                        300
SEQIDNO:2   (206) ESETLEVRLAMGSSSVK----PTQPDLQFIGLNLPRTIRNFMYVGFSAATGSDFYPAHTFRLRRWSFKTTAPS---
SEQIDNO:18  (203) DLRLLNVFLSYTDPVTTTKKPEKPLLS-VNIDLSPFLNGEMYVGFSGSTE-GSTEIHLIENWSFKTSGFLPVRSK
SEQIDNO:19  (218) SSETLNVTIYPTRLEFK---PKKPLISRRVSELSEIVKDEMYVGFTAATGKDQSSAHYVMGWSFSSCGENPM---
SEQIDNO:20  (210) PTQTLNLTVYPANLKSR---PVRPLISRPVPKLSQIVQEEMYVGFTAATGRDQSSAHYVMGWSFSSGGDLLT----
SEQIDNO:21  (204) RSHRIDVTVAPFDSDK----PRKPLVS-YVRDLSSILLEDMYVGFSSATG-SVLSEHFLVGWSFRLNGEAPM---
SEQIDNO:22  (209) LESSLNVTITVAGLPR----PQRPLIS-LQIDLQNIVEEKMLVGFSAATG-LLVEDHYILAWSFTTEDTAPP---
SEQIDNO:23  (226)    S TLNVTIAPA L  K      P KPLIS IVIDLS IV  EEMYVGFSAATG  D SSAHYIMGWSFSS  GEAPM 301                                                                        375
SEQIDNO:2   (275) ·······NGKKNILLIAVLSAAAG·······LIF·IIIVVLLCICRARLRCCCCAPAPAFCLDDPFPQIAQLASG
SEQIDNO:18  (276) SNHLHNVSDSSVVNDDPVVIPSK-KRRHRHNLAIGLGISCPVLICLALFVFGYFTLKKWKSVKAEKELKTELITG
SEQIDNO:19  (287) --------ADWLEISRLP-PPPRLSNKKGYNSQVIVLIVALSIVTLVLLVLLFIFVMYKRRIQEEDTLEDWEIDYP
SEQIDNO:20  (279) -------EDTLDLLELPRPPPNTAKKRGYNSQVLALIVALSGVTVILLALLFFFVMYKKRLQQGRVLEDWEINHP
SEQIDNO:21  (270) -------LSLSKLPKLPRFEPRR------ISEFYKIGMPLISLSLIFSIIFLAFYIVRRKKKYEEELDDWETEFG
SEQIDNO:22  (275) --------LDVSCLSSFANMYSEP--------LSRGFIAGVTVVSVVLFWLVIAAAMFLRRTLNRETVEEWEQEYW
SEQIDNO:23  (301)         D S L  LP L P      KR    SLVIGLIIALSVVSLILLILL   F MYKRR L EE LEDWEIEYG 376                                                                        450
SEQIDNO:2   (335) PRIFTYRELSDATKGFSENELLGQGGFGKVFRGVLRS--GTMIAVKKISEGSDQGEQQFVAEVSIISNIRHRSVV
SEQIDNO:18  (350) LREFSYKELYTATKGFHSSRVIGRGAFGNVYRAMFVS-SGTISAVKSRHNSTEGKTEFLAELSIIACLRHKNLV
SEQIDNO:19  (354) -HRFRYRDLYLATKKFKESEIIGTGGFGIVYRGNLSS--SGPIAVKKITSNSLQGVREFMAEIESLGRLGHKNLV
SEQIDNO:20  (347) -HRLRYKDLYAATDGFKENRIVGTGGFGTVFRGNLSSPSSDQIAVKKITPNSMQGVREFTAEIESLGRLRHKNLV
SEQIDNO:21  (332) KNRFRFKELYHATKGFKEKDLLGSGGFGRVYRGILPT-TKLEVAVKRVSHDSKQGMKEFVAEIVSIGRMSHRNLV
SEQIDNO:22  (335) PHRFDYKELRIATRGFRDENLLGYGGFGMVYKGFLPR-SGQEVAVKCITTEFKEGIKGFVAEISSMGRLQHRNLV
SEQIDNO:23  (376)   HRFRYKELY ATKGFKE ELLGTGGFGFG VYRGIL S  SG    IAVKKIT NS  QGVREFVAEISSIGRLRHKNLV 451                                                                        525
SEQIDNO:2   (408) QLQGWCHEQGQLILVYDYMPNGGLDQHLYASNCP----LNWTMRYNVIVDLASALAYLHEKLEQCVIHRDIKASN
SEQIDNO:18  (424) QLQGWCNEKGELLLVYEFMPNGSLDKILYQESQTGAVALDWSHRLNIAIGLASALSYLHHECEQQVVHRDIKTSN
SEQIDNO:19  (426) NLQGWCKHKNELLLIYDYIPNGSLDSLLYQTPRRNGIVLPWDVRFEIIKGIASGLLYLHEEWEQIVVHRDVKPSN
SEQIDNO:20  (421) NLQGWCKQKNDLLLIYDYIPNGSLDSLLYSRPRQSGVVLSWNARFKIAKCIASCLLYLHEEWEKVVIHRDIKPSN
SEQIDNO:21  (406) PLLGYCRRRGELLLVYDYMPNGSLDKYLYNNPE---TTLDWKQRSTIIKGVASGLFYLHEEWEQVVIHRDVKASN
SEQIDNO:22  (409) QLRGWCRRHTQLFIVYDYMPNGSLHKLIFGSPT---TVLPWHRRYAILKGVAAGLLYLHEQWEKRVVHRDIKSSN
SEQIDNO:23  (451) QLQGWCK  KGELLLVYDYMPNGSLDKLLYQSP    GVVL W  RF IIKGIASGLLYLHEEWEQVVIHRDIKASN
```

FIGURE 4
(continued)

```
            526                                                                         600
SEQIDNO:2  (479) VMLDRDFKGRLGDFGLAKSSARDMVAATTKLAGTMVYMAPELPITFKPTTESDVYSFCILALEVICRRRP--------
SEQIDNO:18 (499) IMLDINFNARLGDFGLARLTEHDKSPVSTLTAGTMGYLAPEYLQYGTATEKTDAFSYGVVILEVACGRRPIDKEP
SEQIDNO:19 (501) VLIDEDMNAKLGDFGLARLYERGTLTQTTKIVGTLGYMAPELTRNGKGSTASDVFAFGVLLLEIVCGNK-----P
SEQIDNO:20 (496) VLIEDDMNPRLGDFGLARLYERCSQSNTTVVVGTIGYMAPELARNGKSSSASDVFAFGVLLLEIVSGRR-----P
SEQIDNO:21 (478) VLLDADFNGRLGDFGLARLYDHGSDPQTTHVVGTLGYLAPEHSRTGRATTTTDVYAFGAFLLEVVSGRRPIEFHS
SEQIDNO:22 (481) VLLDSEFNGRLSDFGLARLYDHSENPETTYVVGTLGYIAPELIQTGKATPSSDVFSFGVLLLEVACGKSP-VDSL
SEQIDNO:23 (526) VLLD DFNGRLGDFGLARLYERGS  PQTT VVGTLGYMAPEL RTGKATTASDVFAFGVLLLEVVCGRRP       P 601                                                                         675
SEQIDNO:2  (549) -FDGTVILLDWVWEKHEQGELLQVVDPGLN--QAFDRTQAQVALSVALMCANPNPNERLRMQMARQMLIGEVSVP
SEQIDNO:18 (574) ESQKTVNLVDWVWRLHSEGRVLEAVDERLKG--EFDEEMMKKLLLVGLKCAHPDSNERPSMRRVLQILNNEIEPS
SEQIDNO:19 (571) TNAENFFLADWVMEFHTNGGILCVVDQNLG--SSFNGREAKLALVVGLLCCHQKPKFRPSMRMVLRYLNGEE---
SEQIDNO:20 (566) TDSGTFFLADWVMELHARGEILHAVDPRLG--FGYDGVEARLALVVGLLCCHQRPTSRPSMRTVLRYLNGDD---
SEQIDNO:21 (553) ASDDTFLLVEWVFSLWLRGNIMEAKDPKLGS-SGYDLEEVEMVLKLGLLCSHSDPRARPSMRQVLQYLRGDM---
SEQIDNO:22 (555) EDSERMILVEWAWELYTEGRLLEASDPKLAAKGGYDEGEMEKVLKLGLLCSHPEPESRLSMRQVCQVLNGEA---
SEQIDNO:23 (601)    SETFILVDWVWELHT G ILEAVDPKLG   GFD  EAKLALVVGLLCAHPDP SRPSMR VLQYLNGEI 676                                                729
SEQIDNO:2  (621) PLPANRPFMLYSNVNS-EQGSCNNSGFHSDAWNTAAIENGRVTIIQRPEMNPR-
SEQIDNO:18 (647) PVPKMKPTLSFSCGLSLDDIVSEDEEGDSIVYVVS-------------------
SEQIDNO:19 (641) NVPQIDENWGFSDSSR-DDHKSNVVGYVSSDRASSSNTFSSFSNVSSSSIVSGR
SEQIDNO:20 (636) DVPEIDNDWGYSDSSR-SDLGSNFEGYVSSDRASSSVPSFSVTRVSSSSVISGR
SEQIDNO:21 (624) ALPELTPLDLSAGSVMNLGGRDGFSGIAMTDFSTVFKGFTGGSSIADSLLSGGR
SEQIDNO:22 (627) PVPCRW------------------------------------------------
SEQIDNO:23 (676) PVP I P    FS S    DD  SN  GY SSDFASSS    S IS S  I  GR
```

Figure 5

Table 7

| Genotype | Well- | Watered | Cycling | Drought |
|---|---|---|---|---|
|  | Mean DW (mg) | DW standard error (mg) | Mean DW (mg) | DW standard error (mg) |
| PpLLPK-1 | 32.0 | 2.3 | 24.0 | 1.3 |
| Wild-type control | 25.5 | 2.1 | 19.3 | 1.1 |

Figure 6

SEQ ID NO: 8 - promoter sequence for constitutive expression aatccgaaaagtttctgcaccgttttcaccccctaactaacaatatagggaacgtgtgctaaatataaaatgagaccttata
tatgtagcgctgataactagaactatgcaagaaaaactcatccacctactttagtggcaatcgggctaaataaaaaagag
tcgctacactagtttcgttttccttagtaattaagtgggaaaatgaaatcattattgcttagaatatacgttcacatctctgtcatg
aagttaaattattcgaggtagccataattgtcatcaaactcttcttgaataaaaaaatctttctagctgaactcaatgggtaaa
gagagagatttttttaaaaaaatagaatgaagatattctgaacgtattggcaaagatttaaacatataattatataattttata
gtttgtgcattcgtcatatcgcacatcattaaggacatgtcttactccatcccaattttatttagtaattaaagacaattgacttat
ttttattatttatctttttcgattagatgcaaggtacttacgcacacactttgtgctcatgtgcatgtgtgagtgcacctcctcaata
cacgttcaactagcaacacatctctaatatcactcgcctatttaatacatttaggtagcaatatctgaattcaagcactccac
catcaccagaccacttttaataatatctaaaatacaaaaaataattttacagaatagcatgaaaagtatgaaacgaactat
ttaggttttcacatacaaaaaaaaaaagaattttgctcgtgcgcgagcgccaatctcccatattgggcacacaggcaac
aacagagtggctgcccacagaacaacccacaaaaaacgatgatctaacggaggacagcaagtccgcaacaacctttt
taacagcaggctttgcggccaggagagaggaggagaggcaaagaaaaccaagcatcctccttctcccatctataaatt
cctccccccttttcccctctctatataggaggcatccaagccaagaagagggagagcaccaaggacacgcgactagca
gaagccgagcgaccgccttctcgatccatatcttccggtcgagttcttggtcgatctcttccctcctccacctcctcctcacag
ggtatgtgcctcccttcggttgttcttggatttattgttctaggttgtgtagtacgggcgttgatgttaggaaaggggatctgtatct
gtgatgattcctgttcttggatttgggatagaggggttcttgatgttgcatgttatcggttcggtttgattagtagtatggttttcaat
cgtctggagagctctatggaaatgaaatggtttagggatcggaatcttgcgattttgtgagtaccttttgtttgaggtaaaatca
gagcaccggtgattttgcttggtgtaataaagtacggttgtttggtcctcgattctggtagtgatgcttctcgatttgacgaagct
atcctttgtttattccctattgaacaaaaataatccaactttgaagacggtcccgttgatgagattgaatgattgattcttaagcc
tgtccaaaatttcgcagctggcttgtttagatacagtagtccccatcacgaaattcatggaaacagttataatcctcaggaa
caggggattccctgttcttccgatttgctttagtcccagaatttttttcccaaatatcttaaaaagtcactttctggttcagttcaat
gaattgattgctacaaataatgcttttatagcgttatcctagctgtagttcagttaataggtaatacccctatagtttagtcagga
gaagaacttatccgatttctgatctccatttttaattatatgaaatgaactgtagcataagcagtattcatttggattatttttttatt
agctctcaccccttcattattctgagctgaaagtctggcatgaactgtcctcaattttgttttcaaattcacatcgattatctatgc
attatcctcttgtatctacctgtagaagtttcttttggttattccttgactgcttgattacagaaagaaatttatgaagctgtaatcg
ggatagttatactgcttgttcttatgattcatttcctttgtgcagttcttggtgtagcttgccactttcaccagcaaagttc

SEQUENCE LISTING

```
<160> NUMBER OF SEQ ID NOS: 23

<210> SEQ ID NO 1
<211> LENGTH: 2049
<212> TYPE: DNA
<213> ORGANISM: Physcomitrella patens

<400> SEQUENCE: 1
tttctaagct attcaacctg gattgatttc agtatgcaga ttaacaacgg tttcttgcac      60
ttggtgtcta ccctcctagg tttacttcat ttagcaactt ttgccacagc tgaattgaaa     120
actattgaat ttagttttcc taattttaag agtccggaga atgatggtac aatcaacatt     180
ccgaatgcaa cagatgtgcc tagtggtagg aacgtcctct tccttcccaa ggaaaagaac     240
gccatgagtg ttgggtgggt tatttatgaa gagaaagttc aattctggga caactccgat     300
gacgctgctt cttttagtac agagtttacc ttcagtactt caggttacaa tgcgtcaacc     360
ggaggtagcg gacttgcatt cttgataact ccagattttt ccatcggtga cattcgtgga     420
taccttggga tattttcatc gacaaccaac gcctccacaa acaatcaaaa gattgcagtg     480
gagattgatg ttttcaagaa cccatgggat ccaagcgcca gccacattgg cttagacgta     540
```

```
aactccatcg aatccgtgaa ggtaaaagac tattgtccgg tgatggataa ccgttgcact      600
tactttacca acaaagggga catcaatgtt tggattgact acatggctga agtgagact       660 cttgaagtgc gcttagcaat gggttcaagc agtgtgaagc aacccagcc ggatctacaa       720 ttcattggat tgaacttgcc aaggactatc cgaaacttta tgtatgtggg ttttcagca       780 gccactggaa gtgacttta tcctgcacac acatttcgat tacgtcgatg agctttaaa       840 actacggctc cgtccaacgg aaaaagaac attttactta tcgccgtgct cagtgctgct       900
gcaggtctca ttttcataat tattgtagtt ctccttgtgta tttgcagagc aagattgaga    960
tgttgctgtt gtgctcctgc cctgctcca tgccttgacg atcctttccc gcaaattgca      1020
caacttgcaa gtggacctcg aatattcacg tacagagaac taagtgatgc aacaaagggg    1080
ttcagtgaga atgagttgct agggcagggg ggatttggca aggtctttcg tggagtgctg     1140
aggagtggaa ccatgatagc cgtgaaaaaa atttcagaag gctcagatca aggcgaacag    1200
cagtttgtag cggaagtgtc gattattagc aatatccggc atcgcagcgt ggtccagtta    1260
caaggctggt gccacgaaca aggtcagctc atacttgttt acgattacat gccgaacggt    1320
ggcctggatc agcacctcta cgcaagtaat tgtcccctca attggaccat gcgttacaat    1380
gtcatcgtag atcttgcatc tgctctcgcc tatctgcacg aaaagctgga gcaatgcgtg    1440
atccaccgtg acattaaagc aagcaatgtg atgcttgaca gggacttcaa agggcgattg    1500
ggtgactttg acttgcaaa atcatcagct cgcgatatgg tggctgcaac taccaagctg     1560
gctggaacca tggtatacat ggcacctgaa cttcctatca cgtttaaacc caccacggag    1620
agtgacgtat acagtttgg aatactggca ctggaggtta tgccgaag gcggcctttc       1680 gacgggactg ttatactgtt agactgggtg tgggagaagc atgagcaagg agagcttcta    1740
caggttgtag accctggttt gaaccaagct ttcgatcgta ctcaagctca ggttgcattg    1800
tccgttgcgc tgatgtgtgc caatcccaat cctaatgaac gtcttcggat gcagatggcc    1860
cgtcaaatgt tgataggaga agtgtcggtg cctcctctcc ctgctaacag accattcatg    1920
ctgtattcaa atgtgaattc cgaacaagga tcgtgtaaca actcaggatt tcattctgac    1980
gcttggaata cagccgcaat agaaaatgga agagtgacaa ttatacagag acccgagatg    2040
aatccgaga                                                            2049
```

<210> SEQ ID NO 2
<211> LENGTH: 672
<212> TYPE: PRT
<213> ORGANISM: Physcomitrella patens

<400> SEQUENCE: 2

```
Met Gln Ile Asn Asn Gly Phe Leu His Leu Val Ser Thr Leu Leu Gly
1               5                   10                  15

Leu Leu His Leu Ala Thr Phe Ala Thr Ala Glu Leu Lys Thr Ile Glu
            20                  25                  30

Phe Ser Phe Pro Asn Phe Lys Ser Pro Glu Asn Asp Gly Thr Ile Asn
        35                  40                  45

Ile Pro Asn Ala Thr Asp Val Pro Ser Gly Arg Asn Val Leu Phe Leu
    50                  55                  60

Pro Lys Glu Lys Asn Ala Met Ser Val Gly Trp Val Ile Tyr Glu Glu
65                  70                  75                  80

Lys Val Gln Phe Trp Asp Asn Ser Asp Asp Ala Ala Ser Phe Ser Thr
                85                  90                  95
```

```
Glu Phe Thr Phe Ser Thr Ser Gly Tyr Asn Ala Ser Thr Gly Gly Ser
                100                 105                 110

Gly Leu Ala Phe Leu Ile Thr Pro Asp Phe Ser Ile Gly Asp Ile Arg
            115                 120                 125

Gly Tyr Leu Gly Ile Phe Ser Ser Thr Thr Asn Ala Ser Thr Asn Asn
        130                 135                 140

Gln Lys Ile Ala Val Glu Ile Asp Val Phe Lys Asn Pro Trp Asp Pro
145                 150                 155                 160

Ser Ala Ser His Ile Gly Leu Asp Val Asn Ser Ile Glu Ser Val Lys
                165                 170                 175

Val Lys Asp Tyr Cys Pro Val Met Asp Asn Arg Cys Thr Tyr Phe Thr
            180                 185                 190

Asn Lys Gly Asp Ile Asn Val Trp Ile Asp Tyr Met Ala Glu Ser Glu
        195                 200                 205

Thr Leu Glu Val Arg Leu Ala Met Gly Ser Ser Val Lys Pro Thr
210                 215                 220

Gln Pro Asp Leu Gln Phe Ile Gly Leu Asn Leu Pro Arg Thr Ile Arg
225                 230                 235                 240

Asn Phe Met Tyr Val Gly Phe Ser Ala Ala Thr Gly Ser Asp Phe Tyr
                245                 250                 255

Pro Ala His Thr Phe Arg Leu Arg Arg Trp Ser Phe Lys Thr Thr Ala
            260                 265                 270

Pro Ser Asn Gly Lys Lys Asn Ile Leu Leu Ile Ala Val Leu Ser Ala
        275                 280                 285

Ala Ala Gly Leu Ile Phe Ile Ile Val Val Leu Leu Cys Ile Cys
        290                 295                 300

Arg Ala Arg Leu Arg Cys Cys Cys Ala Pro Ala Pro Ala Pro Cys
305                 310                 315                 320

Leu Asp Asp Pro Phe Pro Gln Ile Ala Gln Leu Ala Ser Gly Pro Arg
                325                 330                 335

Ile Phe Thr Tyr Arg Glu Leu Ser Asp Ala Thr Lys Gly Phe Ser Glu
            340                 345                 350

Asn Glu Leu Leu Gly Gln Gly Gly Phe Gly Lys Val Phe Arg Gly Val
        355                 360                 365

Leu Arg Ser Gly Thr Met Ile Ala Val Lys Lys Ile Ser Glu Gly Ser
370                 375                 380

Asp Gln Gly Glu Gln Gln Phe Val Ala Glu Val Ser Ile Ile Ser Asn
385                 390                 395                 400

Ile Arg His Arg Ser Val Val Gln Leu Gln Gly Trp Cys His Glu Gln
                405                 410                 415

Gly Gln Leu Ile Leu Val Tyr Asp Tyr Met Pro Asn Gly Gly Leu Asp
            420                 425                 430

Gln His Leu Tyr Ala Ser Asn Cys Pro Leu Asn Trp Thr Met Arg Tyr
        435                 440                 445

Asn Val Ile Val Asp Leu Ala Ser Ala Leu Ala Tyr Leu His Glu Lys
450                 455                 460

Leu Glu Gln Cys Val Ile His Arg Asp Ile Lys Ala Ser Asn Val Met
465                 470                 475                 480

Leu Asp Arg Asp Phe Lys Gly Arg Leu Gly Asp Phe Gly Leu Ala Lys
                485                 490                 495

Ser Ser Ala Arg Asp Met Val Ala Ala Thr Thr Lys Leu Ala Gly Thr
            500                 505                 510

Met Val Tyr Met Ala Pro Glu Leu Pro Ile Thr Phe Lys Pro Thr Thr
```

-continued

```
            515                 520                 525

Glu Ser Asp Val Tyr Ser Phe Gly Ile Leu Ala Leu Glu Val Ile Cys
    530                 535                 540

Arg Arg Arg Pro Phe Asp Gly Thr Val Ile Leu Leu Asp Trp Val Trp
545                 550                 555                 560

Glu Lys His Glu Gln Gly Glu Leu Leu Gln Val Val Asp Pro Gly Leu
                565                 570                 575

Asn Gln Ala Phe Asp Arg Thr Gln Ala Gln Val Ala Leu Ser Val Ala
            580                 585                 590

Leu Met Cys Ala Asn Pro Asn Pro Asn Glu Arg Leu Arg Met Gln Met
        595                 600                 605

Ala Arg Gln Met Leu Ile Gly Glu Val Ser Val Pro Pro Leu Pro Ala
    610                 615                 620

Asn Arg Pro Phe Met Leu Tyr Ser Asn Val Asn Ser Glu Gln Gly Ser
625                 630                 635                 640

Cys Asn Asn Ser Gly Phe His Ser Asp Ala Trp Asn Thr Ala Ala Ile
                645                 650                 655

Glu Asn Gly Arg Val Thr Ile Ile Gln Arg Pro Glu Met Asn Pro Arg
            660                 665                 670
```

<210> SEQ ID NO 3
<211> LENGTH: 18
<212> TYPE: DNA
<213> ORGANISM: Physcomitrella patens

<400> SEQUENCE: 3
caggaaacag ctatgacc                                          18

<210> SEQ ID NO 4
<211> LENGTH: 19
<212> TYPE: DNA
<213> ORGANISM: Physcomitrella patens

<400> SEQUENCE: 4
ctaaagggaa caaaagctg                                         19

<210> SEQ ID NO 5
<211> LENGTH: 18
<212> TYPE: DNA
<213> ORGANISM: Physcomitrella patens

<400> SEQUENCE: 5
tgtaaaacga cggccagt                                          18

<210> SEQ ID NO 6
<211> LENGTH: 31
<212> TYPE: DNA
<213> ORGANISM: Physcomitrella patens

<400> SEQUENCE: 6
cccgggcacc accagtacct ttgcgtatgt g                           31

<210> SEQ ID NO 7
<211> LENGTH: 30
<212> TYPE: DNA
<213> ORGANISM: Physcomitrella patens

<400> SEQUENCE: 7
gttaacagct caaagtaatc ttgccgttcc                             30

<210> SEQ ID NO 8
<211> LENGTH: 25
<212> TYPE: DNA
<213> ORGANISM: Physcomitrella patens

<400> SEQUENCE: 8
ccgttggacg gagccgtagt tttaa                                          25

<210> SEQ ID NO 9
<211> LENGTH: 25
<212> TYPE: DNA
<213> ORGANISM: Physcomitrella patens

<400> SEQUENCE: 9
agcagcaccg agcacggcga taagt                                          25

<210> SEQ ID NO 10
<211> LENGTH: 26
<212> TYPE: DNA
<213> ORGANISM: Physcomitrella patens

<400> SEQUENCE: 10
ggccgccttc ggcatataac ctccag                                         26

<210> SEQ ID NO 11
<211> LENGTH: 2194
<212> TYPE: DNA
<213> ORGANISM: Oryza sativa

<400> SEQUENCE: 11
aatccgaaaa gtttctgcac cgttttcacc ccctaactaa caatatagggg aacgtgtgct     60 aaatataaaa tgagaccttta tatatgtagc gctgataact agaactatgc aagaaaaact    120
catccaccta ctttagtggc aatcgggcta aataaaaaag agtcgctaca ctagtttcgt    180
tttccttagt aattaagtgg gaaaatgaaa tcattattgc ttagaatata cgttcacatc    240
tctgtcatga agttaaatta ttcgaggtag ccataattgt catcaaactc ttcttgaata    300
aaaaaatctt tctagctgaa ctcaatgggt aaagagagag atttttttta aaaaaataga    360
atgaagatat tctgaacgta ttggcaaaga tttaaacata taattatata attttatagt    420
ttgtgcattc gtcatatcgc acatcattaa ggacatgtct tactccatcc caatttttat    480
ttagtaatta aagacaattg acttattttt attatttatc ttttttcgat tagatgcaag    540
gtacttacgc acacactttg tgctcatgtg catgtgtgag tgcacctcct caatacacgt    600
tcaactagca acacatctct aatatcactc gcctatttaa tacatttagg tagcaatatc    660
tgaattcaag cactccacca tcaccagacc acttttaata atatctaaaa tacaaaaaat    720
aattttacag aatagcatga aaagtatgaa acgaactatt taggttttc acatacaaaa    780 aaaaaagaa ttttgctcgt gcgcgagcgc caatctccca tattgggcac acaggcaaca    840
acagagtggc tgcccacaga acaacccaca aaaacgatg atctaacgga ggacagcaag    900
tccgcaacaa cctttttaaca gcaggctttg cggccaggag agaggaggag aggcaaagaa    960
aaccaagcat cctccttctc ccatctataa attcctcccc ccttttcccc tctctatata   1020
ggaggcatcc aagccaagaa gagggagagc accaaggaca cgcgactagc agaagccgag   1080
cgaccgcctt ctcgatccat atcttccggt cgagttcttg gtcgatctct tccctcctcc   1140
acctcctcct cacagggtat gtgcctccct tcggttgttc ttggatttat tgttctaggt   1200
tgtgtagtac gggcgttgat gttaggaaag gggatctgta tctgtgatga ttcctgttct   1260

```
tggatttggg atagaggggt tcttgatgtt gcatgttatc ggttcggttt gattagtagt    1320
atggttttca atcgtctgga gagctctatg gaaatgaaat ggtttaggga tcggaatctt    1380
gcgattttgt gagtaccttt tgtttgaggt aaaatcagag caccggtgat tttgcttggt    1440
gtaataaagt acggttgttt ggtcctcgat tctggtagtg atgcttctcg atttgacgaa    1500
gctatccttt gttattccc tattgaacaa aaataatcca actttgaaga cggtcccgtt    1560
gatgagattg aatgattgat tcttaagcct gtccaaaatt tcgcagctgg cttgtttaga    1620
tacagtagtc cccatcacga aattcatgga acagttata atcctcagga acaggggatt    1680
ccctgttctt ccgatttgct ttagtcccag aattttttt cccaaatatc ttaaaaagtc    1740
actttctggt tcagttcaat gaattgattg ctacaaataa tgcttttata gcgttatcct    1800
agctgtagtt cagttaatag gtaataccccc tatagtttag tcaggagaag aacttatccg    1860
atttctgatc tccatttta attatatgaa atgaactgta gcataagcag tattcatttg    1920
gattattttt tttattagct ctcaccccctt cattattctg agctgaaagt ctggcatgaa    1980
ctgtcctcaa ttttgttttc aaattcacat cgattatcta tgcattatcc tcttgtatct    2040
acctgtagaa gtttcttttt ggttattcct tgactgcttg attacagaaa gaaatttatg    2100
aagctgtaat cgggatagtt atactgcttg ttcttatgat tcatttcctt tgtgcagttc    2160
ttggtgtagc ttgccacttt caccagcaaa gttc                                2194
```

<210> SEQ ID NO 12
<211> LENGTH: 689
<212> TYPE: PRT
<213> ORGANISM: Oryza sativa

<400> SEQUENCE: 12

```
Met Arg Ser Arg Thr Lys Tyr Thr Cys Leu Leu Ala Leu Tyr Phe Ser
1               5                   10                  15

Leu Ser Leu Lys Ile Ala His Val Asn Pro Leu Ser Phe Lys Leu Asn
            20                  25                  30

Phe Thr Glu Ser Asn His Asn Gly Ser Ala Thr Ile Gln Leu Gln Glu
        35                  40                  45

Asp Ala Phe Tyr Asn Lys Ala Val Lys Leu Thr Lys Asp Glu Leu Asn
    50                  55                  60

Gly Lys Ile Thr Gln Ser Val Gly Arg Ala Ile Tyr Thr Asp Pro Val
65                  70                  75                  80

Pro Leu Trp Asp Ser Thr Thr Gly Gln Leu Ala Ser Phe Thr Thr Arg
                85                  90                  95

Phe Thr Phe Lys Ile Tyr Ala Pro Thr Asn Asp Ser Ser Tyr Gly Glu
            100                 105                 110

Gly Leu Ala Phe Phe Leu Ser Ser Tyr Pro Ser Val Val Pro Asn Asn
        115                 120                 125

Ser Met Asp Gly Tyr Leu Gly Leu Phe Ser Asn Ser Asn Asp Gln Ser
    130                 135                 140

Asp Pro Leu Asn Gln Ile Val Ala Val Glu Phe Asp Ser His Lys Asn
145                 150                 155                 160

Thr Trp Asp Pro Asp Gly Asn His Val Gly Ile Asn Ile His Ser Ile
                165                 170                 175

Val Ser Val Ala Asn Val Thr Trp Arg Ser Ser Ile Asn Asp Gly Arg
            180                 185                 190

Ile Ala Asn Ala Trp Val Thr Tyr Gln Ala Asn Ser Arg Asn Leu Ser
        195                 200                 205
```

-continued

```
Val Phe Leu Ser Tyr Gln Asp Asn Pro Gln Phe Ser Gly Asn Ser Ser
    210                 215                 220

Leu Ser Tyr Ser Val Asp Leu Ser Lys Tyr Leu Pro Asp Lys Val Ser
225                 230                 235                 240

Ile Gly Phe Ser Ala Ser Thr Gly Lys Phe Val Glu Leu His Gln Ile
                245                 250                 255

Leu Tyr Trp Glu Phe Asp Ser Thr Asp Val His Leu Met Lys Thr Glu
            260                 265                 270

Lys Thr Lys Gly Ile Leu Val Ile Ser Leu Ser Thr Ser Gly Ser Val
        275                 280                 285

Val Val Cys Ser Ile Gly Leu Val Cys Phe Phe Leu Cys Phe Arg Arg
    290                 295                 300

Ile Arg Arg Thr Thr Arg Ser Arg Glu Lys Glu Lys Leu Asp
305                 310                 315                 320

Cys Asp Glu Ser Ile Asp Ser Glu Phe Glu Lys Gly Lys Gly Pro Arg
                325                 330                 335

Arg Phe Gln Tyr Asn Glu Leu Val Val Ala Thr Asp Asn Phe Ala Ala
            340                 345                 350

Glu Arg Lys Leu Gly Glu Gly Gly Phe Gly Ala Val Tyr Gln Gly Phe
        355                 360                 365

Leu Lys Asp Gln Asn Ile Glu Ile Ala Ile Lys Arg Val Ala Lys Gly
    370                 375                 380

Ser Thr Gln Gly Arg Lys Glu Tyr Ile Ser Glu Val Lys Ile Ile Ser
385                 390                 395                 400

Arg Leu Arg His Arg Asn Leu Val Gln Leu Val Gly Trp Cys His Glu
                405                 410                 415

His Gly Glu Phe Leu Leu Val Tyr Glu Phe Met Pro Asn Arg Ser Leu
            420                 425                 430

Asp Lys His Leu Tyr Asp Gly Gly Asn Leu Leu Ala Trp Pro Leu Arg
        435                 440                 445

Phe Lys Ile Thr Ile Gly Val Ala Ser Ala Leu Leu Tyr Leu His Glu
    450                 455                 460

Glu Trp Glu Gln Cys Val Val His Arg Asp Val Lys Pro Ser Asn Val
465                 470                 475                 480

Met Leu Asp Ser Gly Phe Asn Ala Lys Leu Gly Asp Phe Gly Leu Ala
                485                 490                 495

Arg Leu Val Asp His Asp Arg Gly Ser Gln Thr Thr Val Ile Ala Gly
            500                 505                 510

Thr Met Gly Tyr Met Ala Pro Glu Cys Val Thr Thr Gly Lys Ala Ser
        515                 520                 525

Lys Glu Thr Asp Val Tyr Ser Phe Gly Ile Leu Ala Leu Glu Ile Ala
    530                 535                 540

Cys Gly Arg Arg Pro Val Val Pro Lys Glu Asp Asn Asp Arg Ile Ser
545                 550                 555                 560

Leu Val Gln Trp Val Trp Asp Leu Tyr Gly Arg Asn Glu Ile Leu Asn
                565                 570                 575

Ala Ile Asp Gly Arg Leu Asp Gly Glu Phe Glu Glu Arg Glu Val Ile
            580                 585                 590

Ser Leu Met Val Val Gly Leu Trp Cys Ala His Pro Asp Tyr Asn Ile
        595                 600                 605

Arg Pro Ser Ile Arg Gln Val Ile Ser Val Leu Lys Phe Glu Ala Pro
    610                 615                 620
```

```
Leu Pro Asp Leu Pro Pro Lys Met Pro Val Ala Met Tyr Phe Ala Pro
625                 630                 635                 640

Pro Ile Ser Leu Cys Arg Phe Ser Gln Ser Ser Asn Gly Thr Leu Lys
            645                 650                 655

Glu Leu Glu Arg Pro Asn Ser Tyr Gly Asn Thr Ser Ser Ser Ser Ala
        660                 665                 670

Thr Asn Asp Ser Cys Ala Pro Pro Ser Val Arg Leu Pro Glu Val Gly
    675                 680                 685

Tyr

<210> SEQ ID NO 13
<211> LENGTH: 1204
<212> TYPE: PRT
<213> ORGANISM: Oryza sativa

<400> SEQUENCE: 13

Met Gly Asn His Arg Leu Leu Leu Leu Leu Leu Leu Leu Leu Ala Val
1               5                   10                  15

Val Gly Ser Asp His Gly Gly Val Leu Ala Ala Asp Glu Phe Thr Tyr
            20                  25                  30

Asn Gly Phe Gly Gly Ala Asn Leu Thr Leu Asp Gly Met Ala Ala Val
        35                  40                  45

Ala Pro Asn Gly Leu Leu Val Leu Ser Asn Gly Thr Asn Gln Met Ala
    50                  55                  60

Gly His Ala Phe His Pro Thr Pro Ile Arg Leu Arg Gly Gly Ala Ala
65                  70                  75                  80

Gly Gly Ala Val Gln Ser Phe Ser Ala Ala Phe Val Phe Ala Ile Val
                85                  90                  95

Ser Asn Phe Thr Val Leu Ser Asp Asn Gly Met Ala Phe Val Val Ala
            100                 105                 110

Pro Ser Thr Arg Leu Ser Thr Phe Asn Ala Gly Gln Tyr Leu Gly Ile
        115                 120                 125

Leu Asn Val Thr Asp Asn Gly Asn Ala Asp Asn Asn Ile Phe Ala Val
    130                 135                 140

Glu Leu Asp Thr Met Leu Asn Pro Glu Phe Gln Asp Met Asn Ser Asn
145                 150                 155                 160

His Ile Gly Val Asp Ile Asn Ser Met Lys Ser Val Gln Asn His Ser
                165                 170                 175

Ala Gly Tyr Tyr Asp Glu Ala Thr Gly Ala Phe Asn Asn Leu Ser Leu
            180                 185                 190

Ile Ser Arg Gln Pro Met Gln Val Trp Val Asp Tyr Asp Gly Ala Thr
        195                 200                 205

Thr Val Leu Asn Val Thr Met Ala Pro Leu Asp Val Pro Lys Pro Ser
    210                 215                 220

Lys Pro Leu Ile Ser Ala Pro Val Asn Leu Ser Ser Val Val Thr Asp
225                 230                 235                 240

Thr Ala Tyr Val Gly Phe Ser Ala Ala Thr Gly Val Ile Tyr Thr Arg
                245                 250                 255

His Tyr Val Leu Gly Trp Ser Phe Ser Gln Asn Gly Ala Ala Pro Ser
            260                 265                 270

Leu His Thr Ser Ser Leu Pro Ala Leu Pro Arg Phe Gly Pro Lys Pro
        275                 280                 285

Arg Ser Lys Val Leu Glu Ile Val Leu Pro Ile Ala Thr Ala Ala Phe
    290                 295                 300
```

-continued

```
Val Leu Ala Leu Val Ile Ala Ala Phe Leu Phe Val Arg Arg Arg Val
305                 310                 315                 320

Arg Tyr Ala Glu Val Arg Glu Asp Trp Glu Val Phe Gly Pro His
            325                 330                 335

Arg Phe Ser Tyr Lys Glu Leu Tyr Gln Ala Thr Lys Gly Phe Lys Asn
            340                 345                 350

Lys Gln Leu Leu Gly Thr Gly Gly Phe Gly Arg Val Tyr Lys Gly Val
            355                 360                 365

Leu Ala Lys Ser Asn Leu Glu Ile Ala Val Lys Arg Val Ser His Asp
    370                 375                 380

Ser Lys Gln Gly Met Lys Glu Phe Ile Ala Glu Val Val Ser Ile Gly
385                 390                 395                 400

His Leu Arg His Arg Asn Leu Val Gln Leu Leu Gly Tyr Cys Arg Arg
                405                 410                 415

Lys Gly Glu Leu Leu Leu Val Tyr Asp Tyr Met Ser Asn Gly Ser Leu
            420                 425                 430

Asp Lys Tyr Leu Tyr Asp Lys Thr Lys Pro Val Leu Asp Trp Gly Gln
            435                 440                 445

Arg Phe Gln Ile Ile Lys Gly Val Ala Ser Gly Leu Leu Tyr Leu His
    450                 455                 460

Glu Asp Trp Glu Gln Val Val Ile His Arg Asp Ile Lys Ala Ser Asn
465                 470                 475                 480

Val Leu Leu Asp Gly Glu Met Asn Gly Arg Leu Gly Asp Phe Gly Leu
                485                 490                 495

Ala Arg Leu Tyr Asp His Gly Val Asp Pro Gln Thr Thr His Val Val
            500                 505                 510

Gly Thr Met Gly Tyr Leu Ala Pro Glu Leu Val Arg Thr Gly Lys Ala
            515                 520                 525

Thr Pro Val Thr Asp Val Phe Ala Phe Gly Val Phe Leu Glu Val
    530                 535                 540

Thr Cys Gly Arg Arg Pro Leu Gly Cys Ile Ala Pro Asp Asp Gln Asn
545                 550                 555                 560

Val Leu Leu Asp Trp Val Gln Glu His Glu Arg Arg His Ala Ala Leu
                565                 570                 575

Asp Thr Val Asp Ala Arg Leu Cys Gly Lys Tyr Asp Ala Asp Glu Ala
            580                 585                 590

Arg Leu Ala Leu Lys Leu Gly Leu Met Cys Ala His Pro Leu Pro Asp
    595                 600                 605

Ala Arg Pro Thr Met Arg Gln Val Thr Gln Tyr Leu Asp Gly Asp Ala
    610                 615                 620

Pro Met Pro Glu Val Ala Pro Thr Met Val Ser Tyr Thr Met Leu Ala
625                 630                 635                 640

Leu Met Gln Asn Asp Gly Phe Asp Ser Phe Ala Met Ser Phe Pro Ser
                645                 650                 655

Thr Val Thr Ser Thr Ala Ser Pro Met Ser Ala Asp Val Ser Ala Val
            660                 665                 670

Ser Gly Leu Ser Gly Gly Arg Ile Ala Leu Val Thr Gly Gly Asn Lys
            675                 680                 685

Gly Val Gly Leu Glu Thr Cys Arg Gln Leu Ala Ser Arg Gly Leu Arg
    690                 695                 700

Val Val Leu Thr Ala Arg Asn Glu Ala Arg Gly Leu Glu Ala Val Asp
705                 710                 715                 720

Gly Ile Arg Arg Ser Gly Ala Ala Asp Ser Asp Val Val Phe His Gln
```

-continued

```
                725                 730                 735
Leu Asp Val Thr Asp Ala Ala Ser Val Ala Arg Leu Ala Asp Phe Val
                    740                 745                 750
Arg Asp Gln Phe Gly Arg Leu Asp Ile Leu Ile Asn Asn Ala Gly Ile
                755                 760                 765
Ser Gly Val Asp Arg Asp Pro Val Leu Val Ala Lys Val Lys Asp Gln
                770                 775                 780
Ile Glu Gly Met Asp Val Asp Gln Arg Val Glu Trp Met Arg Glu Asn
785                 790                 795                 800
Ser Lys Glu Thr Tyr Asp Glu Ala Lys Ser Cys Ile Thr Thr Asn Tyr
                805                 810                 815
Tyr Gly Ala Lys Leu Val Thr Glu Ala Leu Leu Pro Leu Leu Leu Leu
                820                 825                 830
Ser Ser Ser Gly Arg Ile Val Asn Val Ser Ser Gly Phe Gly Leu Leu
                835                 840                 845
Arg Asn Phe Asn Ser Glu Asp Leu Arg Lys Glu Phe Asp Asp Ile Asp
                850                 855                 860
Ser Leu Thr Glu Lys Arg Leu Glu Glu Leu Leu Asp Leu Phe Leu Asp
865                 870                 875                 880
Asp Phe Lys Val Asn Leu Ile Glu Ala His Gly Trp Pro Thr Gly Gly
                    885                 890                 895
Ser Ser Ala Tyr Lys Val Ala Lys Ala Ala Leu Asn Ala Tyr Thr Arg
                900                 905                 910
Ile Leu Ala Lys Lys Tyr Pro Thr Leu Arg Ile Asn Cys Leu Thr Pro
                915                 920                 925
Gly Tyr Val Lys Thr Asp Ile Ser Met His Met Gly Val Leu Thr Pro
                930                 935                 940
Glu Glu Gly Ala Ser Asn Ser Val Lys Asn Arg Asn Arg Gly Thr Thr
945                 950                 955                 960
Ser Ser Ala Ile Ala Leu Pro Gly Thr Leu Arg Ser Arg Val Ala Val
                    965                 970                 975
Val Thr Gly Gly Asn Lys Gly Ile Gly Leu Glu Val Cys Arg Gln Leu
                980                 985                 990
Ala Ala Asp Gly Ile Thr Val Val  Leu Thr Ala Arg Asp  Glu Thr Arg
                995                 1000                1005
Gly Val  Glu Ala Ala Glu Lys  Leu Arg Gly Met Gly  Leu Ser Cys
    1010                1015                1020
Val Ile  Phe His His Leu Glu  Val Thr Asp Ser Ser  Ser Val Ser
    1025                1030                1035
Arg Leu  Ala Asp Phe Leu Thr  Thr Arg Phe Gly Lys  Leu Glu Ile
    1040                1045                1050
Leu Val  Asn Asn Ala Ala Val  Ser Gly Met Glu His  Ala Gln Arg
    1055                1060                1065
Val Asp  Thr Asn Glu Glu Gln  Trp Leu Val Asn Asn  Glu Asp Leu
    1070                1075                1080
Arg Lys  Glu Leu Asp Asp Val  Asp Asn Leu Thr Glu  Glu Arg Leu
    1085                1090                1095
Asp Glu  Val Leu Asp Ser Phe  Leu Lys Asp Phe Glu  Ala Gly Ala
    1100                1105                1110
Leu Glu  Ala His Gly Trp Pro  Thr Ala Pro Phe Val  Ala Tyr Lys
    1115                1120                1125
Met Ala  Lys Val Ala Met Asn  Ala Tyr Thr Arg Ile  Leu Ala Arg
    1130                1135                1140
```

Arg His Pro Glu Leu Arg Val Asn Cys Val His Pro Gly Tyr Val
    1145                1150                1155

Lys Thr Asp Met Thr Ile Asn Ser Gly Phe Leu Thr Pro Glu Glu
    1160                1165                1170

Gly Gly Arg Asn Val Val Thr Val Ala Leu Leu Pro Asp Gly Gly
    1175                1180                1185

Pro Thr Gly Ala Tyr Phe Asp Glu Gly Arg Glu Ala Ser Phe Leu
    1190                1195                1200

Glu

<210> SEQ ID NO 14
<211> LENGTH: 760
<212> TYPE: PRT
<213> ORGANISM: Oryza sativa

<400> SEQUENCE: 14

Met Arg Ile Ser Ser Glu Ile Val Arg Cys Leu Thr Glu Gln Thr Lys
1               5                   10                  15

Glu Gln Leu Gly Ser Leu His Val Ser Leu Ala Val Ser Leu Ser Asp
            20                  25                  30

Lys Asp Arg Lys Gly Ile Glu Asp Tyr Ala Glu Asp Ser Cys Ser Leu
        35                  40                  45

Ala Ser Tyr Met Ile Arg Val Lys Pro Gly Leu Leu Pro Val Gln Pro
    50                  55                  60

Ser Pro Lys His Leu Cys Thr Phe Trp His Leu Asn Ser Leu Val Leu
65                  70                  75                  80

His Lys Leu His Met Glu Asn Gln Pro Val Leu Phe Ser Ala Val Phe
                85                  90                  95

Ile Leu Tyr Val Ser Phe Leu Gly Pro Phe Cys Ala Ser Ser Gly Glu
            100                 105                 110

Glu Ser Phe Val Tyr Ser Gly Phe Ala Ser Thr Gly Ala Ala Asn Leu
        115                 120                 125

Thr Leu Asp Gly Ser Ala Met Val Thr Thr Gly Leu Leu Gln Leu
    130                 135                 140

Thr Asp Ser Met Pro Asn Ile Gln Gly His Ala Phe Tyr Pro Thr Pro
145                 150                 155                 160

Leu Arg Phe Lys Lys Gln Ser Asn Gly Ile Val Gln Ser Phe Ser Val
                165                 170                 175

Ala Phe Met Phe Gly Ile Ile Ser Pro Tyr Ser Asp Ala Ser Thr Asp
            180                 185                 190

Gly Met Ala Phe Val Val Ala Pro Asn Lys Gly Phe Pro Asp Ala Lys
        195                 200                 205

Ala Ala Gln Phe Leu Gly Leu Leu Asn Ile Ser Ser Asp Asn Ser Thr
    210                 215                 220

Ser Asn His Met Phe Ala Val Glu Ile Asp Thr Ala Gln Asn Thr Glu
225                 230                 235                 240

Leu Asp Asp Ile Asp Gly Tyr His Val Gly Ile Asp Ile Asn Ser Leu
                245                 250                 255

His Ser Lys Lys Ser Gln His Ile Gly Phe Tyr Asn Asp Gln His Gly
            260                 265                 270

Gly Leu Leu Lys Asn Leu Thr Leu Thr Gly Ser Asn Cys Lys Pro Val
        275                 280                 285

Gln Val Trp Val Asp Tyr Asp Gly Glu Thr Thr Gln Ile Asn Val Thr
    290                 295                 300

-continued

```
Leu Ala Pro Ile Lys Val Thr Lys Pro Thr Arg Pro Leu Leu Ser Val
305                 310                 315                 320

Pro Phe Asn Leu Ser Thr Val Leu Thr Asp Gln Ala Tyr Ile Gly Phe
                325                 330                 335

Ser Ala Ala Thr Gly Pro Leu Thr Ser His Tyr Tyr Val Leu Gly Trp
            340                 345                 350

Ser Phe Ala Met Asn Ala Pro Ala Pro Ile Glu Ile Ser Arg Leu
        355                 360                 365

Pro Arg Leu Pro Cys Pro Gly Asp Asn Arg Leu Gln Lys Ile Leu Gln
    370                 375                 380

Ile Leu Leu Pro Ile Val Ala Val Ala Leu Ile Phe Ile Val Val Met
385                 390                 395                 400

Ile Leu Val Arg Arg Gln Gln Arg Tyr Ala Glu Leu Arg Glu Asp Trp
                405                 410                 415

Glu Val Glu Phe Gly Pro His Arg Phe Ser Tyr Lys Asp Leu Phe Asn
                420                 425                 430

Ala Thr Glu Gly Phe Lys Ser Lys His Ile Leu Gly Val Gly Gly Phe
            435                 440                 445

Gly Lys Val Tyr Lys Gly Val Leu Arg Thr Ser Lys Leu Glu Val Ala
        450                 455                 460

Val Lys Lys Val Ser His Gly Ser Asn Gln Gly Met Lys Glu Phe Ile
465                 470                 475                 480

Ser Glu Val Val Ser Ile Gly His Leu Arg His Arg Asn Leu Val Gln
                485                 490                 495

Leu Leu Gly Tyr Cys Arg Arg Lys Gly Glu Leu Leu Leu Val Tyr Asp
            500                 505                 510

Tyr Met Pro Asn Gly Ser Leu Asp Lys Tyr Leu Tyr Gly Glu Asp Asn
        515                 520                 525

Lys Pro Val Leu Asn Trp Ala Gln Arg Met Gln Ile Ile Lys Asp Val
    530                 535                 540

Ala Ser Gly Leu Phe Tyr Leu His Glu Lys Trp Asp Lys Val Val Ile
545                 550                 555                 560

His Arg Asp Ile Lys Ala Ser Asn Val Leu Leu Asp Ser Glu Met Asn
                565                 570                 575

Ala Arg Leu Gly Asp Phe Gly Leu Ala Arg Leu Tyr Glu His Gly Thr
            580                 585                 590

Asn Pro Gln Thr Thr His Leu Val Gly Thr Met Gly Phe Ile Ala Pro
        595                 600                 605

Glu Leu Ala Arg Thr Gly Lys Ala Ser Pro Leu Thr Asp Val Phe Ala
    610                 615                 620

Phe Gly Thr Phe Leu Leu Glu Val Thr Cys Gly Arg Trp Pro Ile Ser
625                 630                 635                 640

Asn Ser Ala His His Gly Arg Lys Met Leu Val Asp Trp Val Leu Gln
                645                 650                 655

His Trp His Gln Gly Ser Leu Pro Glu Thr Val Asp Pro Lys Leu His
            660                 665                 670

Gly Ile Tyr Asn Val Asp Glu Ala Cys Leu Val Leu Thr Leu Gly Leu
        675                 680                 685

Met Cys Ser His Pro Ile Pro Gly Ala Arg Pro Ile Met Arg Gln Val
    690                 695                 700

Met Gln Tyr Leu Asp Gly Asp Ala Pro Leu Pro Glu Phe Thr Pro Ala
705                 710                 715                 720
```

```
Thr Leu Asn Ser Ser Leu Leu Ala Ile Met His Asn Glu Gly Val Asp
            725                 730                 735

Pro Tyr Val Ala Gln Tyr Pro Trp Ser Gly Asn Ser Leu Gly Thr Met
        740                 745                 750

Thr Pro Asp Ile Leu Ser Gly Arg
        755                 760

<210> SEQ ID NO 15
<211> LENGTH: 681
<212> TYPE: PRT
<213> ORGANISM: Arabidopsis thaliana

<400> SEQUENCE: 15

Met Ser Leu Ser Arg Lys Leu Leu Val Ile Phe Phe Thr Trp Ile Thr
1               5                   10                  15

Ala Leu Ser Met Ser Lys Pro Ile Phe Val Ser Ser Asp Asn Met Asn
            20                  25                  30

Phe Thr Phe Lys Ser Phe Thr Ile Arg Asn Leu Thr Phe Leu Gly Asp
        35                  40                  45

Ser His Leu Arg Asn Gly Val Val Gly Leu Thr Arg Glu Leu Gly Val
    50                  55                  60

Pro Asp Thr Ser Ser Gly Thr Val Ile Tyr Asn Asn Pro Ile Arg Phe
65                  70                  75                  80

Tyr Asp Pro Asp Ser Asn Thr Ala Ser Phe Ser Thr His Phe Ser
                85                  90                  95

Phe Thr Val Gln Asn Leu Asn Pro Asp Pro Thr Ser Ala Gly Asp Gly
            100                 105                 110

Leu Ala Phe Phe Leu Ser His Asp Asn Asp Thr Leu Gly Ser Pro Gly
        115                 120                 125

Gly Tyr Leu Gly Leu Val Asn Ser Ser Gln Pro Met Lys Asn Arg Phe
    130                 135                 140

Val Ala Ile Glu Phe Asp Thr Lys Leu Asp Pro His Phe Asn Asp Pro
145                 150                 155                 160

Asn Gly Asn His Ile Gly Leu Asp Val Asp Ser Leu Asn Ser Ile Ser
                165                 170                 175

Thr Ser Asp Pro Leu Leu Ser Ser Gln Ile Asp Leu Lys Ser Gly Lys
            180                 185                 190

Ser Ile Thr Ser Trp Ile Asp Tyr Lys Asn Asp Leu Arg Leu Leu Asn
        195                 200                 205

Val Phe Leu Ser Tyr Thr Asp Pro Val Thr Thr Thr Lys Lys Pro Glu
    210                 215                 220

Lys Pro Leu Leu Ser Val Asn Ile Asp Leu Ser Pro Phe Leu Asn Gly
225                 230                 235                 240

Glu Met Tyr Val Gly Phe Ser Gly Ser Thr Glu Gly Ser Thr Glu Ile
                245                 250                 255

His Leu Ile Glu Asn Trp Ser Phe Lys Thr Ser Gly Phe Leu Pro Val
            260                 265                 270

Arg Ser Lys Ser Asn His Leu His Asn Val Ser Asp Ser Ser Val Val
        275                 280                 285

Asn Asp Asp Pro Val Val Ile Pro Ser Lys Lys Arg Arg His Arg His
    290                 295                 300

Asn Leu Ala Ile Gly Leu Gly Ile Ser Cys Pro Val Leu Ile Cys Leu
305                 310                 315                 320

Ala Leu Phe Val Phe Gly Tyr Phe Thr Leu Lys Lys Trp Lys Ser Val
                325                 330                 335
```

```
Lys Ala Glu Lys Glu Leu Lys Thr Glu Leu Ile Thr Gly Leu Arg Glu
            340                 345                 350

Phe Ser Tyr Lys Glu Leu Tyr Thr Ala Thr Lys Gly Phe His Ser Ser
            355                 360                 365

Arg Val Ile Gly Arg Gly Ala Phe Gly Asn Val Tyr Arg Ala Met Phe
        370                 375                 380

Val Ser Ser Gly Thr Ile Ser Ala Val Lys Arg Ser Arg His Asn Ser
385                 390                 395                 400

Thr Glu Gly Lys Thr Glu Phe Leu Ala Glu Leu Ser Ile Ile Ala Cys
                405                 410                 415

Leu Arg His Lys Asn Leu Val Gln Leu Gln Gly Trp Cys Asn Glu Lys
            420                 425                 430

Gly Glu Leu Leu Val Tyr Glu Phe Met Pro Asn Gly Ser Leu Asp
            435                 440                 445

Lys Ile Leu Tyr Gln Glu Ser Gln Thr Gly Ala Val Ala Leu Asp Trp
        450                 455                 460

Ser His Arg Leu Asn Ile Ala Ile Gly Leu Ala Ser Ala Leu Ser Tyr
465                 470                 475                 480

Leu His His Glu Cys Glu Gln Gln Val Val His Arg Asp Ile Lys Thr
                485                 490                 495

Ser Asn Ile Met Leu Asp Ile Asn Phe Asn Ala Arg Leu Gly Asp Phe
            500                 505                 510

Gly Leu Ala Arg Leu Thr Glu His Asp Lys Ser Pro Val Ser Thr Leu
        515                 520                 525

Thr Ala Gly Thr Met Gly Tyr Leu Ala Pro Glu Tyr Leu Gln Tyr Gly
    530                 535                 540

Thr Ala Thr Glu Lys Thr Asp Ala Phe Ser Tyr Gly Val Val Ile Leu
545                 550                 555                 560

Glu Val Ala Cys Gly Arg Arg Pro Ile Asp Lys Glu Pro Glu Ser Gln
                565                 570                 575

Lys Thr Val Asn Leu Val Asp Trp Val Trp Arg Leu His Ser Glu Gly
            580                 585                 590

Arg Val Leu Glu Ala Val Asp Glu Arg Leu Lys Gly Glu Phe Asp Glu
        595                 600                 605

Glu Met Met Lys Lys Leu Leu Val Gly Leu Lys Cys Ala His Pro
    610                 615                 620

Asp Ser Asn Glu Arg Pro Ser Met Arg Arg Val Leu Gln Ile Leu Asn
625                 630                 635                 640

Asn Glu Ile Glu Pro Ser Pro Val Pro Lys Met Lys Pro Thr Leu Ser
                645                 650                 655

Phe Ser Cys Gly Leu Ser Leu Asp Asp Ile Val Ser Glu Asp Glu Glu
            660                 665                 670

Gly Asp Ser Ile Val Tyr Val Val Ser
        675                 680

<210> SEQ ID NO 16
<211> LENGTH: 651
<212> TYPE: PRT
<213> ORGANISM: Arabidopsis thaliana

<400> SEQUENCE: 16

Met Ala Asn Ser Ile Leu Leu Phe Ser Phe Val Leu Val Leu Pro Phe
1               5                   10                  15

Val Cys Ser Val Gln Phe Asn Ile Ser Arg Phe Gly Ser Asp Val Ser
```

```
                    20                  25                  30
Glu Ile Ala Tyr Gln Gly Asp Ala Arg Ala Asn Gly Ala Val Glu Leu
             35                  40                  45

Thr Asn Ile Asp Tyr Thr Cys Arg Ala Gly Trp Ala Thr Tyr Gly Lys
 50                  55                  60

Gln Val Pro Leu Trp Asn Pro Gly Thr Ser Lys Pro Ser Asp Phe Ser
 65                  70                  75                  80

Thr Arg Phe Ser Phe Arg Ile Asp Thr Arg Asn Val Gly Tyr Gly Asn
                 85                  90                  95

Tyr Gly His Gly Phe Ala Phe Leu Ala Pro Ala Arg Ile Gln Leu
                100                 105                 110

Pro Pro Asn Ser Ala Gly Gly Phe Leu Gly Leu Phe Asn Gly Thr Asn
                115                 120                 125

Asn Gln Ser Ser Ala Phe Pro Leu Val Tyr Val Glu Phe Asp Thr Phe
            130                 135                 140

Thr Asn Pro Glu Trp Asp Pro Leu Asp Val Lys Ser His Val Gly Ile
145                 150                 155                 160

Asn Asn Asn Ser Leu Val Ser Ser Asn Tyr Thr Ser Trp Asn Ala Thr
                165                 170                 175

Ser His Asn Gln Asp Ile Gly Arg Val Leu Ile Phe Tyr Asp Ser Ala
                180                 185                 190

Arg Arg Asn Leu Ser Val Ser Trp Thr Tyr Asp Leu Thr Ser Asp Pro
            195                 200                 205

Leu Glu Asn Ser Ser Leu Ser Tyr Ile Ile Asp Leu Ser Lys Val Leu
210                 215                 220

Pro Ser Glu Val Thr Ile Gly Phe Ser Ala Thr Ser Gly Gly Val Thr
225                 230                 235                 240

Glu Gly Asn Arg Leu Leu Ser Trp Glu Phe Ser Ser Ser Leu Glu Leu
                245                 250                 255

Ile Asp Ile Lys Lys Ser Gln Asn Asp Lys Lys Gly Met Ile Ile Gly
                260                 265                 270

Ile Ser Val Ser Gly Phe Val Leu Leu Thr Phe Phe Ile Thr Ser Leu
            275                 280                 285

Ile Val Phe Leu Lys Arg Lys Gln Gln Lys Lys Lys Ala Glu Glu Thr
290                 295                 300

Glu Asn Leu Thr Ser Ile Asn Glu Asp Leu Glu Arg Gly Ala Gly Pro
305                 310                 315                 320

Arg Lys Phe Thr Tyr Lys Asp Leu Ala Ser Ala Asn Asn Phe Ala
                325                 330                 335

Asp Asp Arg Lys Leu Gly Glu Gly Gly Phe Gly Ala Val Tyr Arg Gly
            340                 345                 350

Tyr Leu Asn Ser Leu Asp Met Met Val Ala Ile Lys Lys Phe Ala Gly
                355                 360                 365

Gly Ser Lys Gln Gly Lys Arg Glu Phe Val Thr Glu Val Lys Ile Ile
            370                 375                 380

Ser Ser Leu Arg His Arg Asn Leu Val Gln Leu Ile Gly Trp Cys His
385                 390                 395                 400

Glu Lys Asp Glu Phe Leu Met Ile Tyr Glu Phe Met Pro Asn Gly Ser
                405                 410                 415

Leu Asp Ala His Leu Phe Gly Lys Lys Pro His Leu Ala Trp His Val
                420                 425                 430

Arg Cys Lys Ile Thr Leu Gly Leu Ala Ser Ala Leu Leu Tyr Leu His
            435                 440                 445
```

-continued

```
Glu Glu Trp Glu Gln Cys Val His Arg Asp Ile Lys Ala Ser Asn
    450                 455                 460

Val Met Leu Asp Ser Asn Phe Asn Ala Lys Leu Gly Asp Phe Gly Leu
465                 470                 475                 480

Ala Arg Leu Met Asp His Glu Leu Gly Pro Gln Thr Thr Gly Leu Ala
                485                 490                 495

Gly Thr Phe Gly Tyr Met Ala Pro Glu Tyr Ile Ser Thr Gly Arg Ala
            500                 505                 510

Ser Lys Glu Ser Asp Val Tyr Ser Phe Gly Val Val Thr Leu Glu Ile
        515                 520                 525

Val Thr Gly Arg Lys Ser Val Asp Arg Arg Gln Gly Arg Val Glu Pro
    530                 535                 540

Val Thr Asn Leu Val Glu Lys Met Trp Asp Leu Tyr Gly Lys Gly Glu
545                 550                 555                 560

Val Ile Thr Ala Ile Asp Glu Lys Leu Arg Ile Gly Gly Phe Asp Glu
                565                 570                 575

Lys Gln Ala Glu Cys Leu Met Ile Val Gly Leu Trp Cys Ala His Pro
            580                 585                 590

Asp Val Asn Thr Arg Pro Ser Ile Lys Gln Ala Ile Gln Val Leu Asn
        595                 600                 605

Leu Glu Ala Pro Val Pro His Leu Pro Thr Lys Met Pro Val Ala Thr
    610                 615                 620

Tyr His Val Ser Ser Ser Asn Thr Thr Ser Val Ser Ser Gly Gly Ala
625                 630                 635                 640

Thr Val Thr Phe Ser Ser Ala Gln His Gly Arg
                645                 650

<210> SEQ ID NO 17
<211> LENGTH: 513
<212> TYPE: PRT
<213> ORGANISM: Artificial Sequence
<220> FEATURE:
<223> OTHER INFORMATION: Synthetic consensus sequence derived from SEQ
      ID NOs 2, 12, 13, 14, 15, and 16.

<400> SEQUENCE: 17

Met Met Asn Leu Leu Leu Ala Leu Leu Ile Ser Val Leu Leu Ser
1               5                   10                  15

Val Ala Leu Ser Ile Phe Thr Phe Ser Phe Ala Asn Ile Thr Leu Gly
                20                  25                  30

Asp Ala Val Ala Val Leu Leu Glu Gln Ser Ala Gly Ala Ile Tyr
            35                  40                  45

Pro Val Arg Leu Trp Asp Ser Gly Val Ala Ser Phe Thr Phe Ser
        50                  55                  60

Phe Ile Ser Asn Thr Ser Ser Gly Met Ala Phe Ala Phe Phe Pro Ser
65                  70                  75                  80

Leu Pro Gly Ser Ala Gly Gly Tyr Leu Gly Leu Phe Asn Ser Asn Asn
                85                  90                  95

Gln Ser Thr Asn Gln Ile Val Ala Val Glu Phe Asp Thr Asn Pro Glu
            100                 105                 110

Trp Asp Pro Ile Asn His Ile Gly Ile Asp Ile Asn Ser Leu Ser Val
        115                 120                 125

Leu Asn Leu Thr Asn Lys Ile Asn Val Trp Ile Asp Tyr Asp Ala Glu
    130                 135                 140

Ser Arg Asn Leu Asn Val Thr Leu Ala Tyr Asp Ser Pro Ser Lys Pro
```

```
            145                 150                 155                 160
Leu Leu Ser Val Ile Asn Leu Ser Lys Val Leu Asp Met Tyr Ile Gly
                165                 170                 175
Phe Ser Ala Ala Thr Gly Ile Thr Glu His Tyr Ile Leu Trp Ser Phe
            180                 185                 190
Ser Ser Gly Pro Ile Lys Ser Lys Leu Ile Val Ile Ser Ile Ser Ser
        195                 200                 205
Ile Ile Leu Ile Ile Leu Ile Ile Arg Arg Ala Glu Ile Glu Asp Trp
    210                 215                 220
Glu Leu Gly Gly Pro Arg Arg Phe Ser Tyr Lys Glu Leu Tyr Ala Thr
225                 230                 235                 240
Lys Gly Phe Ala Ser Arg Leu Leu Gly Gly Phe Gly Lys Val Tyr
                245                 250                 255
Arg Gly Val Leu Arg Ser Ser Leu Glu Ile Ala Val Lys Lys Val Ser
                260                 265                 270
His Gly Ser Gln Gly Lys Lys Glu Phe Ile Ala Glu Val Ile Ile Ser
            275                 280                 285
Leu Arg His Arg Asn Leu Val Gln Leu Leu Gly Trp Cys His Glu Lys
    290                 295                 300
Gly Glu Leu Leu Leu Val Tyr Asp Phe Met Pro Asn Gly Ser Leu Asp
305                 310                 315                 320
Lys His Leu Tyr Lys Pro Val Leu Trp Leu Arg Phe Asn Ile Ile Ile
                325                 330                 335
Gly Leu Ala Ser Ala Leu Leu Tyr Leu His Glu Glu Trp Glu Gln Cys
            340                 345                 350
Val Ile His Arg Asp Ile Lys Ala Ser Asn Val Met Leu Asp Ser Glu
        355                 360                 365
Phe Asn Ala Arg Leu Gly Asp Phe Gly Leu Ala Arg Leu Asp His Asp
    370                 375                 380
Leu Pro Gln Thr Thr Leu Ala Gly Thr Met Gly Tyr Met Ala Pro Glu
385                 390                 395                 400
Leu Val Thr Gly Lys Ala Ser Glu Thr Asp Val Phe Ser Phe Gly Val
                405                 410                 415
Leu Ile Leu Glu Val Cys Gly Arg Arg Pro Ile Asp Leu Val Asp Trp
            420                 425                 430
Val Trp Asp Leu His Arg Gly Glu Leu Leu Glu Ala Val Asp Arg Leu
        435                 440                 445
Gly Phe Asp Glu Asp Glu Ala Leu Leu Leu Ile Val Gly Leu Met Cys
    450                 455                 460
Ala His Pro Asp Pro Asn Arg Pro Ser Met Arg Gln Val Ile Gln Val
465                 470                 475                 480
Leu Gly Glu Ala Pro Leu Pro Glu Leu Pro Pro Met Pro Ala Ser Tyr
                485                 490                 495
Ala Ile Met Ser Asn Asp Gly Ser Ser Ser Gly Gly Ser Thr Ser Ser
            500                 505                 510
Ala

<210> SEQ ID NO 18
<211> LENGTH: 681
<212> TYPE: PRT
<213> ORGANISM: Arabidopsis thaliana

<400> SEQUENCE: 18

Met Ser Leu Ser Arg Lys Leu Leu Val Ile Phe Phe Thr Trp Ile Thr
```

-continued

```
1               5                   10                  15
Ala Leu Ser Met Ser Lys Pro Ile Phe Val Ser Ser Asp Asn Met Asn
                20                  25                  30

Phe Thr Phe Lys Ser Phe Thr Ile Arg Asn Leu Thr Phe Leu Gly Asp
                35                  40                  45

Ser His Leu Arg Asn Gly Val Gly Leu Thr Arg Glu Leu Gly Val
                50                  55                  60

Pro Asp Thr Ser Ser Gly Thr Val Ile Tyr Asn Asn Pro Ile Arg Phe
65                      70                  75                  80

Tyr Asp Pro Asp Ser Asn Thr Thr Ala Ser Phe Ser Thr His Phe Ser
                    85                  90                  95

Phe Thr Val Gln Asn Leu Asn Pro Asp Pro Thr Ser Ala Gly Asp Gly
                100                 105                 110

Leu Ala Phe Phe Leu Ser His Asp Asn Asp Thr Leu Gly Ser Pro Gly
                115                 120                 125

Gly Tyr Leu Gly Leu Val Asn Ser Ser Gln Pro Met Lys Asn Arg Phe
                130                 135                 140

Val Ala Ile Glu Phe Asp Thr Lys Leu Asp Pro His Phe Asn Asp Pro
145                 150                 155                 160

Asn Gly Asn His Ile Gly Leu Asp Val Asp Ser Leu Asn Ser Ile Ser
                165                 170                 175

Thr Ser Asp Pro Leu Leu Ser Ser Gln Ile Asp Leu Lys Ser Gly Lys
                180                 185                 190

Ser Ile Thr Ser Trp Ile Asp Tyr Lys Asn Asp Leu Arg Leu Leu Asn
                195                 200                 205

Val Phe Leu Ser Tyr Thr Asp Pro Val Thr Thr Lys Lys Pro Glu
                210                 215                 220

Lys Pro Leu Leu Ser Val Asn Ile Asp Leu Ser Pro Phe Leu Asn Gly
225                 230                 235                 240

Glu Met Tyr Val Gly Phe Ser Gly Ser Thr Glu Gly Ser Thr Glu Ile
                245                 250                 255

His Leu Ile Glu Asn Trp Ser Phe Lys Thr Ser Gly Phe Leu Pro Val
                260                 265                 270

Arg Ser Lys Ser Asn His Leu His Asn Val Ser Asp Ser Ser Val Val
                275                 280                 285

Asn Asp Asp Pro Val Val Ile Pro Ser Lys Lys Arg His Arg His
                290                 295                 300

Asn Leu Ala Ile Gly Leu Gly Ile Ser Cys Pro Val Leu Ile Cys Leu
305                 310                 315                 320

Ala Leu Phe Val Phe Gly Tyr Phe Thr Leu Lys Lys Trp Lys Ser Val
                325                 330                 335

Lys Ala Glu Lys Glu Leu Lys Thr Glu Leu Ile Thr Gly Leu Arg Glu
                340                 345                 350

Phe Ser Tyr Lys Glu Leu Tyr Thr Ala Thr Lys Gly Phe His Ser Ser
                355                 360                 365

Arg Val Ile Gly Arg Gly Ala Phe Gly Asn Val Tyr Arg Ala Met Phe
                370                 375                 380

Val Ser Ser Gly Thr Ile Ser Ala Val Lys Arg Ser Arg His Asn Ser
385                 390                 395                 400

Thr Glu Gly Lys Thr Glu Phe Leu Ala Glu Leu Ser Ile Ile Ala Cys
                405                 410                 415

Leu Arg His Lys Asn Leu Val Gln Leu Gln Gly Trp Cys Asn Glu Lys
                420                 425                 430
```

```
Gly Glu Leu Leu Leu Val Tyr Glu Phe Met Pro Asn Gly Ser Leu Asp
            435                 440                 445

Lys Ile Leu Tyr Gln Glu Ser Gln Thr Gly Ala Val Ala Leu Asp Trp
        450                 455                 460

Ser His Arg Leu Asn Ile Ala Ile Gly Leu Ala Ser Ala Leu Ser Tyr
465                 470                 475                 480

Leu His His Glu Cys Glu Gln Gln Val Val His Arg Asp Ile Lys Thr
                485                 490                 495

Ser Asn Ile Met Leu Asp Ile Asn Phe Asn Ala Arg Leu Gly Asp Phe
            500                 505                 510

Gly Leu Ala Arg Leu Thr Glu His Asp Lys Ser Pro Val Ser Thr Leu
        515                 520                 525

Thr Ala Gly Thr Met Gly Tyr Leu Ala Pro Glu Tyr Leu Gln Tyr Gly
            530                 535                 540

Thr Ala Thr Glu Lys Thr Asp Ala Phe Ser Tyr Gly Val Val Ile Leu
545                 550                 555                 560

Glu Val Ala Cys Gly Arg Arg Pro Ile Asp Lys Glu Pro Glu Ser Gln
                565                 570                 575

Lys Thr Val Asn Leu Val Asp Trp Val Trp Arg Leu His Ser Glu Gly
            580                 585                 590

Arg Val Leu Glu Ala Val Asp Glu Arg Leu Lys Gly Glu Phe Asp Glu
        595                 600                 605

Glu Met Met Lys Lys Leu Leu Leu Val Gly Leu Lys Cys Ala His Pro
            610                 615                 620

Asp Ser Asn Glu Arg Pro Ser Met Arg Arg Val Leu Gln Ile Leu Asn
625                 630                 635                 640

Asn Glu Ile Glu Pro Ser Pro Val Pro Lys Met Lys Pro Thr Leu Ser
                645                 650                 655

Phe Ser Cys Gly Leu Ser Leu Asp Asp Ile Val Ser Glu Asp Glu Glu
            660                 665                 670

Gly Asp Ser Ile Val Tyr Val Val Ser
        675                 680

<210> SEQ ID NO 19
<211> LENGTH: 693
<212> TYPE: PRT
<213> ORGANISM: Arabidopsis thaliana

<400> SEQUENCE: 19

Met Gly Ile Ala Arg Ser Ile Asn Ser Phe Met Phe Phe Phe Phe Leu
1               5                   10                  15

Met Ile Leu Ser Asn Ala Ser Lys Ser Ser Val Leu Ala Glu Ala Thr
            20                  25                  30

Thr Ala Lys Phe Thr Phe Ile Gly Phe Lys Glu Asn Gln Thr Asp Ile
        35                  40                  45

Gln Thr Glu Gly Ala Ser Thr Ile Gln His Asp Asn Asp Leu Leu Arg
    50                  55                  60

Leu Thr Asn Arg Lys Gln Asn Val Thr Gly Thr Ala Phe Tyr Arg Lys
65                  70                  75                  80

Pro Ile Arg Leu Arg Glu Leu Thr Asn Ser Ser Asp Ile Lys Val Cys
                85                  90                  95

Ser Phe Ser Thr Ser Phe Val Phe Val Ile Leu Pro Ser Ser Pro Gly
            100                 105                 110

Asn Gly Gly Phe Gly Phe Thr Phe Thr Leu Ser Pro Thr Pro Asn Arg
```

-continued

```
                115                 120                 125
Pro Gly Ala Glu Ser Ala Gln Tyr Leu Gly Leu Leu Asn Arg Thr Asn
    130                 135                 140

Asn Gly Asn Pro Ser Asn His Val Phe Ala Val Glu Phe Asp Thr Val
145                 150                 155                 160

Gln Gly Phe Lys Asp Gly Ala Asp Arg Arg Gly Asn His Ile Gly Leu
                165                 170                 175

Asn Phe Asn Asn Leu Ser Ser Asn Val Gln Glu Pro Leu Ile Tyr Tyr
            180                 185                 190

Asp Thr Glu Asp Arg Lys Glu Asp Phe Gln Leu Glu Ser Gly Glu Pro
        195                 200                 205

Ile Arg Val Leu Ile Asp Tyr Asp Gly Ser Ser Glu Thr Leu Asn Val
    210                 215                 220

Thr Ile Tyr Pro Thr Arg Leu Glu Phe Lys Pro Lys Lys Pro Leu Ile
225                 230                 235                 240

Ser Arg Arg Val Ser Glu Leu Ser Glu Ile Val Lys Asp Glu Met Tyr
                245                 250                 255

Val Gly Phe Thr Ala Ala Thr Gly Lys Asp Gln Ser Ser Ala His Tyr
            260                 265                 270

Val Met Gly Trp Ser Phe Ser Ser Cys Gly Glu Asn Pro Met Ala Asp
        275                 280                 285

Trp Leu Glu Ile Ser Arg Leu Pro Pro Pro Arg Leu Ser Asn Lys
    290                 295                 300

Lys Gly Tyr Asn Ser Gln Val Ile Val Leu Ile Val Ala Leu Ser Ile
305                 310                 315                 320

Val Thr Leu Val Leu Leu Val Leu Phe Ile Phe Val Met Tyr Lys
                325                 330                 335

Arg Arg Ile Gln Glu Glu Asp Thr Leu Glu Asp Trp Glu Ile Asp Tyr
            340                 345                 350

Pro His Arg Phe Arg Tyr Arg Asp Leu Tyr Leu Ala Thr Lys Lys Phe
        355                 360                 365

Lys Glu Ser Glu Ile Ile Gly Thr Gly Gly Phe Gly Ile Val Tyr Arg
    370                 375                 380

Gly Asn Leu Ser Ser Gly Pro Ile Ala Val Lys Lys Ile Thr Ser
385                 390                 395                 400

Asn Ser Leu Gln Gly Val Arg Glu Phe Met Ala Glu Ile Glu Ser Leu
                405                 410                 415

Gly Arg Leu Gly His Lys Asn Leu Val Asn Leu Gln Gly Trp Cys Lys
            420                 425                 430

His Lys Asn Glu Leu Leu Leu Ile Tyr Asp Tyr Ile Pro Asn Gly Ser
        435                 440                 445

Leu Asp Ser Leu Leu Tyr Gln Thr Pro Arg Arg Asn Gly Ile Val Leu
    450                 455                 460

Pro Trp Asp Val Arg Phe Glu Ile Ile Lys Gly Ile Ala Ser Gly Leu
465                 470                 475                 480

Leu Tyr Leu His Glu Glu Trp Glu Gln Ile Val His Arg Asp Val
                485                 490                 495

Lys Pro Ser Asn Val Leu Ile Asp Glu Asp Met Asn Ala Lys Leu Gly
            500                 505                 510

Asp Phe Gly Leu Ala Arg Leu Tyr Glu Arg Gly Thr Leu Thr Gln Thr
        515                 520                 525

Thr Lys Ile Val Gly Thr Leu Gly Tyr Met Ala Pro Glu Leu Thr Arg
    530                 535                 540
```

```
Asn Gly Lys Gly Ser Thr Ala Ser Asp Val Phe Ala Phe Gly Val Leu
545                 550                 555                 560

Leu Leu Glu Ile Val Cys Gly Asn Lys Pro Thr Asn Ala Glu Asn Phe
                565                 570                 575

Phe Leu Ala Asp Trp Val Met Glu Phe His Thr Asn Gly Gly Ile Leu
            580                 585                 590

Cys Val Val Asp Gln Asn Leu Gly Ser Ser Phe Asn Gly Arg Glu Ala
        595                 600                 605

Lys Leu Ala Leu Val Val Gly Leu Leu Cys Cys His Gln Lys Pro Lys
    610                 615                 620

Phe Arg Pro Ser Met Arg Met Val Leu Arg Tyr Leu Asn Gly Glu Glu
625                 630                 635                 640

Asn Val Pro Gln Ile Asp Glu Asn Trp Gly Phe Ser Asp Ser Ser Arg
                645                 650                 655

Asp Asp His Lys Ser Asn Val Val Gly Tyr Val Ser Ser Asp Arg Ala
            660                 665                 670

Ser Ser Ser Asn Thr Phe Ser Ser Phe Ser Asn Val Ser Ser Ser Ser
        675                 680                 685

Ile Val Ser Gly Arg
    690

<210> SEQ ID NO 20
<211> LENGTH: 688
<212> TYPE: PRT
<213> ORGANISM: Arabidopsis thaliana

<400> SEQUENCE: 20

Met Leu Val Leu Phe Leu Leu Thr Ile Pro Thr Arg Ala Gln Arg
1               5                   10                  15

Thr Thr Thr Glu Thr Pro Lys Thr Glu Phe Ile Phe Arg Gly Phe Ser
                20                  25                  30

Gly Asn Gln Ser Asn Ile Val Thr Thr Gly Ala Ala Thr Ile Lys Leu
            35                  40                  45

Asp Gly Leu Leu Arg Leu Thr Asp Arg Asn Ser Asn Val Thr Gly Thr
    50                  55                  60

Ser Phe Tyr His Lys Pro Val Arg Leu Leu Glu Thr Asn Thr Ser Ser
65                  70                  75                  80

Thr Asn Ser Thr Ile Arg Ser Phe Ser Thr Ser Phe Val Phe Ile
                85                  90                  95

Ile Pro Thr Ser Ser Ser Asn Gly Gly Phe Gly Phe Thr Phe Thr Leu
                100                 105                 110

Ser Pro Thr Pro Asp Arg Thr Gly Ala Glu Ser Ala Gln Tyr Leu Gly
            115                 120                 125

Leu Leu Asn Lys Ala Asn Asp Gly Asn Ser Thr Asn His Val Phe Ala
    130                 135                 140

Val Glu Phe Asp Thr Val Gln Gly Phe Lys Asp Gly Ala Asp Arg Thr
145                 150                 155                 160

Gly Asn His Ile Gly Leu Asn Phe Asn Ser Leu Thr Ser Asp Val Gln
                165                 170                 175

Glu Pro Val Val Tyr Tyr Asp Asn Glu Asp Pro Asn Arg Lys Glu Asp
            180                 185                 190

Phe Pro Leu Gln Ser Gly Asp Pro Ile Arg Ala Ile Leu Asp Tyr Asp
    195                 200                 205

Gly Pro Thr Gln Thr Leu Asn Leu Thr Val Tyr Pro Ala Asn Leu Lys
```

```
            210                 215                 220
Ser Arg Pro Val Arg Pro Leu Ile Ser Arg Pro Val Pro Lys Leu Ser
225                 230                 235                 240

Gln Ile Val Gln Glu Glu Met Tyr Val Gly Phe Thr Ala Ala Thr Gly
                    245                 250                 255

Arg Asp Gln Ser Ser Ala His Tyr Val Met Gly Trp Ser Phe Ser Ser
                260                 265                 270

Gly Gly Asp Leu Leu Thr Glu Asp Thr Leu Asp Leu Leu Glu Leu Pro
            275                 280                 285

Arg Pro Pro Asn Thr Ala Lys Lys Arg Gly Tyr Asn Ser Gln Val
290                 295                 300

Leu Ala Leu Ile Val Ala Leu Ser Gly Val Thr Val Ile Leu Leu Ala
305                 310                 315                 320

Leu Leu Phe Phe Phe Val Met Tyr Lys Lys Arg Leu Gln Gln Gly Glu
                325                 330                 335

Val Leu Glu Asp Trp Glu Ile Asn His Pro His Arg Leu Arg Tyr Lys
                340                 345                 350

Asp Leu Tyr Ala Ala Thr Asp Gly Phe Lys Glu Asn Arg Ile Val Gly
            355                 360                 365

Thr Gly Gly Phe Gly Thr Val Phe Arg Gly Asn Leu Ser Ser Pro Ser
370                 375                 380

Ser Asp Gln Ile Ala Val Lys Lys Ile Thr Pro Asn Ser Met Gln Gly
385                 390                 395                 400

Val Arg Glu Phe Ile Ala Glu Ile Glu Ser Leu Gly Arg Leu Arg His
                405                 410                 415

Lys Asn Leu Val Asn Leu Gln Gly Trp Cys Lys Gln Lys Asn Asp Leu
                420                 425                 430

Leu Leu Ile Tyr Asp Tyr Ile Pro Asn Gly Ser Leu Asp Ser Leu Leu
            435                 440                 445

Tyr Ser Arg Pro Arg Gln Ser Gly Val Val Leu Ser Trp Asn Ala Arg
            450                 455                 460

Phe Lys Ile Ala Lys Gly Ile Ala Ser Gly Leu Leu Tyr Leu His Glu
465                 470                 475                 480

Glu Trp Glu Lys Val Val Ile His Arg Asp Ile Lys Pro Ser Asn Val
                485                 490                 495

Leu Ile Glu Asp Asp Met Asn Pro Arg Leu Gly Asp Phe Gly Leu Ala
            500                 505                 510

Arg Leu Tyr Glu Arg Gly Ser Gln Ser Asn Thr Thr Val Val Gly
            515                 520                 525

Thr Ile Gly Tyr Met Ala Pro Glu Leu Ala Arg Asn Gly Lys Ser Ser
530                 535                 540

Ser Ala Ser Asp Val Phe Ala Phe Gly Val Leu Leu Leu Glu Ile Val
545                 550                 555                 560

Ser Gly Arg Arg Pro Thr Asp Ser Gly Thr Phe Phe Leu Ala Asp Trp
                565                 570                 575

Val Met Glu Leu His Ala Arg Gly Glu Ile Leu His Ala Val Asp Pro
                580                 585                 590

Arg Leu Gly Phe Gly Tyr Asp Gly Val Glu Ala Arg Leu Ala Leu Val
            595                 600                 605

Val Gly Leu Leu Cys Cys His Gln Arg Pro Thr Ser Arg Pro Ser Met
            610                 615                 620

Arg Thr Val Leu Arg Tyr Leu Asn Gly Asp Asp Val Pro Glu Ile
625                 630                 635                 640
```

```
Asp Asn Asp Trp Gly Tyr Ser Asp Ser Ser Arg Ser Asp Leu Gly Ser
            645                 650                 655

Asn Phe Glu Gly Tyr Val Ser Ser Asp Arg Ala Ser Ser Ser Val Pro
            660                 665                 670

Ser Phe Ser Val Thr Arg Val Ser Ser Ser Val Ile Ser Gly Arg
            675                 680                 685

<210> SEQ ID NO 21
<211> LENGTH: 677
<212> TYPE: PRT
<213> ORGANISM: Arabidopsis thaliana

<400> SEQUENCE: 21

Met Phe Val Lys Leu Lys Leu Ile Phe Phe Phe Leu Leu Cys Gln
1               5                   10                  15

Ile Met Ile Ser Ser Ser Gln Asn Leu Asn Phe Thr Tyr Asn Gly Phe
                20                  25                  30

His Pro Pro Leu Thr Asp Ile Ser Leu Gln Gly Leu Ala Thr Val Thr
            35                  40                  45

Pro Asn Gly Leu Leu Lys Leu Thr Asn Thr Ser Val Gln Lys Thr Gly
50                  55                  60

His Ala Phe Cys Thr Glu Arg Ile Arg Phe Lys Asp Ser Gln Asn Gly
65                  70                  75                  80

Asn Val Ser Ser Phe Ser Thr Thr Phe Val Phe Ala Ile His Ser Gln
                85                  90                  95

Ile Pro Thr Leu Ser Gly His Gly Ile Ala Phe Val Val Ala Pro Thr
            100                 105                 110

Leu Gly Leu Pro Phe Ala Leu Pro Ser Gln Tyr Ile Gly Leu Phe Asn
            115                 120                 125

Ile Ser Asn Asn Gly Asn Asp Thr Asn His Ile Phe Ala Val Glu Phe
            130                 135                 140

Asp Thr Ile Gln Ser Ser Glu Phe Gly Asp Pro Asn Asp Asn His Val
145                 150                 155                 160

Gly Ile Asp Leu Asn Gly Leu Arg Ser Ala Asn Tyr Ser Thr Ala Gly
                165                 170                 175

Tyr Arg Asp Asp His Asp Lys Phe Gln Asn Leu Ser Leu Ile Ser Arg
            180                 185                 190

Lys Arg Ile Gln Val Trp Ile Asp Tyr Asp Asn Arg Ser His Arg Ile
            195                 200                 205

Asp Val Thr Val Ala Pro Phe Asp Ser Asp Lys Pro Arg Lys Pro Leu
            210                 215                 220

Val Ser Tyr Val Arg Asp Leu Ser Ser Ile Leu Leu Glu Asp Met Tyr
225                 230                 235                 240

Val Gly Phe Ser Ser Ala Thr Gly Ser Val Leu Ser Glu His Phe Leu
                245                 250                 255

Val Gly Trp Ser Phe Arg Leu Asn Gly Glu Ala Pro Met Leu Ser Leu
            260                 265                 270

Ser Lys Leu Pro Lys Leu Pro Arg Phe Glu Pro Arg Ile Ser Glu
            275                 280                 285

Phe Tyr Lys Ile Gly Met Pro Leu Ile Ser Leu Ser Leu Ile Phe Ser
290                 295                 300

Ile Ile Phe Leu Ala Phe Tyr Ile Val Arg Arg Lys Lys Tyr Glu
305                 310                 315                 320

Glu Glu Leu Asp Asp Trp Glu Thr Glu Phe Gly Lys Asn Arg Phe Arg
```

```
                    325                 330                 335
Phe Lys Glu Leu Tyr His Ala Thr Lys Gly Phe Lys Glu Lys Asp Leu
                340                 345                 350

Leu Gly Ser Gly Gly Phe Gly Arg Val Tyr Arg Gly Ile Leu Pro Thr
            355                 360                 365

Thr Lys Leu Glu Val Ala Val Lys Arg Val Ser His Asp Ser Lys Gln
        370                 375                 380

Gly Met Lys Glu Phe Val Ala Glu Ile Val Ser Ile Gly Arg Met Ser
385                 390                 395                 400

His Arg Asn Leu Val Pro Leu Leu Gly Tyr Cys Arg Arg Gly Glu
                405                 410                 415

Leu Leu Leu Val Tyr Asp Tyr Met Pro Asn Gly Ser Leu Asp Lys Tyr
                420                 425                 430

Leu Tyr Asn Asn Pro Glu Thr Thr Leu Asp Trp Lys Gln Arg Ser Thr
            435                 440                 445

Ile Ile Lys Gly Val Ala Ser Gly Leu Phe Tyr Leu His Glu Glu Trp
        450                 455                 460

Glu Gln Val Val Ile His Arg Asp Val Lys Ala Ser Asn Val Leu Leu
465                 470                 475                 480

Asp Ala Asp Phe Asn Gly Arg Leu Gly Asp Phe Gly Leu Ala Arg Leu
                485                 490                 495

Tyr Asp His Gly Ser Asp Pro Gln Thr Thr His Val Val Gly Thr Leu
            500                 505                 510

Gly Tyr Leu Ala Pro Glu His Ser Arg Thr Gly Arg Ala Thr Thr Thr
        515                 520                 525

Thr Asp Val Tyr Ala Phe Gly Ala Phe Leu Leu Glu Val Val Ser Gly
    530                 535                 540

Arg Arg Pro Ile Glu Phe His Ser Ala Ser Asp Asp Thr Phe Leu Leu
545                 550                 555                 560

Val Glu Trp Val Phe Ser Leu Trp Leu Arg Gly Asn Ile Met Glu Ala
                565                 570                 575

Lys Asp Pro Lys Leu Gly Ser Ser Gly Tyr Asp Leu Glu Glu Val Glu
            580                 585                 590

Met Val Leu Lys Leu Gly Leu Leu Cys Ser His Ser Asp Pro Arg Ala
        595                 600                 605

Arg Pro Ser Met Arg Gln Val Leu Gln Tyr Leu Arg Gly Asp Met Ala
    610                 615                 620

Leu Pro Glu Leu Thr Pro Leu Asp Leu Ser Ala Gly Ser Val Met Asn
625                 630                 635                 640

Leu Gly Gly Arg Asp Gly Phe Ser Gly Ile Ala Met Thr Asp Phe Ser
                645                 650                 655

Thr Val Phe Lys Gly Phe Thr Gly Gly Ser Ser Ile Ala Asp Ser Leu
            660                 665                 670

Leu Ser Gly Gly Arg
        675

<210> SEQ ID NO 22
<211> LENGTH: 632
<212> TYPE: PRT
<213> ORGANISM: Pinus radiata

<400> SEQUENCE: 22

Met Leu Phe Pro Trp Arg Ser Leu Val Leu Ile Ala Phe Thr Ser Leu
1               5                   10                  15
```

```
Val Val Gln Leu Ile Pro Ala Gln Ala Val Glu Asp Arg Arg His Asp
             20                  25                  30

Thr Thr Phe Leu Phe Asp Gly Phe Asn Gly Thr Asn Leu Ile Leu Glu
         35                  40                  45

Ala Asn Ala Ser Val Ile Gly Ser Glu Ser Val Leu Ser Leu Thr Asn
     50                  55                  60

His Ser His Glu Phe Met Leu Gly Arg Ala Leu Tyr Ala Ala Pro Val
 65                  70                  75                  80

Gln Met Lys Asn Asn His Thr Val Ser Ser Phe Ser Thr Thr Phe Val
                 85                  90                  95

Phe Ser Ile Val Pro Pro Ser Asn Glu Gly His Gly Leu Ala
             100                 105                 110

Phe Ile Met Thr Pro Tyr Thr Ser Pro Met Gly Ala Gln Pro Val Gln
             115                 120                 125

Tyr Leu Gly Leu Leu Asn Leu Thr Ser Asn Gly Gln Pro Tyr Asn His
         130                 135                 140

Leu Phe Ala Val Glu Phe Asp Thr Ile Met Asn Val Glu Phe Lys Asp
145                 150                 155                 160

Pro Asp Arg Asn His Val Gly Val Asp Ile Asn Ser Leu Ile Ser Val
                 165                 170                 175

Gln Thr Glu Thr Ala Gly Tyr Trp Asn Gly Glu Glu Phe His Glu Leu
             180                 185                 190

Asn Leu Arg Ser Gly Arg Asn Ile Gln Ala Trp Ile Asp Tyr Asp His
             195                 200                 205

Leu Glu Ser Ser Leu Asn Val Thr Ile Thr Val Ala Gly Leu Pro Arg
         210                 215                 220

Pro Gln Arg Pro Leu Ile Ser Leu Gln Ile Asp Leu Gln Asn Ile Val
225                 230                 235                 240

Glu Glu Lys Met Leu Val Gly Phe Ser Ala Ala Thr Gly Leu Leu Val
             245                 250                 255

Glu Asp His Tyr Ile Leu Ala Trp Ser Phe Thr Thr Glu Asp Thr Ala
             260                 265                 270

Pro Pro Leu Asp Val Ser Cys Leu Ser Ser Phe Ala Asn Met Tyr Ser
             275                 280                 285

Glu Pro Leu Ser Arg Gly Phe Ile Ala Gly Val Thr Val Ser Val
             290                 295                 300

Val Leu Phe Trp Leu Val Ile Ala Ala Ala Met Phe Leu Arg Arg Thr
305                 310                 315                 320

Leu Asn Arg Glu Thr Val Glu Trp Glu Gln Glu Tyr Trp Pro His
                 325                 330                 335

Arg Phe Asp Tyr Lys Glu Leu Arg Ile Ala Thr Arg Gly Phe Arg Asp
                 340                 345                 350

Glu Asn Leu Leu Gly Tyr Gly Gly Phe Gly Met Val Tyr Lys Gly Phe
             355                 360                 365

Leu Pro Arg Ser Gly Gln Glu Val Ala Val Lys Cys Ile Thr Thr Glu
         370                 375                 380

Phe Lys Glu Gly Ile Lys Gly Phe Val Ala Glu Ile Ser Ser Met Gly
385                 390                 395                 400

Arg Leu Gln His Arg Asn Leu Val Gln Leu Arg Gly Trp Cys Arg Arg
                 405                 410                 415

His Thr Gln Leu Phe Ile Val Tyr Asp Tyr Met Pro Asn Gly Ser Leu
             420                 425                 430

His Lys Leu Ile Phe Gly Ser Pro Thr Thr Val Leu Pro Trp His Arg
```

-continued

```
                 435                 440                 445
Arg Tyr Ala Ile Leu Lys Gly Val Ala Ala Gly Leu Leu Tyr Leu His
            450                 455                 460

Glu Gln Trp Glu Lys Arg Val Val His Arg Asp Ile Lys Ser Ser Asn
465                 470                 475                 480

Val Leu Leu Asp Ser Glu Phe Asn Gly Arg Leu Ser Asp Phe Gly Leu
                485                 490                 495

Ala Arg Leu Tyr Asp His Ser Glu Asn Pro Glu Thr Thr Tyr Val Val
            500                 505                 510

Gly Thr Leu Gly Tyr Ile Ala Pro Glu Leu Ile Gln Thr Gly Lys Ala
            515                 520                 525

Thr Pro Ser Ser Asp Val Phe Ser Phe Gly Val Leu Leu Leu Glu Val
            530                 535                 540

Ala Cys Gly Lys Ser Pro Val Asp Ser Leu Glu Asp Ser Glu Arg Met
545                 550                 555                 560

Ile Leu Val Glu Trp Ala Trp Glu Leu Tyr Thr Glu Gly Arg Leu Leu
                565                 570                 575

Glu Ala Ser Asp Pro Lys Leu Ala Ala Lys Gly Gly Tyr Asp Glu Gly
            580                 585                 590

Glu Met Glu Lys Val Leu Lys Leu Gly Leu Leu Cys Ser His Pro Glu
            595                 600                 605

Pro Glu Ser Arg Leu Ser Met Arg Gln Val Cys Gln Val Leu Asn Gly
            610                 615                 620

Glu Ala Pro Val Pro Cys Arg Trp
625                 630

<210> SEQ ID NO 23
<211> LENGTH: 543
<212> TYPE: PRT
<213> ORGANISM: Artificial Sequence
<220> FEATURE:
<223> OTHER INFORMATION: Synthetic consensus sequence derived from SEQ
      ID NOs  2, 18, 19, 20, 21, and 22.

<400> SEQUENCE: 23

Leu Leu Val Ile Phe Phe Leu Ile Leu Leu Ala Gln Val Ala Glu
1               5                   10                  15

Ser Ile Phe Thr Phe Gly Phe Thr Asn Ile Leu Gly Ala Ala Thr Val
                20                  25                  30

Leu Leu Arg Leu Thr Asn Asn Val Thr Gly Thr Ala Phe Tyr Pro Ile
            35                  40                  45

Arg Phe Lys Asp Thr Val Ala Ser Phe Ser Thr Ser Phe Val Phe Ser
        50                  55                  60

Ile Ile Pro Pro Ser Gly Gly Gly Leu Ala Phe Ile Leu Ser Pro Thr
65                  70                  75                  80

Gly Ala Ala Gln Tyr Leu Gly Leu Leu Asn Thr Asn Gly Asn Thr
                85                  90                  95

Asn His Val Phe Ala Val Glu Phe Asp Thr Ile Gln Asp Phe Ala Asp
                100                 105                 110

Pro Gly Asn His Ile Gly Leu Asp Val Asn Ser Leu Ser Val Glu Ile
            115                 120                 125

Tyr Tyr Asp Glu Asp Arg Asp Phe Leu Ser Gly Lys Ile Gln Val Trp
        130                 135                 140

Ile Asp Tyr Asp Gly Ser Thr Leu Asn Val Thr Ile Ala Pro Ala Leu
145                 150                 155                 160
```

-continued

```
Lys Pro Lys Pro Leu Ile Ser Ile Val Ile Asp Leu Ser Ile Val Glu
            165                 170                 175

Glu Met Tyr Val Gly Phe Ser Ala Ala Thr Gly Asp Ser Ser Ala His
        180                 185                 190

Tyr Ile Met Gly Trp Ser Phe Ser Ser Gly Glu Ala Pro Met Asp Ser
    195                 200                 205

Leu Leu Pro Leu Pro Lys Arg Ser Leu Val Ile Gly Leu Ile Ile Ala
    210                 215                 220

Leu Ser Val Val Ser Leu Ile Leu Leu Ile Leu Phe Met Tyr Lys
225                 230                 235                 240

Arg Arg Leu Glu Glu Leu Glu Asp Trp Glu Ile Glu Tyr Gly His Arg
                245                 250                 255

Phe Arg Tyr Lys Glu Leu Tyr Ala Thr Lys Gly Phe Lys Glu Glu Leu
                260                 265                 270

Leu Gly Thr Gly Gly Phe Gly Val Tyr Arg Gly Ile Leu Ser Ser Gly
            275                 280                 285

Ile Ala Val Lys Lys Ile Thr Asn Ser Gln Gly Val Lys Glu Phe Val
290                 295                 300

Ala Glu Ile Ser Ser Ile Gly Arg Leu Arg His Lys Asn Leu Val Gln
305                 310                 315                 320

Leu Gln Gly Trp Cys Lys Lys Gly Glu Leu Leu Val Tyr Asp Tyr
                325                 330                 335

Met Pro Asn Gly Ser Leu Asp Lys Leu Leu Tyr Gln Ser Pro Gly Val
            340                 345                 350

Val Leu Trp Arg Phe Ile Ile Lys Gly Ile Ala Ser Gly Leu Leu Tyr
            355                 360                 365

Leu His Glu Glu Trp Glu Gln Val Val Ile His Arg Asp Ile Lys Ala
    370                 375                 380

Ser Asn Val Leu Leu Asp Asp Phe Asn Gly Arg Leu Gly Asp Phe Gly
385                 390                 395                 400

Leu Ala Arg Leu Tyr Glu Arg Gly Ser Pro Gln Thr Thr Val Val Gly
                405                 410                 415

Thr Leu Gly Tyr Met Ala Pro Glu Leu Arg Thr Gly Lys Ala Thr Thr
            420                 425                 430

Ala Ser Asp Val Phe Ala Phe Gly Val Leu Leu Leu Glu Val Val Cys
            435                 440                 445

Gly Arg Arg Pro Pro Ser Glu Thr Phe Ile Leu Val Asp Trp Val Trp
450                 455                 460

Glu Leu His Thr Gly Ile Leu Glu Ala Val Asp Pro Lys Leu Gly Gly
465                 470                 475                 480

Phe Asp Glu Ala Lys Leu Ala Leu Val Gly Leu Leu Cys Ala His
                485                 490                 495

Pro Asp Pro Ser Arg Pro Ser Met Arg Val Leu Gln Tyr Leu Asn Gly
            500                 505                 510

Glu Ile Pro Val Pro Ile Pro Phe Ser Ser Asp Ser Asn Gly Tyr
            515                 520                 525

Ser Ser Asp Phe Ala Ser Ser Ser Ile Ser Ile Gly Arg
530                 535                 540
```

US 7,880,055 B2

LECITIN-LIKE PROTEIN KINASE STRESS-RELATED POLYPEPTIDES AND METHODS OF USE IN PLANTS

This application is a national phase filing pursuant to 35 U.S.C. §371 of international application number PCT/EP2006/063270, filed Jun. 16, 2006, which claims priority benefit of U.S. provisional application Ser. No. 60/692,005, filed Jun. 17, 2005.

BACKGROUND OF THE INVENTION

1. Field of the Invention

This invention relates generally to nucleic acid sequences encoding polypeptides that are associated with abiotic stress responses and abiotic stress tolerance in plants. In particular, this invention relates to nucleic acid sequences encoding polypeptides that confer upon the plant increased growth and/or that confer increased drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as soybean, rice, maize (corn), cotton, and wheat caused by these stresses represent a significant economic and political factor and contribute to food shortages in many underdeveloped countries. Plants are typically exposed during their life cycle to conditions of reduced environmental water content. Most plants have evolved strategies to protect themselves against these conditions of desiccation. However, if the severity and duration of the drought conditions are too great, the effects on development, growth, and yield of most crop plants are profound. Continuous exposure to drought conditions causes major alterations in the plant metabolism, which ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold, and salt tolerance in model drought-, cold-, and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerant plants using biotechnological methods.

Drought stresses, heat stresses, cold stresses, and salt stresses have a common theme important for plant growth and that is water availability. As discussed above, most plants have evolved strategies to protect themselves against conditions of desiccation; however, if the severity and duration of the drought conditions are too great, the effects on plant development, growth and yield of most crop plants are profound. Furthermore, most of the crop plants are very susceptible to higher salt concentrations in the soil. Because high salt content in some soils results in less water being available for cell intake, high salt concentration has an effect on plants similar to the effect of drought on plants. Additionally, under freezing temperatures, plant cells lose water as a result of ice formation that starts in the apoplast and withdraws water from the symplast. A plant's molecular response mechanisms to each of these stress conditions are common, and protein kinases, such as lectin-like protein kinases, play an essential role in these molecular mechanisms.

Protein kinases represent a superfamily, and the members of this superfamily catalyze the reversible transfer of a phosphate group of ATP to serine, threonine, and tyrosine amino acid side chains on target polypeptides. Protein kinases are primary elements in signaling processes in plants and have been reported to play crucial roles in perception and transduction of signals that allow a cell (and the plant) to respond to environmental stimuli.

One type of protein kinase is the lectin-like protein kinase (LLPK) or lectin receptor kinase. Structural features of this type of protein kinase include an amino-terminal membrane-targeting signal sequence, a legume lectin-like extracellular domain, a single membrane-spanning domain, and a characteristic serine/threonine protein kinase catalytic domain. Members of this family have been reported to be involved in cell-cell communication, defense against predators and pathogens, and plant development and reproduction (Barre et al., 2002, Crit. Rev. Plant Sci. 21:379-399). Forty-two putative lectin receptor kinases and nine soluble legume lectin sequences have been identified in *Arabidopsis*.

Although some genes that are involved in stress responses and water use efficiency in plants have been characterized, the characterization and cloning of plant genes that confer stress tolerance and water use efficiency remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in tolerance, direct evidence is still lacking, and the functions of many stress-responsive genes are unknown.

There is a fundamental physiochemically-constrained trade-off, in all terrestrial photosynthetic organisms, between $CO_2$ absorption and water loss (Taiz and Zeiger 1991 Plant Physiology, Benjamin/Cummings Publishing Co, p 94). $CO_2$ needs to be in aqueous solution for the action of $CO_2$ fixation enzymes such as Rubisco (Ribulose 1,5-bisphosphate Carboxylase/Oxygenase) and PEPC (Phosphoenolpyruvate carboxylase). As a wet cell surface is required for $CO_2$ diffusion, evaporation will inevitably occur when the humidity is below 100% (Taiz and Zeiger 1991 Plant Physiology, Benjamin/Cummings Publishing Co p 257). Plants have numerous physiological mechanisms to reduce water loss (e.g. waxy cuticles, stomatal closure, leaf hairs, sunken stomatal pits). As these barriers do not discriminate between water and $CO_2$ flux, these water conservation measures will also act to increase resistance to $CO_2$ uptake (Kramer 1983 Water Relations of Plants, Academic Press p 305). Photosynthetic $CO_2$ uptake is absolutely required for plant growth and biomass accumulation in photoautotrophic plants. Water Use Efficiency (WUE) is a parameter frequently used to estimate the trade off between water consumption and $CO_2$ uptake/growth (Kramer 1983 Water Relations of Plants, Academic Press p 405). WUE has been defined and measured in multiple ways. One approach is to calculate the ratio of whole plant dry weight, to the weight of water consumed by the plant throughout it's life (Chu et al 1992 Oecologia 89:580). Another variation is to use a shorter time interval when biomass accumulation and water use are measured (Mian et al 1998 Crop Sci. 38:390). Often measurements from restricted parts of the plant are used, for example, measuring only aerial growth and water use (Nienhuis et al 1994 Amer J Bot 81:943). WUE has also been defined as the ratio of $CO_2$ uptake to water vapor loss from a leaf or portion of a leaf, often measured over a very short time period (seconds/minutes) (Kramer 1983 Water Relations of Plants, Academic Press p 406). The ratio of $^{13}C/^{12}C$ fixed in plant tissue, and measured with an isotope ratio mass-spectrometer, has also been used to estimate WUE in plants using $C_3$ photosynthesis (Martin et al 1999 Crop Sci. 1775).

An increase in WUE is informative about the relatively improved efficiency of growth and water consumption, but on it's own it doesn't describe which of these two processes (or both) have changed. In selecting traits for improving crops, an increase in WUE due to a decrease in water use, without a change in growth would have particular merit in an irrigated agricultural system where the water input costs were high. An increase in WUE driven mainly by an increase in growth without a corresponding jump in water use would have applicability to all agricultural systems. In many agricultural systems where water supply is not limiting, an increase in growth, even if it came at the expense of an increased water use (i.e. no change in WUE), could also increase yield. Therefore new methods to increase both WUE and biomass accumulation are required to improve agricultural productivity. As WUE integrates many physiological processes relating to primary metabolism and water use, it is typically a highly polygenic trait with a large genotype by environment interaction (Richards et al 2002 Crop Sci 42:111). For these and other reasons few attempts to select for WUE changes in traditional breeding programs have been successful.

There is a need, therefore, to identify genes expressed in stress tolerant plants and plants that are efficient in water use that have the capacity to confer stress tolerance and water use efficiency to its host plant and to other plant species. Newly generated stress tolerant plants will have many advantages, such as an increased range in which the crop plants can be cultivated, by for example, decreasing the water requirements of a plant species. Other desirable advantages include increased resistance to lodging, the bending of shoots or stems in response to wind, rain, pests, or disease.

SUMMARY OF THE INVENTION

This invention fulfills in part the need to identify new, unique sequences capable of conferring stress tolerance to plants upon over-expression. The present invention describes a novel genus of Lectin-like Protein Kinase Stress-Related Polypeptides (LPKSRPs) and LPKSRP coding nucleic acids that are important for modulating a plant's response to an environmental stress. More particularly, overexpression of these LPKSRP coding nucleic acids in a plant results in the plant's increased growth and/or increased tolerance to an environmental stress.

Therefore, the present invention includes an isolated plant cell comprising an LPKSRP coding nucleic acid, wherein expression of the nucleic acid sequence in the plant cell results in increased growth and/or increased tolerance to an environmental stress as compared to a wild type variety of the plant cell. Preferably, the LPKSRP is from *Physcomitrella patens*. Namely, described herein is the *Physcomitrella patens* Lectin-like Protein Kinase-1 (PpLLPK-1).

The invention provides in some embodiments that the LPKSRP and coding nucleic acid are those that are found in members of the genus *Physcomitrella*. In another preferred embodiment, the nucleic acid and polypeptide are from a *Physcomitrella patens* plant. In one embodiment, the invention provides that plants overexpressing the LPKSRP demonstrate an increase in growth. In a preferred embodiment, the increase in plant growth is due to the plant's increase in Water Use Efficiency (WUE), as compared to a wild-type variety of the plant. In another preferred embodiment, the invention provides that plants overexpressing the LPKSRP demonstrate increased plant Dry Weight (DW), as compared to a wild-type variety of the plant. In another embodiment, the invention provides that plants overexpressing the LPKSRP demonstrate increased tolerance to an environmental stress, as compared to a wild-type variety of the plant. The invention provides that the environmental stress can be salinity, drought, temperature, metal, chemical, pathogenic and oxidative stresses, or combinations thereof. In preferred embodiments, the environmental stress can be selected from one or more of the group consisting of drought, high salt, and low temperature.

The invention further provides a seed produced by a transgenic plant transformed by an LPKSRP coding nucleic acid, wherein the plant is true breeding for increased growth and/or increased tolerance to an environmental stress as compared to a wild type variety of the plant. In a preferred embodiment, the LPKSRP coding nucleic acid is as described below.

The invention further provides an agricultural product produced by any of the below-described transgenic plants, plant parts, or seeds. The invention further provides an isolated LPKSRP as described below. The invention further provides an isolated LPKSRP coding nucleic acid, wherein the LPKSRP coding nucleic acid codes for an LPKSRP as described below.

The invention further provides an isolated recombinant expression vector comprising an LPKSRP coding nucleic acid as described below, wherein expression of the vector in a host cell results in the plant's increased growth and/or increased tolerance to an environmental stress as compared to a wild type variety of the host cell. The invention further provides a host cell containing the vector and a plant containing the host cell.

The invention further provides a method of producing a transgenic plant with an LPKSRP coding nucleic acid, wherein expression of the nucleic acid in the plant results in the plant's increased growth and/or increased tolerance to an environmental stress as compared to a wild type variety of the plant comprising: (a) transforming a plant cell with an expression vector comprising an LPKSRP coding nucleic acid; and (b) generating from the plant cell a transgenic plant with increased growth and/or an increased tolerance to an environmental stress as compared to a wild type variety of the plant. In preferred embodiments, the LPKSRP and LPKSRP coding nucleic acid are as described below.

The present invention further provides a method of identifying a novel LPKSRP, comprising (a) raising a specific antibody response to an LPKSRP, or fragment thereof, as described below; (b) screening putative LPKSRP material with the antibody, wherein specific binding of the antibody to the material indicates the presence of a potentially novel LPKSRP; and (c) identifying from the bound material a novel LPKSRP in comparison to known LPKSRP. Alternatively, hybridization with nucleic acid probes as described below can be used to identify novel LPKSRP nucleic acids.

The present invention also provides methods of modifying the growth and/or stress tolerance of a plant comprising, modifying the expression of an LPKSRP nucleic acid in the plant, wherein the LPKSRP is as described below. The invention provides that this method can be performed such that the plant's growth and/or stress tolerance is either increased or decreased. Preferably, the plant's growth and/or stress tolerance is increased in a plant via increasing expression of an LPKSRP nucleic acid.

BRIEF DESCRIPTION OF THE DRAWINGS

FIG. 1 shows the cDNA sequence of PpLLPK-1 from *Physcomitrella patens*.

FIG. 2 shows the deduced amino acid sequence of PpLLPK-1 from *Physcomitrella patens*.

FIG. 3 shows an alignment of the amino acid sequence of the disclosed *Physcomitrella patens* lectin-like protein kinase PpLLPK-1 with the amino acid sequences of five known protein kinases. The figure also indicates the consensus sequence of a lectin-like protein kinase based on the aligned sequences. White font on black are consensus residues derived from a block of similar residues at a given position. Black font on gray are consensus or similar amino acids at a position with a consensus of residues in at least 50% of the sequences. Non-similar residues at a given position are identified as black font on white.

FIG. 4 shows an alignment of the amino acid sequence of the disclosed *Physcomitrella patens* lectin-like protein kinase PpLLPK-1 with five amino acid sequences identified in a search of a patent sequence database. The figure also indicates the consensus sequence of a lectin-like protein kinase based on the aligned sequences. White font on black are consensus residues derived from a block of similar residues at a given position. Black font on gray are consensus or similar amino acids at a position with a consensus of residues in at least 50% of the sequences. Non-similar residues at a given position are identified as black font on white.

FIG. 5 shows Table 7, the vector-only control plants under well-watered and drought-cycling conditions.

FIG. 6 shows the promoter DNA sequence for constitutive expression in rice.

DETAILED DESCRIPTION OF THE INVENTION

Figure 7:
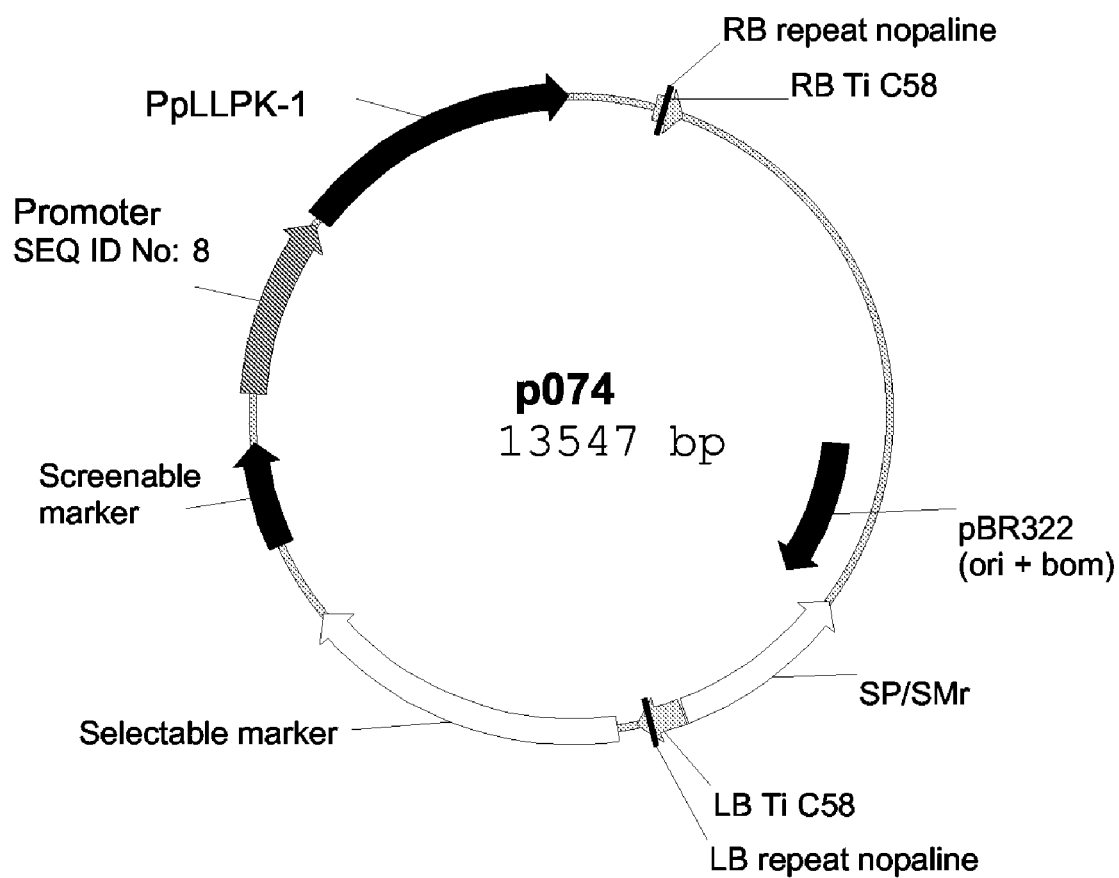
FIG. 7 shows the expression vector pO74 for constitutive expression in rice.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as polypeptide "Lectin-like Protein Kinase Stress-Related Polypeptides" (LPKSRPs), in no way limits the functionality of those sequences.

The present invention describes a novel genus of LPKSRPs and LPKSRP coding nucleic acids that are important for modulating a plant's growth and/or response to an environmental stress. More particularly, overexpression of these LPKSRP coding nucleic acids in a plant results in the plant's increased growth and/or increased tolerance to an environmental stress. A representative member of the LPKSRP genus is PpLLPK-1. In a preferred embodiment, all members of the genus are biologically active lectin-like protein kinases.

Accordingly, the present invention encompasses LPKSRP polynucleotide and polypeptide sequences and their use for increasing a plant's growth and/or tolerance to an environmental stress. In one embodiment, the LPKSRP sequences are from a plant, preferably a *Physcomitrella* plant, and more preferably a *Physcomitrella patens* plant. In another embodiment, the LPKSRP sequences include PpLLPK-1 (SEQ ID NOS:1 and 2). The disclosed *Physcomitrella patens* LPKSRP amino acid sequence has significant percent identity to known lectin-like protein kinases as is indicated below.

The present invention provides a transgenic plant cell transformed by an LPKSRP coding nucleic acid, wherein expression of the nucleic acid sequence in the plant cell results in the plant's increased growth and/or increased tolerance to an environmental stress as compared to a wild type variety of the plant cell. The invention further provides transgenic plant parts and transgenic plants containing the plant cells described herein. Plant parts include, but are not limited to, stems, roots, ovules, stamens, leaves, embryos, meristematic regions, callus tissue, gametophytes, sporophytes, pollen, microspores, and the like. In one embodiment, the transgenic plant is male sterile. Also provided is a plant seed produced by a transgenic plant transformed by an LPKSRP coding nucleic acid, wherein the seed contains the LPKSRP coding nucleic acid, and wherein the plant is true breeding for increased growth and/or increased tolerance to an environmental stress as compared to a wild type variety of the plant. The invention further provides a seed produced by a transgenic plant expressing an LPKSRP, wherein the seed contains the LPKSRP, and wherein the plant is true breeding for increased growth and/or increased tolerance to an environmental stress as compared to a wild type variety of the plant. The invention also provides an agricultural product produced by any of the below-described transgenic plants, plant parts, and plant seeds. Agricultural products include, but are not limited to, plant extracts, proteins, amino acids, carbohydrates, fats, oils, polymers, vitamins, and the like.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* LPKSRP PpLLPK-1 is useful for increasing a plant's growth and/or tolerance to an environmental stress. As used herein, the term polypeptide refers to a chain of at least four amino acids joined by peptide bonds. The chain may be linear, branched, circular, or combinations thereof. Accordingly, the present invention provides isolated LPKSRPs selected from PpLLPK-1, and homologs thereof. In preferred embodiments, the LPKSRP includes the *Physcomitrella patens* Lectin-like Protein Kinase-1 (PPLLPK-1) polypeptide as defined in SEQ ID NO:2; and homologs and orthologs thereof. Homologs and orthologs of the amino acid sequences are defined below.

The LPKSRPs of the present invention are preferably produced by recombinant DNA techniques. For example, a nucleic acid molecule encoding the polypeptide is cloned into an expression vector (as described below), the expression vector is introduced into a host cell (as described below), and the LPKSRP is expressed in the host cell. The LPKSRP can then be isolated from the cells by an appropriate purification scheme using standard polypeptide purification techniques. For the purposes of the invention, the term "recombinant polynucleotide" refers to a polynucleotide that has been altered, rearranged, or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, an LPKSRP, or peptide thereof, can be synthesized chemically using standard peptide synthesis techniques. Moreover, native LPKSRP can be isolated from cells (e.g. *Physcomitrella patens* cells), for example using an anti-LPKSRP antibody, which can be produced by standard techniques utilizing an LPKSRP or fragment thereof.

As used herein, the term "environmental stress" refers to sub-optimal conditions associated with salinity, drought, temperature, metal, chemical, pathogenic, and oxidative stresses, or combinations thereof. In preferred embodiments, the environmental stress can be selected from one or more of the group consisting of salinity, drought, or temperature, or combinations thereof, and in particular, can be selected from one or more of the group consisting of high salinity, low water content, or low temperature. It is also to be understood that as used in the specification and in the claims, "a" or "an" can mean one or more, depending upon the context in which it is used. Thus, for example, reference to "a cell" can mean that at least one cell can be utilized. As also used herein, the term "water use efficiency" refers to the amount of organic matter produced by a plant divided by the amount of water used by the plant in producing it, i.e. the dry weight of a plant in relation to the plant's water use. As used herein, the term "dry weight" refers to everything in the plant other than water, and includes, for example, carbohydrates, proteins, oils, and mineral nutrients.

As also used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences, which naturally flank the nucleic acid (i.e. sequences located at the 5' and 3' ends of the nucleic acid) in its naturally occurring replicon. For example, a cloned nucleic acid is considered isolated. In various embodiments, the isolated LPKSRP nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a *Physcomitrella patens* cell). A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized. Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule having a nucleotide sequence of SEQ ID NO:1, or a portion thereof, can be isolated using standard molecular biology techniques and the sequence information provided herein. For example, a *P. patens* LPKSRP cDNA can be isolated from a *P. patens* library using all or a portion of one of the sequences disclosed herein. Moreover, a nucleic acid molecule encompassing all or a portion of the sequence of SEQ ID NO:1, can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979, Biochemistry 18:5294-5299), and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence shown in SEQ ID NO:1. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to an LPKSRP nucleotide sequence can be prepared by standard synthetic techniques, e.g., using an automated DNA synthesizer.

In one embodiment, an isolated nucleic acid molecule of the invention comprises the nucleotide sequence shown in SEQ ID NO:1. The nucleic acid molecules of the pre-sent invention may comprise sequences encoding the LPKSRPs, (i.e., the "coding region"), as well as 5' untranslated sequences and 3' untranslated sequences. Alternatively, the nucleic acid molecules of the present invention can comprise only the coding region of the sequence in SEQ ID NO:1, or can contain whole genomic fragments isolated from genomic DNA. The present invention also includes LPKSRP coding nucleic acids that encode LPKSRPs as described herein. In a preferred embodiment, the LPKSRP coding nucleic acid encodes a PpLLPK-1 as defined in SEQ ID NO:2.

Moreover, the nucleic acid molecule of the invention can comprise a portion of the coding region of SEQ ID NO:1, for example, a fragment that can be used as a probe or primer or a fragment encoding a biologically active portion of an LPKSRP. The nucleotide sequences determined from the cloning of the LPKSRP genes from *Physcomitrella patens* allow for the generation of probes and primers designed for use in identifying and/or cloning LPKSRP homologs in other cell types and organisms, as well as LPKSRP homologs from other mosses and related species. The portion of the coding region can also encode a biologically active fragment of an LPKSRP.

As used herein, the term "biologically active portion of" an LPKSRP is intended to include a portion, e.g., a domain/motif, of an LPKSRP that participates in modulation of plant growth and/or stress tolerance in a plant. For the purposes of the present invention, modulation of plant growth and/or stress tolerance refers to at least a 10% increase or decrease in the growth and/or stress tolerance of a transgenic plant comprising an LPKSRP expression cassette (or expression vector) as compared to the growth and/or stress tolerance of a non-transgenic control plant. Methods for quantitating growth and/or stress tolerance are provided at least in Example 7 below. In a preferred embodiment, the biologically active portion of an LPKSRP increases a plant's growth and/or tolerance to an environmental stress.

Biologically active portions of an LPKSRP include peptides comprising amino acid sequences derived from the amino acid sequence of an LPKSRP, e.g., an amino acid sequence of SEQ ID NO: 2, or the amino acid sequence of a polypeptide identical to an LPKSRP, which include fewer amino acids than a full length LPKSRP or the full length polypeptide which is identical to an LPKSRP, and exhibit at least one activity of an LPKSRP. Typically, biologically active portions (e.g., peptides which are, for example, 5, 10, 15, 20, 30, 35, 36, 37, 38, 39, 40, 50, 100, or more amino acids in length) comprise a domain or motif with at least one activity of an LPKSRP. Moreover, other biologically active portions, in which other regions of the polypeptide are deleted, can be prepared by recombinant techniques and evaluated for one or more of the activities described herein. Preferably, the biologically active portion of an LPKSRP includes one or more selected domains/motifs, or portions thereof, having biological activity such as the conserved central kinase domain as is shown in FIG. 3. In one embodiment, the "central kinase domain" comprises residues at positions 235-546 of SEQ ID NO:2. In a preferred embodiment, the conserved central kinase domain comprises four conserved regions, wherein the first region commences with a tyrosine residue at position 1 and has a leucine at position 3, a glycine residue at position 4, a glycine residue at position 8, a glycine residue at position 10, a phenylalanine residue at position 12, a glycine residue at position 13, and a threonine residue at position 15; the second region is downstream from the first region, commences with an alanine residue at position 1, and has a lysine residue at position 3, an isoleucine residue at position 5, a lysine residue at position 7, a glutamic acid residue at position 17, an aspartic acid residue at position 18, a valine residue at position 19, an arginine residue at position 21, a glutamic acid residue at position 22, an isoleucine residue at position 25, a leucine residue at position 29, a glycine residue at position 31, an asparagine residue at position 34, a valine residue at position 36, a glutamic acid residue at position 43, an aspartic acid residue at position 44, a valine residue at positions 48 and 51, a methionine residue at position 52, a glutamic acid residue at position 53, a leucine residue at position 54, a cysteine residue at position 55, a glycine residue at positions 57 and 58, a glutamic acid residue at position 59, a leucine residue at position 60, an aspartic acid residue at position 62, an arginine residue at position 63, and an isoleucine residue at position 64; the third region is downstream from the second region, commences with a tyrosine residue at position 1, and has a serine residue at position 2, a glutamic acid residue at position 3, an alanine residue at position 6, an arginine residue at position 11, a valine residue at position 16, a cysteine residue at position 20, a histidine residue at position 21, a glycine residue at position 24, a valine residue at position 25, a histidine residue at position 27, an arginine residue at position 28, an aspartic acid residue at position 29, a lysine residue at position 31, a proline residue at position 32, a glutamic acid residue at position 33, an asparagine residue at position 34, a phenylalanine residue at position 35, an leucine residue at positions 36 and 46, a lycine residue at position 47, an aspartic acid residue at position 50, a phenylalanine residue at position 51, a glycine residue at position 52, a leucine residue at position 53, a serine residue at position 54, a proline residue at position 59, an aspartic acid residue at position 65, a valine residue at position 67, a glycine residue at position 68, a serine residue at position 69, a tyrosine residue at positions 71 and 72, a valine residue at position 73, an alanine residue at position 74, a proline residue at position 75, a glutamic acid residue at position 76, a valine residue at position 77, a leucine residue at position 78, a glutamic acid residue at position 85, an aspartic acid residue at position 87, a valine residue at position 88, a tryptophan residue at position 89, a serine residue at position 90, a glycine residue at position 92, a valine residue at position 93, an isoleucine residue at position 94, a tyrosine residue at position 96, an isoleucine residue at position 97, a leucine residue at positions 98 and 99, a glycine residue at position 101, a proline residue at position 104, a phenylalanine residue at position 105, a tryptophan residue at position 106, a threonine residue at position 109, a glutamic acid residue at position 110, an isoleucine residue at position 113, a phenylalanine residue at position 114, a proline residue at position 128, a tryptophan residue at position 129, a proline residue at position 130, an isoleucine residue at position 132, a serine residue at position 133, an alanine residue at position 136, a lysine residue at position 137, an aspartic acid residue at position 138, a leucine residue at position 144, an arginine residue at position 151, an alanine residue at position 154, a leucine residue at position 158, a histidine residue at position 160, a proline residue at position 161, and a tryptophan residue at position 162; and the fourth region is downstream from the third region, commences with a proline residue at position 1, and has an aspartic acid residue at position 3, a valine residue at position 6, an alanine residue at position 23, a leucine residue at positions 31 and 39, a phenylalanine residue at position 43, a glycine residue at position 52, a leucine residue at position 63, and a lysine residue at position 65.

The invention also provides LPKSRP chimeric or fusion polypeptides. As used herein, an LPKSRP "chimeric polypeptide" or "fusion polypeptide" comprises an LPKSRP operatively linked to a non-LPKSRP. AN LPKSRP refers to a polypeptide having an amino acid sequence corresponding to an LPKSRP, whereas a non-LPKSRP refers to a polypeptide having an amino acid sequence corresponding to a polypeptide which is not substantially identical to the LPKSRP, e.g., a polypeptide that is different from the LPKSRP and is derived from the same or a different organism. With respect to the fusion polypeptide, the term "operatively linked" is intended to indicate that the LPKSRP and the non-LPKSRP are fused to each other so that both sequences fulfill the proposed function attributed to the sequence used. The non-LPKSRP can be fused to the N-terminus or C-terminus of the LPKSRP. For example, in one embodiment, the fusion polypeptide is a GST-LPKSRP fusion polypeptide in which the LPKSRP sequences are fused to the C-terminus of the GST sequences. Such fusion polypeptides can facilitate the purification of recombinant LPKSRPs. In another embodiment, the fusion polypeptide is an LPKSRP containing a heterologous signal sequence at its N-terminus. In certain host cells (e.g., mammalian host cells), expression and/or secretion of an LPKSRP can be increased through use of a heterologous signal sequence.

Preferably, an LPKSRP chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (See, for example, Current Protocols in Molecular Biology, Eds. Ausubel et al. John Wiley & Sons: 1992). Moreover, many expression vectors are commercially available that already encode a fusion moiety (e.g., a GST polypeptide). AN LPKSRP encoding nucleic acid can be cloned into such an expression vector such that the fusion moiety is linked in-frame to the LPKSRP.

In addition to fragments and fusion polypeptides of the LPKSRPs described herein, the present invention includes homologs and analogs of naturally occurring LPKSRPs and LPKSRP encoding nucleic acids in a plant. "Homologs" are defined herein as two nucleic acids or polypeptides that have similar, or "identical," nucleotide or amino acid sequences, respectively. Homologs include allelic variants, orthologs, paralogs, agonists, and antagonists of LPKSRPs as defined hereafter. The term "homolog" further encompasses nucleic acid molecules that differ from the nucleotide sequence shown in SEQ ID NO:1 (and portions thereof due to degeneracy of the genetic code and thus encode the same LPKSRP as that encoded by the nucleotide sequence shown in SEQ ID NO:1. As used herein, a "naturally occurring" LPKSRP refers to an LPKSRP amino acid sequence that occurs in nature. Preferably, a naturally occurring LPKSRP comprises an amino acid sequence as defined in SEQ ID NO:2.

An agonist of the LPKSRP can retain substantially the same, or a subset, of the biological activities of the LPKSRP. An antagonist of the LPKSRP can inhibit one or more of the activities of the naturally occurring form of the LPKSRP.

Nucleic acid molecules corresponding to natural allelic variants and analogs, orthologs, and paralogs of an LPKSRP cDNA can be isolated based on their identity to the *Physcomi-trella patens* LPKSRP nucleic acids described herein using LPKSRP cDNAs, or a portion thereof, as a hybridization probe according to standard hybridization techniques under stringent hybridization conditions. In an alternative embodiment, homologs of the LPKSRP can be identified by screening combinatorial libraries of mutants, e.g., truncation mutants, of the LPKSRP for LPKSRP agonist or antagonist activity. In one embodiment, a variegated library of LPKSRP variants is generated by combinatorial mutagenesis at the nucleic acid level and is encoded by a variegated gene library. A variegated library of LPKSRP variants can be produced by, for example, enzymatically ligating a mixture of synthetic oligonucleotides into gene sequences such that a degenerate set of potential LPKSRP sequences is expressible as individual polypeptides, or alternatively, as a set of larger fusion polypeptides (e.g., for phage display) containing the set of LPKSRP sequences therein. There are a variety of methods that can be used to produce libraries of potential LPKSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential LPKSRP sequences. Methods for synthesizing degenerate oligonucleotides are known in the art (See, e.g., Narang, S. A., 1983, Tetrahedron 39:3; Itakura et al., 1984, Annu. Rev. Biochem. 53:323; Itakura et al., 1984, Science 198:1056; Ike et al., 1983, Nucleic Acid Res. 11:477).

In addition, libraries of fragments of the LPKSRP coding regions can be used to generate a variegated population of LPKSRP fragments for screening and subsequent selection of homologs of an LPKSRP. In one embodiment, a library of coding sequence fragments can be generated by treating a double stranded PCR fragment of an LPKSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal, and internal fragments of various sizes of the LPKSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of LPKSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify LPKSRP homologs (Arkin and Yourvan, 1992, PNAS 89:7811-7815; Delgrave et al., 1993, Polypeptide Engineering 6(3): 327-331). In another embodiment, cell based assays can be exploited to analyze a variegated LPKSRP library, using methods well known in the art.

The present invention further provides a method of identifying a novel LPKSRP, comprising (a) raising a specific antibody response to an LPKSRP, or a fragment thereof, as described herein; (b) screening putative LPKSRP material with the antibody, wherein specific binding of the antibody to the material indicates the presence of a potentially novel LPKSRP; and (c) analyzing the bound material in comparison to known LPKSRP, to determine its novelty.

As stated above, the present invention includes LPKSRPs and homologs thereof. To determine the percent sequence identity of two amino acid sequences (e.g., the sequence of SEQ ID NO: 2, and a mutant form thereof, the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., the sequence of SEQ ID NO: 2) is occupied by the same amino acid residue as the corresponding position in the other sequence (e.g., a mutant form of the sequence of SEQ ID NO:2), then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO: 2. In another embodiment, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence encoded by a nucleic acid sequence shown in SEQ ID NO: 1. In other embodiments, the LPKSRP amino acid homologs have sequence identity over at least 15 contiguous amino acid residues, more preferably at least 25 contiguous amino acid residues, and most preferably at least 35 contiguous amino acid residues of SEQ ID NO: 2. Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to the central protein kinase domain of the disclosed amino acid sequences shown as residues 235 to 546 of SEQ ID NO: 2. In another embodiment, the isolated amino acid homolog of the present invention is encoded by a nucleic acid as defined by nucleotides at positions 736 to 1671 of SEQ ID NO: 1.

In another preferred embodiment, an isolated nucleic acid homolog of the invention comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence shown in SEQ ID NO: 1, or to a portion comprising at least 60 consecutive nucleotides thereof. The preferable length of sequence comparison for nucleic acids is at least 75 nucleotides, more preferably at least 100 nucleotides, and most preferably the entire length of the coding region. It is more preferable that the nucleic acid homologs encode polypeptides having homology with SEQ ID NO: 2 over the central kinase domain.

It is further preferred that the isolated nucleic acid homolog of the invention encodes an LPKSRP, or portion thereof, that is at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO: 2 and that functions as a modulator of plant growth and/or an environmental stress response in a plant. In a more preferred embodiment, overexpression of the nucleic acid homolog in a plant increases the plant's growth and/or the tolerance of the plant to an environmental stress. In a further preferred embodiment, the nucleic acid homolog encodes an LPKSRP that functions as a lectin-like protein kinase.

For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap-opening penalty of 15 and a gap extension penalty of 6.66 are used for determining the percent identity of two nucleic acids. A gap-opening penalty of 10 and a gap extension penalty of 0.1 are used for determining the percent identity of two polypeptides. All other parameters are set at the default settings. For purposes of a multiple alignment (Clustal W algorithm), the gap-opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to the polynucleotide of SEQ ID NO: 1 under stringent conditions. More particularly, an isolated nucleic acid molecule of the invention is at least 15 nucleotides in length and hybridizes under stringent conditions to the nucleic acid molecule comprising a nucleotide sequence of SEQ ID NO: 1. In other embodiments, the nucleic acid is at least 30, 50, 100, 250, or more nucleotides in length. Preferably, an isolated nucleic acid homolog of the invention comprises a nucleotide sequence which hybridizes under highly stringent conditions to the nucleotide sequence shown in SEQ ID NO: 1 and functions as a modulator of growth and/or stress tolerance in a plant. In a further preferred embodiment, overexpression of the isolated nucleic acid homolog in a plant increases a plant's growth and/or tolerance to an environmental stress. In an even further preferred embodiment, the isolated nucleic acid homolog encodes an LPKSRP that functions as a lectin-like protein kinase.

As used herein with regard to hybridization for DNA to a DNA blot, the term "stringent conditions" refers to hybridization overnight at 60° C. in 10× Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. In another embodiment, the phrase "stringent conditions" refers to hybridization in a 6×SSC solution at 65° C. As also used herein, "highly stringent conditions" refers to hybridization overnight at 65° C. in 10× Denharts solution, 6×SSC, 0.5% SDS, and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Meinkoth and Wahl, 1984, Anal. Biochem. 138:267-284; Current Protocols in Molecular Biology, Chapter 2, Ausubel et al. Eds., Greene Publishing and Wiley-Interscience, New York, 1995; and Tijssen, 1993, Laboratory Techniques in Biochemistry and Molecular Biology: Hybridization with Nucleic Acid Probes, Part I, Chapter 2, Elsevier, New York, 1993. Preferably, an isolated nucleic acid molecule of the invention that hybridizes under stringent or highly stringent conditions to a sequence of SEQ ID NO: 1 corresponds to a naturally occurring nucleic acid molecule. As used herein, a "naturally occurring" nucleic acid molecule refers to an RNA or DNA molecule having a nucleotide sequence that occurs in nature (e.g., encodes a natural polypeptide). In one embodiment, the nucleic acid encodes a naturally occurring *Physcomitrella patens* LPKSRP.

Using the above-described methods, and others known to those of skill in the art, one of ordinary skill in the art can isolate homologs of the *Physcomitrella patens* LPKSRP comprising an amino acid sequence as shown in SEQ ID NO: 2. One subset of these homologs is allelic variants. As used herein, the term "allelic variant" refers to a nucleotide sequence containing polymorphisms that lead to changes in the amino acid sequences of an LPKSRP and that exist within a natural population (e.g., a plant species or variety). Such natural allelic variations can typically result in 1-5% variance in an LPKSRP nucleic acid. Allelic variants can be identified by sequencing the nucleic acid sequence of interest in a number of different plants, which can be readily carried out by using hybridization probes to identify the same LPKSRP genetic locus in those plants. Any and all such nucleic acid variations and resulting amino acid polymorphisms or variations in an LPKSRP that are the result of natural allelic variation and that do not alter the functional activity of an LPKSRP, are intended to be within the scope of the invention.

Moreover, nucleic acid molecules encoding LPKSRPs from the same or other species such as LPKSRP analogs, orthologs, and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation.

Normally, orthologs encode polypeptides having the same or similar functions. As also used herein, the term "paralogs" refers to two nucleic acids that are related by duplication within a genome. Paralogs usually have different functions, but these functions may be related (Tatusov, R. L. et al., 1997, Science 278(5338): 631-637). Analogs, orthologs, and paralogs of a naturally occurring LPKSRP can differ from the naturally occurring LPKSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably, 85-90% or 90-95%, and most preferably 95%, 96%, 97%, 98%, or even 99% identity, or 100% sequence identity, with all or part of a naturally occurring LPKSRP amino acid sequence, and will exhibit a function similar to an LPKSRP. Preferably, an LPKSRP ortholog of the present invention functions as a modulator of plant growth and/or an environmental stress response in a plant and/or functions as a lectin-like protein kinase. More preferably, an LPKSRP ortholog increases the growth under water-limited conditions and/or increases the stress tolerance of a plant.

In addition to naturally-occurring variants of an LPKSRP sequence that may exist in the population, the skilled artisan will further appreciate that changes can be introduced by mutation into a nucleotide sequence of SEQ ID NO: 1, thereby leading to changes in the amino acid sequence of the encoded LPKSRP, without altering the functional activity of the LPKSRP. For example, nucleotide substitutions leading to amino acid substitutions at "non-essential" amino acid residues can be made in a sequence of SEQ ID NO: 1. A "non-essential" amino acid residue is a residue that can be altered from the wild-type sequence of one of the LPKSRPs without altering the activity of said LPKSRP, whereas an "essential" amino acid residue is required for LPKSRP activity. Other amino acid residues, however, (e.g., those that are not conserved or only semi-conserved in the domain having LPKSRP activity) may not be essential for activity and thus are likely to be amenable to alteration without altering LPKSRP activity.

Accordingly, another aspect of the invention pertains to nucleic acid molecules encoding LPKSRPs that contain changes in amino acid residues that are not essential for LPKSRP activity. Such LPKSRPs differ in amino acid sequence from a sequence contained in SEQ ID NO: 2, yet retain at least one of the LPKSRP activities described herein. In one embodiment, the isolated nucleic acid molecule comprises a nucleotide sequence encoding a polypeptide, wherein the polypeptide comprises an amino acid sequence at least about 50% identical to the central protein kinase region of an amino acid sequence of SEQ ID NO: 2. Preferably, the polypeptide encoded by the nucleic acid molecule is at least about 50-60% identical to the central protein kinase region of one of the sequences of SEQ ID NO: 2, more preferably at least about 60-70% identical to the central protein kinase region of one of the sequences of SEQ ID NO: 2, even more preferably at least about 70-75%, 75-80%, 80-85%, 85-90%, or 90-95% identical to the central protein kinase region of one of the sequences of SEQ ID NO: 2, and most preferably at least about 96%, 97%, 98%, or 99% identical to the central protein kinase region of SEQ ID NO: 2. In another embodiment, the polypeptide encoded by the nucleic acid molecule is at least about 50-60% identical to the sequence of SEQ ID NO: 2, more preferably at least about 60-70% identical to the sequence of SEQ ID NO: 2, even more preferably at least about 70-75%, 75-80%, 80-85%, 85-90%, or 90-95% identical to the sequence of SEQ ID NO: 2, and most preferably at least about 96%, 97%, 98%, or 99% identical to the sequence of SEQ ID NO: 2. The preferred LPKSRP homologs of the present invention preferably participate in plant growth and/or the stress tolerance response in a plant, or more particularly, function as a lectin-like protein kinase.

An isolated nucleic acid molecule encoding an LPKSRP having sequence identity with a polypeptide sequence of SEQ ID NO: 2 can be created by introducing one or more nucleotide substitutions, additions, or deletions into a nucleotide sequence of SEQ ID NO: 1, respectively, such that one or more amino acid substitutions, additions, or deletions are introduced into the encoded polypeptide. Mutations can be introduced into the sequence of SEQ ID NO: 1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in an LPK-SRP is preferably replaced with another amino acid residue from the same side chain family. Alternatively, in another embodiment, mutations can be introduced randomly along all or part of an LPKSRP coding sequence, such as by saturation mutagenesis, and the resultant mutants can be screened for an LPKSRP activity described herein to identify mutants that retain LPKSRP activity. Following mutagenesis of one of the sequences of SEQ ID NO: 1, the encoded polypeptide can be expressed recombinantly and the activity of the polypeptide can be determined by analyzing the growth and/or stress tolerance of a plant expressing the polypeptide as described in Example 7.

Additionally, optimized LPKSRP nucleic acids can be created. Preferably, an optimized LPKSRP nucleic acid encodes an LPKSRP that modulates a plant's growth and/or modulates a plant's tolerance to an environmental stress, and more preferably increases a plant's growth and/or increases a plant's tolerance to an environmental stress upon its overexpression in the plant. As used herein, "optimized" refers to a nucleic acid that is genetically engineered to increase its expression in a given plant or animal. To provide plant optimized LPKSRP nucleic acids, the DNA sequence of the gene can be modified to 1) comprise codons preferred by highly expressed plant genes; 2) comprise an A+T content in nucleotide base composition to that substantially found in plants; 3) form a plant initiation sequence; or 4) to eliminate sequences that cause destabilization, inappropriate polyadenylation, degradation and termination of RNA, or that form secondary structure hairpins or RNA splice sites. Increased expression of LPKSRP nucleic acids in plants can be achieved by utilizing the distribution frequency of codon usage in plants in general or in a particular plant. Methods for optimizing nucleic acid expression in plants can be found in EPA 0359472; EPA 0385962; PCT Application No. WO 91/16432; U.S. Pat. Nos. 5,380,831; 5,436,391; Perlack et al., 1991, Proc. Natl. Acad. Sci. USA 88:3324-3328; and Murray et al., 1989, Nucleic Acids Res. 17:477-498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A = n=1 \ Z \ X_n - Y_n \ X_n$ times $100 \ Z$ where $X_n$=frequency of usage for codon n in the host cell; $Y_n$=frequency of usage for codon n in the synthetic gene; n represents an individual codon that specifies an amino acid; and the total number of codons is Z. The overall deviation of the frequency of codon usage, A, for all amino acids should preferably be less than about 25%, and more preferably less than about 10%.

Hence, an LPKSRP nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized LPKSRP nucleic acids of this invention also preferably have CG and TA doublet avoidance indices closely approximating those of the chosen host plant (e.g., *Physcomitrella patens, Brassica napus, Glycine max*, or *Oryza sativa*). More preferably these indices deviate from that of the host by no more than about 10-15%.

In addition to the nucleic acid molecules encoding the LPKSRPs described above, another aspect of the invention pertains to isolated nucleic acid molecules that are anti-sense thereto. Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide of SEQ ID NO: 2.

The antisense nucleic acid can be complementary to an entire LPKSRP coding strand, or to only a portion thereof. In one embodiment, an antisense nucleic acid molecule is antisense to a "coding region" of the coding strand of a nucleotide sequence encoding an LPKSRP. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding an LPKSRP. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of LPKSRP mRNA, but more preferably is an oligonucleotide that is antisense to only a portion of the coding or noncoding region of LPKSRP mRNA. For example, the antisense oligonucleotide can be complementary to the region surrounding the translation start site of LPKSRP mRNA. An antisense oligonucleotide can be, for example, about 5, 10, 15, 20, 25, 30, 35, 40, 45, or 50 nucleotides in length. Typically, the antisense molecules of the present invention comprise an RNA having 60-100% sequence identity with at least 14 consecutive nucleotides of SEQ ID NO: 1, or a polynucleotide encoding a polypeptide of SEQ ID NO: 2. Preferably, the sequence identity will be at least 70%, more preferably at least 75%, 80%, 85%, 90%, 95%, or 98%, and most preferably 99%. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987, Nucleic Acids. Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

The antisense nucleic acid molecules of the invention are typically administered to a cell or generated in situ such that they hybridize with or bind to cellular mRNA and/or genomic DNA encoding an LPKSRP to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of an LPKSRP polypeptide. As used herein, the term "ribozyme" refers to a catalytic RNA-based enzyme with ribonuclease activity that is capable of cleaving a single-stranded nucleic acid, such as an mRNA, to which it has a complementary region. Ribozymes (e.g., hammerhead ribozymes described in Haselhoff and Gerlach, 1988, Nature 334:585-591) can be used to catalytically cleave LPKSRP mRNA transcripts to thereby inhibit translation of LPKSRP mRNA. A ribozyme having specificity for an LPKSRP-encoding nucleic acid can be designed based upon the nucleotide sequence of an LPKSRP cDNA as disclosed herein (i.e., SEQ ID NO: 1) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in an LPKSRP-encoding mRNA. See, e.g., U.S. Pat. Nos. 4,987,071 and 5,116,742 to Cech et al. Alternatively, LPKSRP mRNA can be used to select a catalytic RNA having a specific ribonuclease activity from a pool of RNA molecules. See, e.g., Bartel, D. and Szostak, J. W., 1993, Science 261:1411-1418. In preferred embodiments, the ribozyme will contain a portion having at least 7, 8, 9, 10, 12, 14, 16, 18, or 20 nucleotides, and more preferably 7 or 8 nucleotides, that have 100% complementarity to a portion of the target RNA. Methods for making ribozymes are known to those skilled in the art. See, e.g., U.S. Pat. Nos. 6,025,167; 5,773,260; and 5,496,698.

The term "dsRNA," as used herein, refers to RNA hybrids comprising two strands of RNA. The dsRNAs can be linear or circular in structure. In a preferred embodiment, dsRNA is specific for a polynucleotide encoding either the polypeptide of SEQ ID NO: 2, or a polypeptide having at least 80% sequence identity with a polypeptide of SEQ ID NO: 2 over the central protein kinase domain. The hybridizing RNAs may be substantially or completely complementary. By "substantially complementary," is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides, ribonucleotide analogs such as 2'-O-methyl ribosyl residues, or combinations thereof. See, e.g., U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, e.g., U.S. Pat. No. 5,795,715. In one embodiment, dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et al., 1987, Science 238:645-650 and Cooney et al., 1988, Science 241: 456-459) and co-suppression (Napoli et al., 1990, The Plant Cell 2:279-289) are known in the art. Partial and full-length cDNAs have been used for the co-suppression of endogenous plant genes. See, e.g., U.S. Pat. Nos. 4,801,340, 5,034,323, 5,231,020, and 5,283,184; Van der Kroll et al., 1990, The Plant Cell 2:291-299; Smith et al., 1990, Mol. Gen. Genetics 224:477-481; and Napoli et al., 1990, The Plant Cell 2:279-289.

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95%, or more. The introduced sense polynucleotide need not be full length relative to the target gene or transcript. Preferably, the sense polynucleotide will have at least 65% sequence identity with at least 100 consecutive nucleotides of SEQ ID NO: 1. The regions of identity can comprise introns and/or exons and untranslated regions. The introduced sense polynucleotide may be present in the plant cell transiently, or may be stably integrated into a plant chromosome or extrachromosomal replicon.

Alternatively, LPKSRP gene expression can be inhibited by targeting nucleotide sequences complementary to the regulatory region of an LPKSRP nucleotide sequence (e.g., an LPKSRP promoter and/or enhancer) to form triple helical structures that pre-vent transcription of an LPKSRP gene in target cells. See generally, Helene, C., 1991, Anticancer Drug Des. 6(6):569-84; Helene, C. et al., 1992, Ann. N.Y. Acad. Sci. 660:27-36; and Maher, L. J., 1992, Bioassays 14(12): 807-15.

In addition to the LPKSRP nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of one of the sequences set forth in SEQ ID NO: 1; an anti-sense sequence of one of the sequences set forth in SEQ ID NO:1; or naturally occurring mutants thereof. Primers based on a nucleotide sequence of SEQ ID NO:1 can be used in PCR reactions to clone LPKSRP homologs. Probes based on the LPKSRP nucleotide sequences can be used to detect transcripts or genomic sequences encoding the same or substantially identical polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an LPKSRP, such as by measuring a level of an LPKSRP-encoding nucleic acid, in a sample of cells, e.g., detecting LPKSRP mRNA levels or determining whether a genomic LPKSRP gene has been mutated or deleted. In particular, a useful method to ascertain the level of transcription of the gene (an indicator of the amount of mRNA available for translation to the gene product) is to perform a Northern blot (For reference, see, for example, Ausubel et al., 1988, Current Protocols in Molecular Biology, Wiley: New York). The information from a Northern blot at least partially demonstrates the degree of transcription of the transformed gene. Total cellular RNA can be prepared from cells, tissues, or organs by several methods, all well-known in the art, such as that described in Bormann, E. R. et al., 1992, Mol. Microbiol. 6:317-326. To assess the presence or relative quantity of polypeptide translated from this mRNA, standard techniques, such as a Western blot, may be employed. These techniques are well known to one of ordinary skill in the art. (See, for example, Ausubel et al., 1988, Current Protocols in Molecular Biology, Wiley: New York).

The invention further provides an isolated recombinant expression vector comprising an LPKSRP nucleic acid as described above, wherein expression of the vector in a host cell results in increased growth and/or tolerance to environmental stress as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the pre-sent specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., LPKSRPs, mutant forms of LPKSRPs, fusion polypeptides, etc.).

The recombinant expression vectors of the invention can be designed for expression of LPKSRPs in prokaryotic or eukaryotic cells. For example, LPKSRP genes can be expressed in bacterial cells such as *C. glutamicum*, insect cells (using baculovirus expression vectors), yeast and other fungal cells (See Romanos, M. A. et al., 1992, Foreign gene expression in yeast: a review, Yeast 8:423-488; van den Hondel, C. A. M. J. J. et al., 1991, Heterologous gene expression in filamentous fungi, in: More Gene Manipulations in Fungi, J. W. Bennet & L. L. Lasure, eds., p. 396-428: Academic Press: San Diego; and van den Hondel, C. A. M. J. J. & Punt, P. J., 1991, Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999, Marine Biotechnology 1(3):239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in PCT Application No. WO 98/01572, and multicellular plant cells (See Schmidt, R. and Willmitzer, L., 1988, High efficiency *Agrobacterium tumefaciens*-mediated transformation of *Arabidopsis thaliana* leaf and cotyledon explants, Plant Cell Rep. 583-586; Plant Molecular Biology and Biotechnology, C Press, Boca Raton, Fla., chapter 6/7, S.71-119 (1993); F. F. White, B. Jenes et al., Techniques for Gene Transfer, in: Transgenic Plants, Vol. 1, Engineering and Utilization, eds. Kung und R. Wu, 128-43, Academic Press: 1993; Potrykus, 1991, Annu. Rev. Plant Physiol. Plant Molec. Biol. 42:205-225 and references cited therein), or mammalian cells. Suitable host cells are discussed further in Goeddel, Gene Expression Technology: Methods in Enzymology 185, Academic Press: San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc; Smith, D. B. and Johnson, K. S., 1988, Gene 67:31-40), pMAL (New England Biolabs, Beverly, Mass.), and pRIT5 (Pharmacia, Piscataway, N.J.) which fuse glutathione S-transferase (GST), maltose E binding polypeptide, or polypeptide A, respectively, to the target recombinant polypeptide. In one embodiment, the coding sequence of the LPKSRP is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant LPKSRP unfused to GST can be recovered by cleavage of the fusion polypeptide with thrombin.

Examples of suitable inducible non-fusion *E. coli* expression vectors include pTrc (Amann et al., 1988, Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident λ prophage harboring a T7 gn1 gene under the transcriptional control of the lacUV 5 promoter.

One strategy to maximize recombinant polypeptide expression is to express the polypeptide in a host bacteria with an impaired capacity to proteolytically cleave the recombinant polypeptide (Gottesman, S., Gene Expression Technology: Methods in Enzymology 185, Academic Press, San Diego, Calif. (1990) 119-128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992, Nucleic Acids Res. 20:2111-2118). Such alteration of nucleic acid sequences of the invention can be carried out by standard DNA synthesis techniques.

In another embodiment, the LPKSRP expression vector is a yeast expression vector. Examples of vectors for expression in yeast *S. cerevisiae* include pYepSec1 (Baldari, et al., 1987, EMBO J. 6:229-234), pMFa (Kurjan and Herskowitz, 1982, Cell 30:933-943), pJRY88 (Schultz et al., 1987, Gene 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J., 1991, "Gene transfer systems and vector development for filamentous fungi," in: Applied Molecular Genetics of Fungi, J. F. Peberdy, et al., eds., p. 1-28, Cambridge University Press: Cambridge.

Alternatively, the LPKSRPs of the invention can be expressed in insect cells using baculovirus expression vectors. Baculovirus vectors available for expression of polypeptides in cultured insect cells (e.g., Sf 9 cells) include the pAc series (Smith et al., 1983, Mol. Cell. Biol. 3:2156-2165) and the pVL series (Lucklow and Summers, 1989, Virology 170: 31-39).

In yet another embodiment, an LPKSRP nucleic acid of the invention is expressed in mammalian cells using a mammalian expression vector. Examples of mammalian expression vectors include pCDM8 (Seed, B., 1987, Nature 329:840) and pMT2PC (Kaufman et al., 1987, EMBO J. 6:187-195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. Molecular Cloning: A Laboratory Manual. latest ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268-277), lymphoid-specific promoters (Calame and Eaton, 1988, Adv. Immunol. 43:235-275), in particular promoters of T cell receptors (Winoto and Baltimore, 1989, EMBO J. 8:729-733), and immunoglobulins (Banerji et al., 1983, Cell 33:729-740; Queen and Baltimore, 1983, Cell 33:741-748), neuron-specific promoters (e.g., the neurofilament promoter; Byrne and Ruddle, 1989, PNAS 86:5473-5477), pancreas-specific promoters (Edlund et al., 1985, Science 230:912-916), and mammary gland-specific promoters (e.g., milk whey promoter; U.S. Pat. No. 4,873,316 and European Application Publication No. 264, 166). Developmentally-regulated promoters are also encompassed, for example, the murine hox promoters (Kessel and Gruss, 1990, Science 249:374-379) and the fetopolypeptide promoter (Campes and Tilghman, 1989, Genes Dev. 3:537-546).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics or herbicides) is generally introduced into the host cells along with the gene of interest. Preferred selectable markers include those that confer resistance to drugs, such as G418, hygromycin, and methotrexate, or in plants that confer resistance towards an herbicide such as glyphosate, glufosinate, or imidazolinone. Nucleic acid molecules encoding a selectable marker can be introduced into a host cell on the same vector as that encoding an LPKSRP or can be introduced on a separate vector. Cells stably transfected with the introduced nucleic acid molecule can be identified by, for example, herbicide selection (e.g., cells that have incorporated the selectable marker gene will survive, while the other cells die).

In a preferred embodiment of the present invention, the LPKSRPs are expressed in plants and plants cells such as unicellular plant cells (e.g. algae) (See Falciatore et al., 1999, Marine Biotechnology 1(3):239-251 and references therein) and plant cells from higher plants (e.g., the spermatophytes, such as crop plants). An LPKSRP may be "introduced" into a plant cell by any means, including transfection, transformation or transduction, electroporation, particle bombardment, agroinfection, and the like. One transformation method known to those of skill in the art is the dipping of a flowering plant into an *Agrobacteria* solution, wherein the *Agrobacteria* contain the LPKSRP nucleic acid, followed by breeding of the transformed gametes.

Other suitable methods for transforming or transfecting host cells including plant cells can be found in Sambrook, et al. (Molecular Cloning: A Laboratory Manual. latest ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As increased plant growth and/or biotic and abiotic stress tolerance are general traits wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses, and forage crops, these crop plants are also preferred target plants for a genetic engineering as one further embodiment of the present invention. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of an LPKSRP into a plant is achieved by *Agrobacterium* mediated gene transfer. *Agrobacterium* mediated plant transformation can be performed using for example the GV3101 (pMP90) (Koncz and Schell, 1986, Mol. Gen. Genet. 204: 383-396) or LBA4404 (Clontech) *Agrobacterium tumefaciens* strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl trans-formation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced LPKSRP may be maintained in the plant cell stably if it is incorporated into a non-chromosomal autonomous replicon or integrated into the plant chromosomes. Alternatively, the introduced LPKSRP may be present on an extra-chromosomal non-replicating vector and may be transiently expressed or transiently active.

In one embodiment, a homologous recombinant microorganism can be created wherein the LPKSRP is integrated into a chromosome, a vector is prepared which contains at least a portion of an LPKSRP gene into which a deletion, addition, or substitution has been introduced to thereby alter, e.g., functionally disrupt, the LPKSRP gene. Preferably, the LPKSRP gene is a *Physcomitrella patens* LPKSRP gene, but it can be a homolog from a related plant or even from a mammalian, yeast, or insect source. In one embodiment, the vector is designed such that, upon homologous recombination, the endogenous LPKSRP gene is functionally disrupted (i.e., no longer encodes a functional polypeptide; also referred to as a knock-out vector). Alternatively, the vector can be designed such that, upon homologous recombination, the endogenous LPKSRP gene is mutated or otherwise altered but still encodes a functional polypeptide (e.g., the upstream regulatory region can be altered to thereby alter the expression of the endogenous LPKSRP). To create a point mutation via homologous recombination, DNA-RNA hybrids can be used in a technique known as chimeraplasty (Cole-Strauss et al., 1999, Nucleic Acids Research 27(5):1323-1330 and Kmiec, 1999, Gene Therapy American Scientist 87(3):240-247). Homologous recombination procedures in *Physcomitrella patens* are also well known in the art and are contemplated for use herein. Whereas in the homologous recombination vector, the altered portion of the LPKSRP gene is flanked at its 5' and 3' ends by an additional nucleic acid molecule of the LPKSRP gene to allow for homologous recombination to occur between the exogenous LPKSRP gene carried by the vector and an endogenous LPKSRP gene, in a microorganism or plant. The additional flanking LPKSRP nucleic acid molecule is of sufficient length for successful homologous recombination with the endogenous gene. Typically, several hundreds of base pairs up to kilobases of flanking DNA (both at the 5' and 3' ends) are included in the vector (See e.g., Thomas, K. R., and Capecchi, M. R., 1987, Cell 51:503 for a description of homologous recombination vectors or Strepp et al., 1998, PNAS, 95(8):4368-4373 for cDNA based recombination in *Physcomitrella patens*). The vector is introduced into a microorganism or plant cell (e.g., via polyethylene glycol mediated DNA), and cells in which the introduced LPKSRP gene has homologously recombined with the endogenous LPKSRP gene are selected using art-known techniques.

In another embodiment, recombinant microorganisms can be produced that contain systems that allow for regulated expression of the introduced gene. For example, inclusion of an LPKSRP gene on a vector placing it under control of the lac operon permits expression of the LPKSRP gene only in the presence of IPTG. Such regulatory systems are well known in the art.

Whether present in an extra-chromosomal non-replicating vector or a vector that is integrated into a chromosome, the LPKSRP polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693-8711). Examples of plant expression vectors include those detailed in: Becker, D., Kemper, E., Schell, J. and Masterson, R., 1992, New plant binary vectors with selectable markers located proximal to the left border, Plant Mol. Biol. 20: 1195-1197; and Bevan, M. W., 1984, Binary *Agrobacterium* vectors for plant transformation, Nucl. Acid. Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38.

Plant gene expression should be operatively linked to an appropriate promoter conferring gene expression in a timely, cell specific, or tissue specific manner. Promoters useful in the expression cassettes of the invention include any promoter that is capable of initiating transcription in a plant cell. Such promoters include, but are not limited to, those that can be obtained from plants, plant viruses, and bacteria that contain genes that are expressed in plants, such as *Agrobacterium* and *Rhizobium*.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35S promoters (Odell et al., 1985, Nature 313:810-812), the sX CaMV 35S promoter (Kay et al., 1987, Science 236:1299-1302) the Sep1 promoter, the rice actin promoter (McElroy et al., 1990, Plant Cell 2:163-171), the *Arabidopsis* actin promoter, the ubiquitan promoter (Christensen et al., 1989, Plant Molec. Biol. 18:675-689), pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like.

Inducible promoters are preferentially active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoter from tobacco, *Arabidopsis*, and maize are inducible by infection with a pathogen; and the Adh1 promoter is induced by hypoxia and cold stress. Plant gene expression can also be facilitated via an inducible promoter (For review, see Gatz, 1997, Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992, Plant J. 2:397-404), and an ethanol inducible promoter (PCT Application No. WO 93/21334).

In one preferred embodiment of the present invention, the inducible promoter is a stress-inducible promoter. For the purposes of the invention, stress inducible promoters are preferentially active under one or more of the following stresses: sub-optimal conditions associated with salinity, drought, temperature, metal, chemical, pathogenic, and oxidative stresses. Stress inducible promoters include, but are not limited to, Cor78 (Chak et al., 2000, Planta 210:875-883; Hovath et al., 1993, Plant Physiol. 103:1047-1053), Cor15a (Artus et al., 1996, PNAS 93(23):13404-09), Rci2A (Medina et al., 2001, Plant Physiol. 125:1655-66; Nylander et al., 2001, Plant Mol. Biol. 45:341-52; Navarre and Goffeau, 2000, EMBO J. 19:2515-24; Capel et al., 1997, Plant Physiol. 115: 569-76), Rd22 (Xiong et al., 2001, Plant Cell 13:2063-83; Abe et al., 1997, Plant Cell 9:1859-68; Iwasaki et al., 1995, Mol. Gen. Genet. 247:391-8), cDet6 (Lang and Palve, 1992, Plant Mol. Biol. 20:951-62), ADH1 (Hoeren et al., 1998, Genetics 149:479-90), KAT1 (Nakamura et al., 1995, Plant Physiol. 109:371-4), KST1 (Müller-Röber et al., 1995, EMBO 14:2409-16), Rha1 (Terryn et al., 1993, Plant Cell 5:1761-9; Terryn et al., 1992, FEBS Lett. 299(3):287-90), ARSK1 (Atkinson et al., 1997, GenBank Accession # L22302, and PCT Application No. WO 97/20057), PtxA (Plesch et al., GenBank Accession # X67427), SbHRGP3 (Ahn et al., 1996, Plant Cell 8:1477-90), GH3 (Liu et al., 1994, Plant Cell 6:645-57), the pathogen inducible PRP1-gene promoter (Ward et al., 1993, Plant. Mol. Biol. 22:361-366), the heat inducible hsp80-promoter from tomato (U.S. Pat. No. 5,187,267), cold inducible alpha-amylase promoter from potato (PCT Application No. WO 96/12814), or the wound-inducible pinII-promoter (European Patent No. 375091). For other examples of drought, cold, and salt-inducible promoters, such as the RD29A promoter, see Yamaguchi-Shinozalei et al., 1993, Mol. Gen. Genet. 236:331-340.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, another-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm preferred, and seed coat-preferred. See Thompson et al., 1989, BioEssays 10:108. Examples of seed preferred promoters include, but are not limited to, cellulose synthase (celA), Cim1, gamma-zein, globulin-1, maize 19 kD zein (cZ19B1), and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991, Mol. Gen. Genet. 225(3): 459-67), the oleosin-promoter from *Arabidopsis* (PCT Application No. WO 98/45461), the phaseolin-promoter from *Phaseolus vulgaris* (U.S. Pat. No. 5,504,200), the Bce-4-promoter from *Brassica* (PCT Application No. WO 91/13980), or the legumin B4 promoter (LeB4; Baeumlein et al., 1992, Plant Journal, 2(2): 233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, *Sorghum* kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43:729-736).

The invention further provides a recombinant expression vector comprising an LPKSRP DNA molecule of the invention cloned into the expression vector in an anti-sense orientation. That is, the DNA molecule is operatively linked to a regulatory sequence in a manner that allows for expression (by transcription of the DNA molecule) of an RNA molecule that is antisense to an LPKSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type, into which the vector is introduced. For a discussion of the regulation of gene expression using antisense genes, see Weintraub, H. et al., 1986, Antisense RNA as a molecular tool for genetic analysis, Reviews—Trends in Genetics, Vol. 1(1), and Mol et al., 1990, FEBS Letters 268:427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an LPKSRP can be expressed in bacterial cells such as *C. glutamicum*, insect cells, fungal cells, or mammalian cells (such as Chinese hamster ovary cells (CHO) or COS cells), algae, ciliates, plant cells, fungi, or other microorganisms like *C. glutamicum*. Other suitable host cells are known to those skilled in the art.

A host cell of the invention, such as a prokaryotic or eukaryotic host cell in culture, can be used to produce (i.e., express) an LPKSRP. Accordingly, the invention further provides methods for producing LPKSRPs using the host cells of the invention. In one embodiment, the method comprises culturing the host cell of invention (into which a recombinant expression vector encoding an LPKSRP has been introduced, or into which genome has been introduced a gene encoding a wild-type or altered LPKSRP) in a suitable medium until the LPKSRP is produced. In another embodiment, the method further comprises isolating LPKSRPs from the medium or the host cell.

Another aspect of the invention pertains to isolated LPKSRPs, and biologically active portions thereof. An "isolated"

or "purified" polypeptide or biologically active portion thereof is free of some of the cellular material when produced by recombinant DNA techniques, or chemical precursors or other chemicals when chemically synthesized. The language "substantially free of cellular material" includes preparations of LPKSRP in which the polypeptide is separated from some of the cellular components of the cells in which it is naturally or recombinantly produced. In one embodiment, the language "substantially free of cellular material" includes preparations of an LPKSRP having less than about 30% (by dry weight) of non-LPKSRP material (also referred to herein as a "contaminating polypeptide"), more preferably less than about 20% of non-LPKSRP material, still more preferably less than about 10% of non-LPKSRP material, and most preferably less than about 5% non-LPKSRP material.

When the LPKSRP or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of LPKSRP in which the polypeptide is separated from chemical precursors or other chemicals that are involved in the synthesis of the polypeptide. In one embodiment, the language "substantially free of chemical precursors or other chemicals" includes preparations of an LPKSRP having less than about 30% (by dry weight) of chemical precursors or non-LPKSRP chemicals, more preferably less than about 20% chemical precursors or non-LPKSRP chemicals, still more preferably less than about 10% chemical precursors or non-LPKSRP chemicals, and most preferably less than about 5% chemical precursors or non-LPKSRP chemicals. In preferred embodiments, isolated polypeptides, or biologically active portions thereof, lack contaminating polypeptides from the same organism from which the LPKSRP is derived. Typically, such polypeptides are produced by recombinant expression of, for example, a *Physcomitrella patens* LPKSRP in a plant other than *Physcomitrella patens*, or microorganisms such as *C. glutamicum*, ciliates, algae, or fungi.

The nucleic acid molecules, polypeptides, polypeptide homologs, fusion polypeptides, primers, vectors, and host cells described herein can be used in one or more of the following methods: identification of *Physcomitrella patens* and related organisms; mapping of genomes of organisms related to *Physcomitrella patens*; identification and localization of *Physcomitrella patens* sequences of interest; evolutionary studies; determination of LPKSRP regions required for function; modulation of an LPKSRP activity; modulation of the metabolism of one or more cell functions; modulation of plant growth or plant water use efficiency; modulation of stress resistance; and modulation of expression of LPKSRP nucleic acids. In one embodiment of these methods, the LPKSRP functions as a lectin-like protein kinase.

The moss *Physcomitrella patens* is related to other mosses, such as *Ceratodon purpureus*, that are capable of growth in the absence of light. Mosses like *Ceratodon* and *Physcomitrella* share a high degree of sequence identity on the DNA sequence and polypeptide level allowing the use of heterologous screening of DNA molecules with probes evolving from other mosses or organisms, thus enabling the derivation of a consensus sequence suitable for heterologous screening or functional annotation and pre-diction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The LPKSRP nucleic acid molecules of the invention have a variety of uses. Most importantly, the nucleic acid and amino acid sequences of the present invention can be used to transform plants, thereby inducing tolerance to stresses such as drought, high salinity, and cold. The present invention therefore provides a transgenic plant transformed by an LPKSRP nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and forage crops, for example.

In particular, the present invention describes using the expression of PpLLPK-1 of *Physcomitrella patens* to engineer plants with increased water use efficiency and or drought-tolerant, salt-tolerant, and/or cold-tolerant plants. This strategy has herein been demonstrated for *Arabidopsis thaliana*, but its application is not restricted to this plant. Accordingly, the invention provides a transgenic plant containing an LPKSRP such as the PpLLPK-1 as defined in SEQ ID NO: 2, wherein the plant has increased growth and/or an increased tolerance to an environmental stress selected from one or more of the group consisting of drought, salt, heat, or freeze stresses. In a preferred embodiment, the environmental stress is drought.

Accordingly, the invention provides a method of producing a transgenic plant with an LPKSRP coding nucleic acid, wherein expression of the nucleic acid(s) in the plant results in increased tolerance to environmental stress as compared to a wild type variety of the plant comprising: (a) introducing into a plant cell an expression vector comprising an LPKSRP nucleic acid, and (b) generating from the plant cell a transgenic plant with increased growth and/or increased tolerance to an environmental stress as compared to a wild type variety of the plant. The plant cell includes, but is not limited to, a protoplast, gamete producing cell, and a cell that regenerates into a whole plant. As used herein, the term "transgenic" refers to any plant, plant cell, callus, plant tissue, or plant part that contains all or part of at least one recombinant polynucleotide. In many cases, all or part of the recombinant polynucleotide is stably integrated into a chromosome or stable extrachromosomal element, so that it is passed on to successive generations. In preferred embodiments, the LPKSRP nucleic acid encodes a protein comprising the polypeptide of SEQ ID NO: 2.

The present invention also provides a method of modulating a plant's growth and/or tolerance to an environmental stress comprising, modifying the expression of an LPKSRP coding nucleic acid in the plant. The plant's growth and/or tolerance to the environmental stress can be increased or decreased as achieved by increasing or decreasing the expression of an LPKSRP, respectively. Preferably, the plant's growth and/or tolerance to the environmental stress is increased by increasing expression of an LPKSRP. Expression of an LPKSRP can be modified by any method known to those of skill in the art. The methods of increasing expression of LPKSRPs can be used wherein the plant is either transgenic or not transgenic. In cases when the plant is transgenic, the plant can be transformed with a vector containing any of the above described LPKSRP coding nucleic acids, or the plant can be transformed with a promoter that directs expression of native LPKSRP in the plant, for example. The invention provides that such a promoter can be tissue preferred, developmentally regulated, stress inducible, or a combination thereof. Alternatively, non-transgenic plants can have native LPKSRP expression modified by inducing a native promoter. The expression of PpLLPK-1 as defined in SEQ ID NO: 2 in target plants can be accomplished by, but is not limited to, one of the following examples: (a) constitutive promoter, (b) stress-inducible promoter, (c) chemical-induced promoter, and (d) engineered promoter overexpression with, for example, zinc-finger derived transcription factors (Greisman and Pabo, 1997, Science 275:657).

In a preferred embodiment, transcription of the LPKSRP is modulated using zinc-finger derived transcription factors (ZFPs) as described in Greisman and Pabo, 1997, Science 275:657 and manufactured by Sangamo Biosciences, Inc. These ZFPs comprise both a DNA recognition domain and a functional domain that causes activation or repression of a target nucleic acid such as an LPKSRP nucleic acid. Therefore, activating and repressing ZFPs can be created that specifically recognize the LPKSRP promoters described above and used to increase or decrease LPKSRP expression in a plant, thereby modulating the growth and/or the stress tolerance of the plant. The pre-sent invention also includes identification of the homologs of PpLLPK-1 as defined in SEQ ID NO: 2 in a target plant, as well as the homolog's promoter. The invention also provides a method of increasing expression of a gene of interest within a host cell as compared to a wild type variety of the host cell, wherein the gene of interest is transcribed in response to an LPKSRP, comprising: (a) transforming the host cell with an expression vector comprising an LPKSRP coding nucleic acid, and (b) expressing the LPKSRP within the host cell, thereby increasing the expression of the gene transcribed in response to the LPKSRP, as compared to a wild type variety of the host cell.

In addition to introducing the LPKSRP nucleic acid sequences into transgenic plants, these sequences can also be used to identify an organism as being *Physcomitrella patens*, or a close relative thereof. Also, they may be used to identify the presence of *Physcomitrella patens*, or a relative thereof in a mixed population of microorganisms. The invention provides the nucleic acid sequences of a number of *Physcomitrella patens* genes; by probing the extracted genomic DNA of a culture of a unique or mixed population of microorganisms under stringent conditions with a probe spanning a region of a *Physcomitrella patens* gene that is unique to this organism, one can ascertain whether this organism is present.

Further, the nucleic acid and polypeptide molecules of the invention may serve as markers for specific regions of the genome. This has utility not only in the mapping of the genome, but also in functional studies of *Physcomitrella patens* polypeptides. For example, to identify the region of the genome to which a particular *Physcomitrella patens* DNA-binding polypeptide binds, the *Physcomitrella patens* genome could be digested, and the fragments incubated with the DNA-binding polypeptide. Those fragments that bind the polypeptide may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the polypeptide binds. Further, the nucleic acid molecules of the invention may be sufficiently identical to the sequences of related species such that these nucleic acid molecules may serve as markers for the construction of a genomic map in related mosses.

The LPKSRP nucleic acid molecules of the invention are also useful for evolutionary and polypeptide structural studies. The processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

Manipulation of the LPKSRP nucleic acid molecules of the invention may result in the production of LPKSRPs having functional differences from the wild-type LPKSRPs. These polypeptides may be improved in efficiency or activity, may be present in greater numbers in the cell than is usual, or may be decreased in efficiency or activity. The effect of the genetic modification in plants, *C. glutamicum*, fungi, algae, or ciliates on plant growth and/or stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469-714, VCH: Weinheim; Belter, P. A. et al., 1988, Bioseparations: downstream processing for biotechnology, John Wiley and Sons; Kennedy, J. F. and Cabral, J. M. S., 1992, Recovery processes for biological materials, John Wiley and Sons; Shaeiwitz, J. A. and Henry, J. D., 1988, Biochemical separations, in: Ulmann's Encyclopedia of Industrial Chemistry, vol. B3, Chapter 11, page 1-27, VCH: Weinheim; and Dechow, F. J., 1989, Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their growth and/or tolerance to drought, salt, and temperature stresses. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived there from can then be assayed for fail or alteration of their growth and/or tolerance to drought, salt, and temperature stresses.

The engineering of one or more LPKSRP genes of the invention may also result in LPKSRPs having altered activities, which indirectly impact the growth, stress response, and/or stress tolerance of algae, plants, ciliates, or fungi, or other microorganisms like *C. glutamicum*. For example, the normal biochemical processes of metabolism result in the production of a variety of products (e.g., hydrogen peroxide and other reactive oxygen species), which may actively interfere with these same metabolic processes. For example, peroxynitrite is known to nitrate tyrosine side chains, thereby inactivating some enzymes having tyrosine in the active site (Groves, J. T., 1999, Curr. Opin. Chem. Biol. 3(2):226-235). While these products are typically excreted, cells can be genetically altered to transport more products than is typical for a wild-type cell. By optimizing the activity of one or more LPKSRPs of the invention that are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, T., 1998, The Plant Journal 15:39-48). The resultant knockout cells can then be evaluated for their ability or capacity to tolerate various stress conditions, their response to various stress conditions, and the effect on the phenotype and/or genotype of the mutation. For other methods of gene inactivation, see U.S. Pat. No. 6,004,804 "Non-Chimeric Mutational Vectors" and Puttaraju et al., 1999, Spliceosome-mediated RNA trans-splicing as a tool for gene therapy, Nature Biotechnology 17:246-252.

The aforementioned mutagenesis strategies for LPKSRPs resulting in increased growth and/or increased stress tolerance are not meant to be limiting; variations on these strategies will be readily apparent to one skilled in the art. Using such strategies, and incorporating the mechanisms disclosed herein, the nucleic acid and polypeptide molecules of the invention may be utilized to generate algae, ciliates, plants, fungi, or other microorganisms like *C. glutamicum* expressing mutated LPKSRP nucleic acid and polypeptide molecules such that the growth and/or stress tolerance is improved. The present invention also provides antibodies that specifically bind to an LPKSRP, or a portion thereof, as encoded by a nucleic acid described herein. Antibodies can be made by many well-known methods (See, e.g., Harlow and Lane, "Antibodies; A Laboratory Manual," Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992, Bio/Technology 10:163-167; Bebbington et al., 1992, Bio/Technology 10:169-175).

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., eds., "Basic and Clinical Immunology," (Lange Medical Publications, Los Altos, Calif., Fourth Edition) and references cited therein, and in Harlow and Lane "Antibodies, A Laboratory Manual" Cold Spring Harbor Publications, New York, 1988. Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of *Physcomitrella patens* Cultures

For this study, plants of the species *Physcomitrella patens* (Hedw.) B.S.G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438-446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromols$^{-1m2}$ (white light; Philips TL 65W/25 fluorescent tube) and a light/dark change of 16/8 hours. The moss was either modified in liquid culture using Knop medium according to Reski and Abel (1985, Planta 165:354-358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of 1 g fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; and 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol, and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of H$_2$O+RNAse (50 mg/ml final concentration). The DNA was dissolved overnight at 4° C., and the RNAse digestion was subsequently carried out at 37° C. for 1 hour. Storage of the DNA took place at 4° C.

Example 3

Isolation of Total RNA and poly-(A)+ RNA and cDNA Library Construction from *Physcomitrella patens*

For the investigation of transcripts, both total RNA and poly-(A)$^+$ RNA were isolated. The total RNA was obtained from wild-type 9-day-old protonemata following the GTC-method (Reski et al., 1994, Mol. Gen. Genet., 244:352-359). The Poly(A)+ RNA was isolated using Dyna Beads® (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)primers, second strand synthesis by incubation with DNA polymerase I, Klenow enzyme and RNAseH digestion at 12° C. (2 hours), 16° C. (1 hour), and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany), and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (See Sambrook et al., 1989, Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

| | |
|---|---|
| 5'-CAGGAAACAGCTATGACC-3' | SEQ ID NO: 3 |
| 5'-CTAAAGGGAACAAAAGCTG-3' | SEQ ID NO: 4 |
| 5'-TGTAAAACGACGGCCAGT-3' | SEQ ID NO: 5 |

Sequences were processed and annotated using the software package EST-MAX commercially provided by Bio-Max (Munich, Germany). The program incorporates practically all bioinformatics methods important for functional and structural characterization of protein sequences. For reference, see the website at pedant.mips.biochem.mpg.de. The most important algorithms incorporated in EST-MAX are: FASTA (Very sensitive sequence database searches with estimates of statistical significance; Pearson W. R., 1990, Rapid and sensitive sequence comparison with FASTP and FASTA. Methods Enzymol. 183:63-98); BLAST (Very sensitive sequence database searches with estimates of statistical significance. Altschul S. F. et al., Basic local alignment search tool, Journal of Molecular Biology 215:403-10); PREDATOR (High-accuracy secondary structure prediction from single and multiple sequences. Frishman, D. and Argos, P., 1997, 75% accuracy in protein secondary structure prediction. Proteins, 27:329-335); CLUSTALW: Multiple sequence alignment. Thompson, J. D. et al., 1994, CLUSTAL W (improving the sensitivity of progressive multiple sequence alignment through sequence weighting, positions-specific gap penalties and weight matrix choice, Nucleic Acids Research, 22:4673-4680); TMAP (Transmembrane region prediction from multiply aligned sequences. Persson, B. and Argos, P., 1994, Prediction of transmembrane segments in proteins utilizing multiple sequence alignments. J. Mol. Biol. 237:182-192); ALOM2 (Transmembrane region prediction from single sequences. Klein, P. et al., Prediction of protein function from sequence properties: A discriminate analysis of a database. Biochim. Biophys. Acta 787:221-226 (1984). Version 2 by Dr. K. Nakai); PROSEARCH (Detection of PROSITE protein sequence patterns. Kolakowski L. F. Jr., Leunissen J. A. M., Smith J. E., 1992, ProSearch: fast searching of protein sequences with regular expression patterns related to protein structure and function. Biotechniques 13, 919-921);

BLIMPS (Similarity searches against a database of ungapped blocks, J. C. Wallace and Henikoff S., 1992); PATMAT (a searching and extraction program for sequence, pattern and block queries and databases, CABIOS 8:249-254. Written by Bill Alford).

Example 5

Identification of *Physcomitrella patens* ORFs Corresponding to PpLLPK-1

The *Physcomitrella patens* partial cDNA for partial PpLLPK-1 was identified in the *Physcomitrella patens* EST sequencing program using the program EST-MAX through BLAST analysis. The PpLLPK-1 predicted amino acid sequence shared significant sequence identity with lectin-like protein kinases as shown in Table 1.

TABLE 1

Degree of Amino Acid Identity and Similarity of PpLLPK-1 and Homologous Proteins.

| Swiss-Prot # | Protein name | Species | Identity (%) | Similarity (%) |
|---|---|---|---|---|
| Q7XIH7 | Putative lectin-like protein kinase | *Oryza sativa* (japonica cultivar-group) | 33 | 47 |
| Q9FHG4 | Serine/threonine-specific kinase like protein | *Arabidopsis thaliana* (Mouse-ear cress). | 32 | 46 |
| Q84ZH6 | Putative receptor-like protein kinase | *Oryza sativa* (japonica cultivar-group) | 29 | 41 |
| Q7XNZ0 | OSJNBa0081C01.18 protein | *Oryza sativa* (Rice) | 18 | 26 |
| T49986 | lectin-like protein kinase-like | *Arabidopsis thaliana* (mouse-ear cress) | 31 | 44 |

The synthetic oligonucleotide primers (MWG-Biotech) for the reaction were: CCCGGGCACCACCAGTAC-CTTTGCGTATGTG (SEQ ID NO: 6) and GTTAACAGCT-CAAAGTAATCTTGCCGTTCC (SEQ ID NO: 7). The primers designed contain an Xma1 site in the 5' region and a Hpa1 site in the 3' region for cloning purposes. The conditions for the reaction were standard conditions with PWO DNA polymerase (Roche). PCR was performed according to standard conditions and to manufacturer's protocols (Sambrook et al., 1989, Biometra T3 Thermocycler). The parameters for the reaction were: five minutes at 94° C. followed by five cycles of one minute at 94° C., one minute at 50° C., and 4 minutes at 72° C. This was followed by twenty-five cycles of one minute at 94° C., one minute at 65° C., and 4 minutes at 72° C. These parameters generated a fragment 4.0 kilobases long. The fragment was extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al., 1989). Transformed cells were selected for on LB agar containing 100 µg/ml carbenicillin, 0.8 mg X-gal (5-bromo-4-chloro-3-indolyl-β-D-galactoside), and 0.8 mg IPTG (isopropylthio-β-D-galactoside) grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones, and restriction mapping, was performed according to standard molecular biology techniques (Sambrook et al., 1989, Molecular Cloning, A Laboratory Manual, 2nd Edition, Cold Spring Harbor Laboratory Press, Cold Spring Harbor, N.Y.).

TABLE 2

Scheme and primers used for cloning of full-length clones

| Gene | Final product Sites | Isolation Method | Primers Race | Primers RT-PCR |
|---|---|---|---|---|
| PpLLPK-1 | Xma1/Hpa1 | 5' RACE and RT-PCR for Full-length clone | RC741: CCGTTGGACG-GAGCCGTAGTTT-TAA (SEQ ID. NO: 8) RC531: AGCAGCACCGAG-CACGGCGATAAGT (SEQ ID. NO: 9) RC224: GGCCGCCTTCGGC ATATAACCTCCAG (SEQ ID. NO: 10) | RC906: CCCGGGCAC-CACCAG-TACCTTTGCG-TATGTG (SEQ ID. NO: 6) RC907: GTTAA-CAGCTCAAAG-TAATCTTGCCGTT CC (SEQ ID. NO: 7) |

Example 6

Cloning of the Full-Length *Physcomitrella patens* cDNA Encoding for PpLLPK-1-Full-length Amplification As described below, a full-length sequence corresponding to PpLLPK-1 (SEQ ID NO: 1) was obtained by performing polymerase chain reaction (PCR) with gene-specific EST as the template DNA.

The full-length cDNA sequence of the *Physcomitrella patens* PpLLPK-1 (SEQ ID NO: 1) is shown in FIG. 1. The deduced amino acid sequence of the *Physcomitrella patens* PpLLPK-1 (SEQ ID NO: 2) is shown in FIG. 2. PpLLPK-1 was analyzed with Biomax and Vector NTI. The PpLLPK-1 amino acid sequence has homology to the lectin-like protein kinases or lectin receptor kinases (Table 1 and FIG. 3). A blast search of the PpLLPK-1 protein sequence against a patent sequence database using Pedant Pro (<e-50) identified numerous sequences with significant homology to the PpLLPK-1 sequence. The percent similarity and identity of the five most similar sequences to the PpLLPK-1 sequence are shown in Table 3, and an alignment of these sequences is shown in FIG. 4.

TABLE 3

Degree of Amino Acid Identity and Similarity of PpLLPK-1 and Homologous Sequences in Published Patent Applications.

| Gene ID | Publication number | Assignee | Similarity (%) | Identity (%) |
|---|---|---|---|---|
| ABB93833 | WO200210210-A2 | Bayer | 46 | 33 |
| ABB92247 | WO200210210-A2 | Bayer | 45 | 32 |
| ABB93318 | WO200210210-A2 | Bayer | 44 | 32 |
| ABB92654 | WO200210210-A2 | Bayer | 44 | 31 |
| AAB25109 | WO200042171-A1 | Genesis | 42 | 32 |

Example 7

Engineering *Arabidopsis* Plants by Overexpressing the Gene PpLLPK-1

Subcloning of PpLLPK-1 into the binary vector.

The fragment containing the *Physcomitrella patens* PpLLPK-1 sequence was sub-cloned from the recombinant PCR2.1 TOPO vector by double digestion with restriction enzymes (See Table 4) according to manufacturer's instructions. The subsequent fragment was excised from agarose gel with a QIAquick Gel Extraction Kit (QIAgen) according to manufacturer's instructions and ligated into the binary vector, which was cleaved with Xma1 and Hpa1 and dephosphorylated prior to ligation. The resulting recombinant vector contained the corresponding transcription factor in the sense orientation under the constitutive promoter.

TABLE 4

Listed are the names of the constructs used for plant transformation

| Gene | Enzymes used to generate gene fragment | Enzymes used to restrict pBPSJH001 | Binary Vector Construct |
|---|---|---|---|
| PpLLPK-1 | Xma1/Hpa1 | Xma1/Ecl136 | pBPSJYW033 |

*Agrobacterium* Transformation. The recombinant vectors were transformed into *Agrobacterium tumefaciens* C58C1 and PMP90 according to standard conditions (Hoefgen and Willmitzer, 1990).

Plant Transformation. *Arabidopsis thaliana* ecotype C24 were grown and transformed according to standard conditions (Bechtold 1993, Acad. Sci. Paris. 316:1194-1199; Bent et al. 1994, Science 265:1856-1860).

Growth Screen. T1 plants were screened for resistance to the selection agent conferred by the selectable marker gene, and seeds were collected. T2 and T3 seeds were screened for resistance to the selection agent conferred by the selectable marker gene on plates, and positive plants were transplanted into soil and grown in a growth chamber for 3 weeks. Soil moisture was maintained throughout this time at approximately 50% of the maximum water-holding capacity of soil.

The total water lost (transpiration) by the plant during this time was measured. After three weeks, the entire above-ground plant material was collected, dried at 65° C. for 2 days and weighed. The results are shown in Table 5. The ratio of above-ground plant dry weight to plant water use is Water Use Efficiency (WUE). Table 5 shows mean WUE, standard error for WUE, mean plant dry weight (DW), and standard error for DW for PpLLPK-1 overexpressing plants, wild-type controls, and transgenic vector-only controls. Data is from approximately 50 plants per genotype, 5 plants each of 10 independent transgenic lines, and 2 independent experiments.

TABLE 5

| Geno-type | Assay | Mean WUE (g l$^{-1}$) | WUE Standard Error (g l$^{-1}$) | Mean DW (g) | DW Standard Error (g) |
|---|---|---|---|---|---|
| PpLLPK-1 | G | 2.33 | 0.05 | 0.185 | 0.006 |
| Wild-type control | G | 1.95 | 0.05 | 0.112 | 0.006 |
| Vector only control | G | 2.26 | 0.04 | 0.165 | 0.004 |
| PpLLPK-1 | J | 1.94 | 0.08 | 0.119 | 0.008 |
| Wild-type control | J | 1.70 | 0.08 | 0.100 | 0.007 |
| Vector only control | J | 1.66 | 0.07 | 0.082 | 0.007 |

The above data is summarized in Table 6 below by presenting the percent difference from vector-only and wild-type controls for the PpLLPK-1 overexpressing plants. The data show that PpLLPK-1 plants have a significant increase in DW and WUE, as compared to the controls. PpLLPK-1 expressing plants demonstrated an approximately 29-42% increase in dry weight as compared to the controls, and an approximately 10-17% increase in water use efficiency as compared to the controls.

TABLE 6

| | WUE (% difference) | | DW (% difference) | |
|---|---|---|---|---|
| Assay | Relative to wild-type control | Relative to vector-only control | Relative to wild-type control | Relative to vector-only control |
| G | +20 | +3 | +65 | +12 |
| J | +14 | +17 | +19 | +46 |
| Mean | +17 | +10 | +42 | +29 |

The PpLLPK-1 overexpressing plants, wild-type control plants, and transgenic vector-only control plants also were subjected to either well-watered conditions or to several cycles of drought stress, and the plants' above-ground biomass was measured. The mean dry weight values and standard error for the PpLLPK-1 overexpressing plants, the wild-type control plants, and the vector-only control plants are given in Table 7, which is presented as FIG. 5, under well-watered and drought-cycling conditions. This DW data is expressed in Table 8 as percent difference from wild-type control and this demonstrates that PpLLPK-1 overexpression increased DW by 25% under both well-watered and repeated cycles of drought stress:

TABLE 8

| Well-watered DW (% difference) | Cycling drought DW (% difference) |
|---|---|
| +25 | +25 |

Drought Tolerance Screening. T1 seedlings are transferred to dry, sterile filter paper in a petri dish and allowed to desiccate for two hours at 80% RH (relative humidity) in a Sanyo Growth Cabinet MLR-350H, micromols$^{-1m2}$ (white light; Philips TL 65W/25 fluorescent tube). The RH is then decreased to 60%, and the seedlings are desiccated further for eight hours. Seedlings are then removed and placed on ½ MS 0.6% agar plates supplemented with 2 µg/ml benomyl (Sigma-Aldrich) and scored after five days. The transgenic plants are then screened for their improved drought tolerance, demonstrating that the transgene confers drought tolerance.

Freezing Tolerance Screening. Seedlings are moved to petri dishes containing ½ MS 0.6% agar supplemented with 2% sucrose and 2 µg/ml benomyl. After four days, the seedlings are incubated at 4° C. for 1 hour and then covered with shaved ice. The seedlings are then placed in an Environmental Specialist ES2000 Environmental Chamber and incubated for 3.5 hours beginning at −1.0° C., and decreasing −1° C. each hour. The seedlings are then incubated at −5.0° C. for 24 hours and then allowed to thaw at 5° C. for 12 hours. The water is poured off, and the seedlings are scored after 5 days. The transgenic plants are screened for their improved cold tolerance, demonstrating that transgene expression confers cold tolerance.

Salt Tolerance Screening. Seedlings are transferred to filter paper soaked in ½ MS and placed on ½ MS 0.6% agar supplemented with 2 µg/ml benomyl the night before the salt tolerance screening. For the salt tolerance screening, the filter paper with the seedlings is moved to stacks of sterile filter paper, soaked in 50 mM NaCl, in a petri dish. After two hours, the filter paper with the seedlings is moved to stacks of sterile filter paper, soaked with 200 mM NaCl, in a petri dish. After two hours, the filter paper with the seedlings is moved to stacks of sterile filter paper, soaked in 600 mM NaCl, in a petri dish. After 10 hours, the seedlings are moved to petri dishes containing ½ MS 0.6% agar supplemented with 2 µg/ml benomyl. The seedlings are scored after 5 days.

Example 8

Detection of the PpSCL Transgenes in the Transgenic *Arabidopsis* Lines

One leaf from a wild type and a transgenic *Arabidopsis* plant is homogenized in 250 µl Hexadecyltrimethyl ammonium bromide (CTAB) buffer (2% CTAB, 1.4 M NaCl, 8 mM EDTA, and 20 mM Tris, pH 8.0) and 1 µl β-mercaptoethanol. The samples are incubated at 60-65° C. for 30 minutes, and 250 µl of Chloroform is then added to each sample. The samples are vortexed for 3 minutes and centrifuged for 5 minutes at 18,000×g. The supernatant is taken from each sample, and 150 µl isopropanol is added. The samples are incubated at room temperature for 15 minutes, and centrifuged for 10 minutes at 18,000×g. Each pellet is washed with 70% ethanol, dried, and resuspended in 20 µl TE. Then, 2.5 µl of the above suspension is used in a 50 µl PCR reaction using Taq DNA polymerase (Roche Molecular Biochemicals) according to the manufacturer's instructions. Binary vector plasmid with each gene cloned in can be used as positive control, and the wild type C24 genomic DNA used as negative control in the PCR reactions. Then, 10 µl of each PCR reaction is analyzed on 0.8% agarose/ethidium bromide gel.

The PCR program can be as follows: 30 cycles of 1 minute at 94° C., 30 seconds at 62° C., and 1 minute at 72° C., followed by 5 minutes at 72° C. Gene-specific primers are listed below.

Example 9

Detection of the PpLLPK-1 Transgene mRNA in Transgenic *Arabidopsis* Lines

Transgene expression is detected using RT-PCR. Total RNA is isolated from stress-treated plants using a procedure adapted from (Verwoerd et al., 1989, NAR 17:2362). Leaf samples (50-100 mg) are collected and ground to a fine powder in liquid nitrogen. Ground tissue is resuspended in 500 µl of an 80° C., 1:1 mixture, of phenol to extraction buffer (100 mM LiCl, 100 mM Tris pH8, 10 mM EDTA, 1% SDS), followed by brief vortexing to mix. After the addition of 250 µl of chloroform, each sample is vortexed briefly. Samples are then centrifuged for 5 minutes at 12,000×g. The upper aqueous phase is removed to a fresh eppendorf tube. RNA was precipitated by adding ¹⁄₁₀$^{th}$ volume 3 M sodium acetate and 2 volumes 95% ethanol. Samples are mixed by inversion and placed on ice for 30 minutes. RNA is pelleted by centrifugation at 12,000×g for 10 minutes. The supernatant is removed and pellets briefly air-dried. RNA sample pellets are resuspended in 10 µl DEPC treated water.

To remove contaminating DNA from the samples, each can be treated with RNase-free DNase (Roche) according to the manufacturer's recommendations. cDNA is synthesized from total RNA using the Superscript First Strand cDNA Synthesis System for RT-PCT (Gibco-BRL) following the manufacturer's recommendations. PCR amplification of a gene-specific fragment from the synthesized cDNA is performed using Taq DNA polymerase (Roche) and gene-specific primers (See Table 13 for primers) in the following reaction: 1×PCR buffer, 1.5 mM MgCl$_2$, 0.2 µM each primer, 0.2 µM dNTPs, 1 unit polymerase, 5 µl cDNA from synthesis reaction. Amplification is performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products are run on a 1% agarose gel, stained with ethidium bromide, and visualized under UV light using the Quantity-One gel documentation system (Bio-Rad).

Example 10

Engineering Stress-Tolerant Soybean Plants by Overexpressing the PpSCL-1 Gene

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige and Skoog, 1962) medium supplemented with 100 µM acetosyringone. Bacteria cultures are incubated in this pre-induction medium for 2 hours at room temperature before use. The axis of soybean zygotic seed embryos at approximately 15% moisture content are imbibed for 2 hours at room temperature with the pre-induced *Agrobacterium* suspension culture. The embryos are removed from the imbibition culture and were transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the *agrobacteria*. The liquid medium is used to moisten the sterile filter paper. The embryos are incubated during 4 weeks at 25° C., under 150 µmol m$^{-2}$sec$^{-1}$ and 12 hours photoperiod. Once the seedlings produced roots, they are transferred to sterile metro-mix soil. The medium of the in vitro plants is washed off before transferring the plants to soil. The plants are kept under a plastic cover for 1 week to favor the acclimatization process. Then the plants are transferred to a growth room where they were incubated at 25° C., under 150 µmol m$^{-2}$sec$^{-1}$ light intensity and 12 hours photoperiod for about 80 days.

The transgenic plants are then screened for their improved growth and/or drought, salt, and/or cold tolerance according to the screening method described in Example 7 demonstrating that transgene expression confers increased growth and/or increased stress tolerance.

Example 11

Engineering Stress-tolerant Rapeseed/Canola Plants by Overexpressing the PpLLPK-1 Gene The method of plant transformation described herein is also applicable to *Brassica* and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed and the seeds are air dried overnight in a half-open sterile Petri dish. During this period, the seeds lose approx. 85% of its water content. The seeds are then stored at room temperature in a sealed Petri dish until further use. DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are then screened for their improved growth and/or stress tolerance according to the screening method described in Example 7 demonstrating that transgene expression confers increased growth and/or increased stress tolerance.

Example 12

Engineering Stress-tolerant Corn Plants by Overexpressing PpLLPK-1 Gene

Transformation of maize (*Zea Mays* L.) is performed with the method described by Ishida et al. 1996. Nature Biotch 14745-50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are then screened for their improved growth and/or drought, salt, and cold tolerance according to the screening method described in Example 7 demonstrating that transgene expression confers increased growth and/or increased stress tolerance.

Example 13

Greenhouse Screening for Stress Tolerant Corn Plants—High Throughput Drought Performance Screen Segregating transgenic corn seeds for a transformation event are planted in small pots. Each of these plants is uniquely labeled, sampled and analyzed for transgene copy number. Transgene positive and negative plants are marked and paired with similar sizes for transplanting together to large pots. This provides a uniform and competitive environment for the transgene positive and negative plants. The large pots are watered to a certain percentage of the field water capacity of the soil depending the severity of water-stress desired. The soil water level is maintained by watering every other day. Plant growth and physiology traits such as height, stem diameter, leaf rolling, plant wilting, leaf extension rate, leaf water status, chlorophyll content and photosynthesis rate are measured during the growth period. After a period of growth, the above ground portion of the plants is harvested, and the fresh weight and dry weight of each plant are taken. A comparison of phenotype between the transgene positive and negative plants is then made.

Water Use Efficiency (WUE) Assay

Transgene positive and negative corn seedlings for a transformation event are trans-planted into a pot with a given amount of soil and water. The pots are covered with caps that permit the seedlings to grow through but minimize water loss. Each pot is weighed periodically and water added to maintain the initial water content. At the end of the experiment, the fresh and dry weight of each plant are measured, the water consumed by each plant is calculated and WUE of each plant is computed. Plant growth and physiology traits such as WUE, height, stem diameter, leaf rolling, plant wilting, leaf extension rate, leaf water status, chlorophyll content and photosynthesis rate are measured during the experiment. A comparison of phenotype between the transgenic plants and control plants is then made.

Desiccation Assay

Segregating transgenic corn seeds for a transformation event are planted in small pots. These pots are kept in an area in the greenhouse that has uniform environmental conditions, and cultivated optimally. Each of these plants is uniquely labeled, sampled and analyzed for transgene copy number. The plants are allowed to grow under theses conditions until they reach a predefined growth stage. Water is then withheld. Plant growth and physiology traits such as height, stem diameter, leaf rolling, plant wilting, leaf extension rate, leaf water status, chlorophyll content and photosynthesis rate are measured as stress intensity increases. A comparison of the phenotype between transgene positive and negative plants is then made.

Cycling Drought Assay

Segregating transgenic corn seeds for a transformation event are planted in small pots. These pots are kept in an area in the greenhouse that has uniform environmental conditions, and cultivated optimally. Each of these plants is uniquely labeled, sampled and analyzed for transgene copy number. The plants are allowed to grow under theses conditions until they reach a predefined growth stage. Plants are then repeatedly watered to saturation at a fixed interval of time. This water/drought cycle is repeated for the duration of the experiment. Plant growth and physiology traits such as height, stem diameter, leaf rolling, leaf extension rate, leaf water status, chlorophyll content and photosynthesis rate are measured during the growth period. At the end of the experiment, the plants are harvested for above-ground fresh and dry weight. A comparison of the phenotype between transgene positive and negative plants is then made.

Field Screening for Corn Plants—Segregating Corn Drought-tolerance Screening Under Rain-free Conditions Managed-drought stress at a single location or multiple locations is used. Crop water availability is controlled by drip tape or overhead irrigation at a location which has less than 10 cm rainfall and minimum temperatures greater than 5° C. expected during an average 5 month season, or a location with expected in-season precipitation intercepted by an automated "rain-out shelter" which retracts to provide open field conditions when not required. Standard agronomic practices in the area are followed for soil preparation, planting, fertilization and pest control. Each plot is sown with seed segregating for the presence of a single transgenic insertion event. A Taqman transgene copy number assay is used on leaf samples to differentiate the transgenics from null-segregant control plants. Plants that have been genotyped in this manner are also scored for a range of phenotypes related to drought-tolerance, growth and yield. These phenotypes include plant height, grain weight per plant, grain number per plant, ear number per plant, above ground dry-weight, leaf conductance to water vapor, leaf $CO_2$ uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf angle, leaf rolling and survival. All measurements are made with commercially available instrumentation for field physiology, using the standard protocols provided by the manufacturers. Individual plants are used as the replicate unit per event.

Non-Segregating Corn Drought-Tolerance Screening Under Rain-Free Conditions

Managed-drought stress at a single location or multiple locations is used. Crop water availability is controlled by drip tape or overhead irrigation at a location which has less than 10 cm rainfall and minimum temperatures greater than 5° C. expected during an average 5 month season, or a location with expected in-season precipitation intercepted by an automated "rain-out shelter" which retracts to provide open field conditions when not required. Standard agronomic practices in the area are followed for soil preparation, planting, fertilization and pest control. Trial layout is designed to pair a plot containing a non-segregating transgenic event with an adjacent plot of null-segregant controls. A null segregant is progeny (or lines derived from the progeny) of a transgenic plant that does not contain the transgene due to Mendelian segregation. Additional replicated paired plots for a particular event are distributed around the trial. A range of phenotypes related to drought-tolerance, growth and yield are scored in the paired plots and estimated at the plot level. When the measurement technique could only be applied to individual plants, these are selected at random each time from within the plot. These phenotypes include plant height, grain weight per plant, grain number per plant, ear number per plant, above ground dry-weight, leaf conductance to water vapor, leaf $CO_2$ uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plots are used as the replicate unit per event.

Multi-location Corn Drought-tolerance and Yield Screening

Five to twenty locations encompassing major corn growing regions are selected. These are widely distributed to provide a range of expected crop water availabilities based on average temperature, humidity, precipitation and soil type. Crop water availability is not modified beyond standard agronomic practices. Trial layout is designed to pair a plot containing a non-segregating transgenic event with an adjacent plot of null-segregant controls. A range of phenotypes related to drought-tolerance, growth and yield are scored in the paired plots and estimated at the plot level. When the measurement technique could only be applied to individual plants, these are selected at random each time from within the plot. These phenotypes included plant height, grain weight per plant, grain number per plant, ear number per plant, above ground dry-weight, leaf conductance to water vapor, leaf CO2 uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plots are used as the replicate unit per event.

Example 14

Engineering Stress-tolerant Wheat Plants by Overexpressing the PpLLPK-1 Gene

Transformation of wheat is performed with the method described by Ishida et al. 1996 Nature Biotch. 14745-50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved growth and/or stress tolerance according to the screening method described in Example 7 demonstrating that transgene expression confers increased growth and/or increased stress tolerance.

Example 15

Engineering Stress-tolerant Rice Plants by Overexpressing the PpLLPK-1 Gene

The entry clone containing a *Physcomitrella patens* cDNA encoding for PpLLPK-1 is subsequently used in an LR reaction with p0831 a destination vector used for *Oryza sativa* transformation. This vector contains as functional elements within the T-DNA borders: a plant selectable marker; a visual marker expression cassette; and a Gateway cassette intended for LR in vivo recombination with the sequence of interest already cloned in the entry clone. A rice promoter for constitutive expression (SEQ ID NO:11—see FIG. 6 attached) is located upstream of this Gateway cassette.

After the LR recombination step the resulting expression vector p074 (FIG. 7 attached) is transformed into the *Agrobacterium* strain LBA4404 and subsequently to *Oryza sativa* plants. Transformed rice plants are allowed to grow and are then examined for increased growth and/or stress tolerance.

Approximately 15 to 20 independent PpLLPK-1 transformants (T0) are generated. The primary transformants are transferred from tissue culture chambers to a greenhouse for growing and harvest of T1 seed. Five events of which the T1 progeny segregated 3:1 for presence/absence of the transgene are retained. For each of these events, 10 T1 seedlings containing the transgene (hetero- and homo-zygotes), and 10 T1 seedlings lacking the transgene (nullizygotes), are selected by visual marker screening. The selected T1 plants are transferred to a greenhouse. Each plant receives a unique barcode label to link unambiguously the phenotyping data to the corresponding plant. The selected T1 plants are grown on soil in 10 cm diameter pots under the following environmental settings: photoperiod=11.5 h, daylight intensity=30,000 lux or more, daytime temperature=28° C. or higher, night time temperature=22° C., relative humidity=60-70%.

Transgenic plants and the corresponding nullizygotes are grown side-by-side at random positions. From the stage of sowing until the stage of maturity the plants are passed several times through a digital imaging cabinet. At each time point digital images (2048×1536 pixels, 16 million colours) are taken of each plant from at least 6 different angles.

The data obtained for PpLLPK-1 in the first experiment are confirmed in a second experiment with T2 plants. Lines that have the correct expression pattern are selected for further analysis. Seed batches from the positive plants (both hetero- and homozygotes) in T1, are screened by monitoring marker expression. For each chosen event, the heterozygote seed batches are then retained for T2 evaluation. Within each seed batch an equal number of positive and negative plants are grown in the greenhouse for evaluation.

Transgenic plants are screened for their improved growth and/or stress tolerance according to the screening method described in Example 7 demonstrating that transgenic expression of the PpLLPK-1 gene confers increased growth and/or stress tolerance in rice plants.

Example 16

Identification of Homologous and Heterologous Genes

Gene sequences can be used to identify homologous or heterologous genes from cDNA or genomic libraries. Homologous genes (e.g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by, e.g., UV cross linking. Hybridization is carried out at high stringency conditions. In aqueous solution, hybridization and washing is performed at an ionic strength of 1 M NaCl and a temperature of 68° C. Hybridization probes are generated by, e.g., radioactive ($^{32}$P) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10-20 amino acids) can be carried out by using synthetic radio labeled oligonucleotide probes. Radiolabeled oligonucleotides are prepared by phosphorylation of the 5' end of two complementary oligonucleotides with T4 polynucleotide kinase. The complementary oligonucleotides are annealed and ligated to form concatemers. The double stranded concatemers are then radiolabeled by, for example, nick transcription. Hybridization is normally performed at low stringency conditions using high oligonucleotide concentrations.

Oligonucleotide hybridization solution:
6×SSC
M sodium phosphate
mM EDTA (pH 8)
0.5% SDS
100 µg/ml denatured salmon sperm DNA
% nonfat dried milk During hybridization, the temperature is lowered stepwise to 5-10° C. below the estimated oligonucleotide $T_m$, or down to room temperature, followed by washing steps and autoradiography. Washing is performed with low stringency, such as 3 washing steps using 4×SSC. Further details are described by Sambrook, J. et al., 1989, "Molecular Cloning: A Laboratory Manual," Cold Spring Harbor Laboratory Press or Ausubel, F. M. et al., 1994, "Current Protocols in Molecular Biology," John Wiley & Sons.

Example 17

Identification of Homologous Genes by Screening Expression Libraries with Antibodies cDNA clones can be used to produce recombinant protein for example in *E. coli* (e.g. Qiagen QIAexpress pQE system). Recombinant proteins are then normally affinity purified via Ni-NTA affinity chromatography (Qiagen). Recombinant proteins are then used to produce specific antibodies for example by using standard techniques for rabbit immunization. Antibodies are affinity purified using a Ni-NTA column saturated with the recombinant antigen as described by Gu et al., 1994, BioTechniques 17:257-262. The antibody can be used to screen expression cDNA libraries to identify homologous or heterologous genes via an immunological screening (Sambrook, J. et al., 1989, "Molecular Cloning: A Laboratory Manual," Cold Spring Harbor Laboratory Press or Ausubel, F. M. et al., 1994, "Current Protocols in Molecular Biology," John Wiley & Sons).

Example 18

In Vivo Mutagenesis

In vivo mutagenesis of microorganisms can be performed by passage of plasmid (or other vector) DNA through *E. coli* or other microorganisms (e.g. *Bacillus* spp. or yeasts such as *Saccharomyces cerevisiae*), which are impaired in their capabilities to maintain the integrity of their genetic information. Typical mutator strains have mutations in the genes for the DNA repair system (e.g., mutHLS, mutD, mutT, etc.; for reference, see Rupp, W. D., 1996, DNA repair mechanisms, in: *Escherichia coli* and *Salmonella*, p. 2277-2294, ASM: Washington). Such strains are well known to those skilled in the art. The use of such strains is illustrated, for example, in Greener, A. and Callahan, M., 1994, Strategies 7:32-34. Transfer of mutated DNA molecules into plants is preferably done after selection and testing in microorganisms. Transgenic plants are generated according to various examples within the exemplification of this document.

Example 19

Purification of the Desired Product from Transformed Organisms

Recovery of the desired product from plant material (i.e., *Physcomitrella patens* or *Arabidopsis thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, the cells can be harvested from the culture by low-speed centrifugation, and the cells can be lysed by standard techniques, such as mechanical force or sonification. Organs of plants can be separated mechanically from other tissue or organs. Following homogenization, cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin, while the sample is not. Such chromatography steps may be repeated as necessary, using the same or different chromatography resins. One skilled in the art would be well versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, 1986, D. F. Biochemical Engineering Fundamentals, McGraw-Hill: New York. Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994, Appl. Environ. Microbiol. 60:133-140; Malakhova et al., 1996, Biotekhnologiya 11:27-32; and Schmidt et al., 1998, Bioprocess Engineer. 19:67-70; Ulmann's Encyclopedia of Industrial Chemistry, 1996, vol. A27, VCH: Weinheim, p. 89-90, p. 521-540, p. 540-547, p. 559-566, 575-581, and p. 581-587; Michal, G., 1999, Biochemical Pathways: An Atlas of Biochemistry and Molecular Biology, John Wiley and Sons; Fallon, A. et al., 1987, Applications of HPLC in Biochemistry in: Laboratory Techniques in Biochemistry and Molecular Biology, vol. 17.

The invention claimed is:

1. A method of increasing a plant's tolerance to drought comprising the step of transforming the plant with a polynucleotide encoding a lectin-like protein kinase stress related polypeptide, wherein the polynucleotide is selected from the group consisting of:
    (a) a polynucleotide comprising nucleotides 1 to 2049 of SEQ ID NO:1; and
    (b) a polynucleotide encoding a polypeptide comprising amino acids 1 to 672 of SEQ ID NO:2.

2. The method of claim 1, wherein the polynucleotide encodes the polypeptide comprising amino acids 1 to 672 of SEQ ID NO:2.

3. A method of producing a transgenic plant containing a polynucleotide encoding a lectin-like protein kinase stress related polypeptide comprising the steps of:
    (i) transforming a plant cell with an expression vector comprising the polynucleotide; and
    (ii) generating from the plant cell the transgenic plant, wherein the nucleic acid is selected from the group consisting of:
    (a) a polynucleotide comprising nucleotides 1 to 2049 of SEQ ID NO:1; and
    (b) a polynucleotide encoding a polypeptide comprising amino acids 1 to 672 of SEQ ID NO:2
and wherein the transgenic plant has increased tolerance to drought as compared to a wild type variety of the plant.

4. The method of claim 3, wherein the plant is a monocot.

5. The method of claim 3, wherein the plant is a dicot.

6. The method of claim 3, wherein the plant is selected from the group consisting of maize, wheat, rye, oat, triticale, rice, barley, soybean, peanuts, cotton, rapeseed, canola, manihot, pepper, sunflower, tagetes, solenaceous plants, potato, tobacco, eggplant, tomato, Vicia species, pea, alfalfa, coffee, cacao, tea, *Salix* species, oil palm, coconut, perennial grass and forage crop plants.

7. The method of claim 3, wherein the polynucleotide encodes the polypeptide comprising amino acids 1 to 672 of SEQ ID NO:2.

8. A transgenic plant cell transformed with a polynucleotide selected from the group consisting of:
    (a) a polynucleotide comprising nucleotides 1 to 2049 of SEQ ID NO:1; and
    (b) a polynucleotide encoding a polypeptide comprising amino acids 1 to 672 of SEQ ID NO:2.

9. A transgenic plant transformed with a polynucleotide selected from the group consisting of:
    (a) a polynucleotide comprising nucleotides 1 to 2049 of SEQ ID NO:1; and
    (b) a polynucleotide encoding a polypeptide comprising amino acids 1 to 672 of SEQ ID NO:2.

10. A transgenic seed comprising a plant cell transformed with a polynucleotide that encodes a lectin-like protein kinase stress related polypeptide, wherein the polynucleotide is selected from the group consisting of
    (a) a polynucleotide comprising nucleotides 1 to 2049 of SEQ ID NO:1; and
    (b) a polynucleotide encoding a polypeptide comprising amino acids 1 to 672 of SEQ ID NO:2;
    wherein the seed is true breeding for an increased tolerance to drought stress as compared to a wild type variety of the seed.

11. An isolated polypeptide comprising amino acids 1 to 672 of SEQ ID NO:2.

12. A polynucleotide that encodes a lectin-like protein kinase stress related polypeptide, wherein the polynucleotide is selected from the group consisting of:
    (a) a polynucleotide comprising nucleotides 1 to 2049 of SEQ ID NO:1; and
    (b) a polynucleotide encoding a polypeptide comprising amino acids 1 to 672 of SEQ ID NO:2.

13. The polynucleotide of claim 12, which comprises nucleotides 1 to 2049 of SEQ ID NO:1.

14. The polynucleotide of claim 12, which encodes a polypeptide comprising amino acids 1 to 672 of SEQ ID NO:2.

* * * * *